(12) United States Patent
Bass et al.

(10) Patent No.: US 7,723,478 B2
(45) Date of Patent: May 25, 2010

(54) DKR POLYPEPTIDES

(75) Inventors: Michael Brian Bass, Thousand Oaks, CA (US); John Kevin Sullivan, Newbury Park, CA (US); Lars Eyde Theill, Thousand Oaks, CA (US); Daguang Wang, New York, NY (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 11/893,211

(22) Filed: Aug. 14, 2007

(65) Prior Publication Data

US 2008/0057540 A1 Mar. 6, 2008

Related U.S. Application Data

(60) Continuation of application No. 10/998,271, filed on Nov. 24, 2004, now abandoned, which is a continuation of application No. 09/976,736, filed on Oct. 9, 2001, now abandoned, which is a division of application No. 09/161,241, filed on Sep. 25, 1998, now Pat. No. 6,344,541.

(51) Int. Cl.
  *C07K 14/00* (2006.01)
(52) U.S. Cl. ..................................... 530/350
(58) Field of Classification Search ................. 530/350
  See application file for complete search history.

(56) References Cited

U.S. PATENT DOCUMENTS

| | | | |
|---|---|---|---|
| 3,773,919 | A | 11/1973 | Boswell et al. |
| 4,892,538 | A | 1/1990 | Aebischer et al. |
| 4,970,154 | A | 11/1990 | Chang |
| 5,011,472 | A | 4/1991 | Aebischer et al. |
| 5,106,627 | A | 4/1992 | Aebischer et al. |
| 5,168,050 | A | 12/1992 | Hammonds, Jr. et al. |
| 5,252,714 | A | 10/1993 | Harris et al. |
| 5,399,346 | A | 3/1995 | Anderson et al. |
| 5,489,743 | A | 2/1996 | Robinson et al. |
| 5,525,486 | A | 6/1996 | Honjo et al. |
| 5,557,032 | A | 9/1996 | Mak |
| 5,593,875 | A | 1/1997 | Wurm et al. |
| 5,631,236 | A | 5/1997 | Woo et al. |
| 5,635,399 | A | 6/1997 | Kriegler et al. |
| 5,653,975 | A | 8/1997 | Baetge et al. |
| 5,672,344 | A | 9/1997 | Kelly et al. |
| 5,676,954 | A | 10/1997 | Brigham |
| 5,679,559 | A | 10/1997 | Kim et al. |
| 6,844,422 | B1 | 1/2005 | Niehrs et al. |
| 2002/0119130 | A1 | 8/2002 | Eaton et al. |
| 2003/0068312 | A1 | 4/2003 | McCarthy |
| 2004/0234515 | A9 | 11/2004 | McCarthy |
| 2005/0069915 | A1 | 3/2005 | McCarthy |
| 2005/0079173 | A1 | 4/2005 | Niehrs et al. |
| 2006/0294605 | A1 | 12/2006 | McCarthy |
| 2007/0077244 | A1 | 4/2007 | Niehrs et al. |

FOREIGN PATENT DOCUMENTS

| | | |
|---|---|---|
| DE | 19747418.7 | 11/1998 |
| EP | 0036676 | 3/1979 |
| EP | 0058481 | 1/1982 |
| EP | 0088046 | 2/1983 |
| EP | 0143949 | 10/1984 |
| EP | 0133988 | 3/1985 |
| EP | 0154316 | 3/1985 |
| EP | 0401384 | 12/1989 |
| WO | 91/10425 | 7/1991 |
| WO | 94/28122 | 12/1994 |
| WO | 96/40958 | 12/1996 |
| WO | 97/48275 | 12/1997 |
| WO | 98/23730 | 6/1998 |
| WO | 98/27932 | 7/1998 |
| WO | 98/35043 | 8/1998 |
| WO | 98/46755 | 10/1998 |
| WO | 99/03990 | 1/1999 |
| WO | 99/06549 | 2/1999 |
| WO | 99/14328 | 3/1999 |
| WO | 00/12708 | 3/2000 |
| WO | 00/18914 | 4/2000 |
| WO | 00/53756 | 9/2000 |
| WO | 00/78961 | 12/2000 |
| WO | 01/04311 | 1/2001 |
| WO | 01/16318 | 3/2001 |
| WO | 01/38528 | 5/2001 |
| WO | 01/40466 | 6/2001 |
| WO | 01/54477 | 8/2001 |
| WO | 01/57188 | 8/2001 |
| WO | 01/57190 | 8/2001 |
| WO | 01/68848 | 9/2001 |

OTHER PUBLICATIONS

Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987).*
Lin et al Biochemistry USA vol. 14:1559-1563 (1975).*
Ibragimova and Eade (Biophysical Journal, Oct. 1999, vol. 77, pp. 2191-2198).*
GenBankTM Accession No. AA765298 for NCI_CGAP_GCB1 *Homo sapiens* cDNA clone IMAGE:1303697 3', mRNA sequence (1998).
GenBankTM Accession No. AA770231 Soares_testis_NHT *Homo sapiens* cDNA clone 1322151 3', mRNA sequence (1998).
GenBankTM Accession No. AA774161 for Stratagene hNT neuron (#937233) *Homo sapiens* cDNA clone IMAGE:858573 3', mRNA sequence (1998).
GenBankTM Accession No. AA815342 Soares_testis_NHT *Homo sapiens* cDNA clone 1375447 3', mRNA sequence (1998).
GenBankTM Accession No. AA826797 for NCI_CGAP_Pr24 *Homo sapiens* cDNA clone IMAGE:1174528 3', mRNA sequence (1998).

(Continued)

*Primary Examiner*—Lynn Bristol
(74) *Attorney, Agent, or Firm*—Scott L. Ausenhus

(57) ABSTRACT

Disclosed are nucleic acid molecules encoding novel DKR polypeptides. Also disclosed are methods of preparing the nucleic acid molecules and polypeptides, and methods of using these molecules.

3 Claims, 25 Drawing Sheets

OTHER PUBLICATIONS

GenBank™ Accession No. AA854987 Soares_testis_NHT *Homo sapiens* cDNA clone IMAGE:1394074 3', mRNA sequence (1998).

GenBank™ Accession No. AA868111 Soares_testis_NHT *Homo sapiens* cDNA clone IMAGE:1407610 3' similar to contain element MSR1 repetitive element, mRNA sequence (1998).

GenBank™ Accession No. AA991644 for NCI_CGAP_GC2 *Homo sapiens* cDNA clone IMAGE:1612003 3', mRNA sequence (1998).

GenBank™ Accession No. AAB92664 for RIG-like 7-1 (1997).

GenBank™ Accession No. AAC02426 for mdkk-1 (1998).

GenBank™ Accession No. AAC02427 for Xdkk-1 (1998).

GenBank™ Accession No. AAD21087 for Sk/Dkk-1 protein precursor (1999).

GenBank™ Accession No. AAD22461 for dickkopf-1 (1999).

GenBank™ Accession No. AAF02674 for dickkopf-1 (1999).

GenBank™ Accession No. AAF02675 for dickkopf-2 (1999).

GenBank™ Accession No. AAF02676 for dickkopf-3 (1999).

GenBank™ Accession No. AAF02677 for dickkopf-4 (1999).

GenBank™ Accession No. AAF02678 for soggy-1 protein (1999).

GenBank™ Accession No. AAF02679 for soggy-1 protein (1999).

GenBank™ Accession No. AAF02680 for Dkk-3 protein (1999).

GenBank™ Accession No. AB003095 for Fruitfly strain SI259 mitochondrial DNA, A+T-rich region, partial sequence (1997).

GenBank™ Accession No. AB003097 for Fruitfly strain g20 mitochondrial DNA, A+T-rich region, partial sequence (1997).

GenBank™ Accession No. AB005216 for *Homo sapiens* mRNA for Nck, Ash and phospholipase C gamma-binding protein NAP4, partial cds (1997).

GenBank™ Accession No. AB017788 for *Homo sapiens* hdkk-4 mRNA, complete cds. (1998).

GenBank™ Accession No. AB018003 for *Homo sapiens* hdkk-4 gene, exon-1, partial sequence (1998).

GenBank™ Accession No. AB018004 for *Homo sapiens* hdkk-4 gene, exon-2 (1998).

GenBank™ Accession No. AB018005 for *Homo sapiens* hdkk-4 gene, exon-3, exon-4 and complete cds. (1998).

GenBank™ Accession No. AB020314 for *Homo sapiens* Dickkopf-1 (hdkk-1-gene, exons, 1st and 2nd coding region (1999).

GenBank™ Accession No. AB020315 for *Homo sapiens* Dickkopf-1 (hdkk-1) gene, 3rd, 4th coding region and complete cds (1999).

GenBank™ Accession No. AB033208 for *Homo sapiens* dickkopf-2 mRNA, complete cds. (1999).

GenBank™ Accession No. AB033421 for *Homo sapiens* dickkopf-3 mRNA, complete cds. (1999).

GenBank™ Accession No. AB035180 for *Homo sapiens* Dickkopf-2 gene, exon (1999).

GenBank™ Accession No. AB035181 for *Homo sapiens* Dickkopf-2 gene, exon and partial cds. (1999).

GenBank™ Accession No. AB035182 for *Homo sapiens* Dickkopf-3 gene, partial cds. (1999).

GenBank™ Accession No. AC000127 for Human Cosmid g1572c198, complete sequence (1997).

GenBank™ Accession No. AC001235 for Human Chromosome 11 pac pDJ360p17; HTGS phase 1, 44 unordered pieces (Apr. 18, 1997).

GenBank™ Accession No. AC003099 for *Homo sapiens* chromosome 4q25, BAC clone B284B3, complete sequence (1997).

GenBank™ Accession No. AF009075 for Hepatitis C virus genomic RNA, 3' nonstranslated region, partial sequence. clone #16 (1997).

GenBank™ Accession No. AF021106 for *Homo sapiens* trinucleotide repeat CTG-11, sequence tagged site (1998).

GenBank™ Accession No. AF030155 for *Drosophila melanogaster* translation initiation factor eIF4G mRNA, complete cds (1998).

GenBank™ Accession No. AF030433 for *Mus musculus* Dickkopf-1 (mdkk-1) mRNA complete cds (1998).

GenBank™ Accession No. AF030434 for *Xenopus laevis* Dickkopf-1 (Xdkk-1) mRNA complete cds (1998).

GenBank™ Accession No. AF034208 for *Homo sapiens* RIG-like 7-1 mRNA, complete cds. (1997).

GenBank™ Accession No. AF052685 for *Homo sapiens* protocadherin 43 gene, exon 3, exon 4, and complete cds. (1998).

GenBank™ Accession No. AF116852 for *Danio rerio* dickkopf-1 (dkk1) mRNA, complete cds. (1999).

GenBank™ Accession No. AF127563 for *Homo sapiens* Sk/Dkk-1 protein precursor, mRNA, complete cds. (1999).

GenBank™ Accession No. AF177394 for *Homo sapiens* dickkopf-1 (DKK-1) mRNA; complete cds. (1999).

GenBank™ Accession No. AF177395 for *Homo sapiens* dickkopf-2 (DKK-2) mRNA, complete cds. (1999).

GenBank™ Accession No. AF177396 for *Homo sapiens* dickkopf-3 (DKK-3) mRNA, complete cds. (1999).

GenBank™ Accession No. AF177397 for *Homo sapiens* dickkopf-4 (DKK-4); mRNA, complete cds. (1999).

GenBank™ Accession No. AF177399 for *Mus musculus* soggy-1 protein (Sgy-1) mRNA, complete cds. (1999).

GenBank™ Accession No. AF177400 for *Mus musculus* Dkk-3 protein (Dkk-3) mRNA, complete cds. (1999).

GenBank™ Accession No. AI004529 Soares_testis_NHT *Homo sapiens* cDNA clone IMAGE:1620926 3', mRNA sequence (1998).

GenBank™ Accession No. AI028601 Soares_testis_NHT *Homo sapiens* cDNA clone IMAGE:1644098 3', mRNA sequence (1998).

GenBank™ Accession No. AI037464 Soares mouse mammary gland NbMMG *Mus musculus* cDNA clone IMAGE:1381445 5" similar to SQ:LFE4_CHICK Q90839 Unknown Lens Fiber Protein CLEFEST4 Precursor, mRNA sequence ( 1998).

GenBank™ Accession No. AI066004 Stratagene mouse testis (#937308) *Mus musculus* cDNA clone IMAGE:515718 5' similar to TR:G517093 G517093 Hypothetical 39.2 kd protein, mRNA sequence (1997).

GenBank™ Accession No. AI074879 for Soares_senescent_fibroblasts_NbHSF *Homo sapiens* cDNA clone IMAGE:1667074 3', mRNA sequence (1998).

GenBank™ Accession No. AI085115 for Soares_senescent_fibroblasts_NbHSF *Homo sapiens* cDNA clone IMAGE:1665669 3', mRNA sequence (1998).

GenBank™ Accession No. AI093106 for Soares_fetal_heart_NbHH19W *Homo sapiens* cDNA clone IMAGE:1694687 3', mRNA sequence (1998).

GenBank™ Accession No. AI095783 for Soares_pregnant_uterus_NbHPU *Homo sapiens* cDNA clone IMAGE:1696830 3', mRNA sequence (1998).

GenBank™ Accession No. AI107210 Stratagene mouse testis (#937308) *Mus musculus* cDNA clone IMAGE:516168 5' similar to TR:G517093 G517093HYPOTHETICAL 39.2 kd protein, mRNA sequence (1998).

GenBank™ Accession No. AI120461 for Soares mouse mammary gland NMLMG *Mus musculus* cDNA clone IMAGE:1383114 5' similar to gb:U11248 *Mus musculus* C57BL/6J ribosomal protein S28 mRNA, complete (MOUSE); mRNA sequence (*Mus musculus*) (1998).

GenBank™ Accession No. AI128249 for Soares_pregnant_uterus NbHPU *Homo sapiens* cDNA clone IMAGE:1711454 3'; mRNA sequence (*Homo sapiens*) (1998).

GenBank™ Accession No. AI129651 for Soares_pregnant_uterus_NbHPU *Homo sapiens* cDNA clone IMAGE:1712938 3', mRNA sequence (*Homo sapiens*) (1998).

GenBank™ Accession No. AI129657 for Soares_pregnant uterus_NbHPU *Homo sapiens* cDNA clone IMAGE:1712950 3', mRNA sequence (*Homo sapiens*) (1998).

GenBank™ Accession No. AI136880 for UI-R-C2p-of-f-01-0-UI. sI UI-R-C2p *Rattus norvegicus* cDNA clone UI-R-C2p-of-f-01-O-UI e', mRNA sequence (*Rattus norvegicus*) (1998).

GenBank™ Accession No. AI138943 Soares_testis_NHT *Homo sapiens* cDNA clone IMAGE:1735666 3', mRNA sequence (1998).

GenBank™ Accession No. AI139919 Soares_testis_NHT *Homo sapiens* cDNA clone IMAGE:1737911 3' similar to SW:LFE4_CHICK Q90839 Unknown Lens Fiber Protein CLEFEST4 Precursor, mRNA sequence (1998).

GenBank™ Accession No. AI146900 for Soares_senescent_fibroblasts_NbHSF *Homo sapiens* cDNA clone IMAGE:1666722 3', mRNA sequence (*Homo sapiens*) (1998).

GenBank™ Accession No. AI150592 Soares_testis_NHT *Homo sapiens* cDNA clone IMAGE:1752164 3', mRNA sequence (1998).
GenBank™ Accession No. AI200822 Soares_testis_NHT *Homo sapiens* cDNA clone IMAGE:1755100 3', mRNA sequence (1998).
GenBank™ Accession No. AI200868 Soares_testis_NHT *Homo sapiens* cDNA clone IMAGE:1754662 3', mRNA sequence (1998).
GenBank™ Accession No. AI201865 for NCI_CGAP_Pr28 *Homo sapiens* cDNA clone IMAGE:1944264 3', mRNA sequence (*Homo sapiens*) (1998).
GenBank™ Accession No. AJ006866 for *Orthochirus scrobiculosus* mRNA for insecticidal toxin, partial (J1998).
GenBank™ Accession No. AJ243963 for *Mus musculus* mRNA for dickkopf-2 (dkk-2 gene) (1999).
GenBank™ Accession No. AJ243964 for *Mus musculus* mRNA for dickkopf-3 (dkk-3 gene) (1999).
GenBank™ Accession No. AU007007 *Schizosaccharomyces pombe* late log phase cDNA *Schizosaccharomyces pombe* cDNA clone spc01322, mRNA sequence (1998).
GenBank™ Accession No. AU007010 *Schizosaccharomyces pombe* late log phase cDNA *Schizosaccharomyces pombe* cDNA clone spc04811, mRNA sequence (1998).
GenBank™ Accession No. AU009349 *Schizosaccharomyces pombe* late log phase cDNA *Schizosaccharomyces pombe* cDNA clone spc01322, mRNA sequence (1998).
GenBank™ Accession No. B24434 for *Arabidopsis thalia* genomic clone F20C17, genomic survey sequence (1997).
GenBank™ Accession No. B39066 for Human Genomic Sperm Library C *Homo sapiens* genomic clone Plate=CT 771 Col=13 Row=C, genomic survey sequence (1997).
GenBank™ Accession No. BAA33475 for hdkk-4 (1999).
GenBank™ Accession No. BAA34651 for homologue of mouse dkk-gene:Acc# AF030433 (1999).
GenBank™ Accession No. BAA85465 for Dickkopf-2 1999).
GenBank™ Accession No. BAA85488 for Dickkopf-3 (1999).
GenBank™ Accession No. BAA87044 for Dickkopf-3 (1999).
GenBank™ Accession No. BAA87056 for Dickkopf-2 (1999).
GenBank™ Accession No. C89869 for *Dictyostelium discoideum* SS (*H. urushihara*) *Dictyostelium discoideum* cDNA clone SSG557, mRNA sequence (1998).
GenBank™ Accession No. CAB60110 dickkopf-2 (1999).
GenBank™ Accession No. CAB60111 for dickopf-3 (1999).
GenBank™ Accession No. D26311 for Chicken mRNA for unknown protein, complete cds (1996).
GenBank™ Accession No. D67096 for Hepatitis C virus genome, 3' terminus (1996).
GenBank™ Accession No. D85016 for Non-A non-B hepatitis virus genomic RNA for 3' UTR (1996).
GenBank™ Accession No. D85017 for Non-A non-B hepatitis virus genomic RNA for 3' UTR (1996).
GenBank™ Accession No. D85020 for Non-A non-B hepatitis virus genomic RNA for 3' UTR (1996).
GenBank™ Accession No. D85021 for Non-A non-B hepatitis virus genomic RNA for 3' UTR (Oct. 8, 1996).
GenBank™ Accession No. D85022 for Non-A non-B hepatitis virus genomic RNA for 3' UTR (1996).
GenBank™ Accession No. D85024 for Non-A non-B hepatitis virus genomic RNA for 3' UTR (1996).
GenBank™ Accession No. D85025 for Non-A non-B hepatitis virus genomic RNA for 3' UTR (1996).
GenBank™ Accession No. F06027 Normalized infant brain cDNA *Homo sapiens* cDNA clone c-0ud06, mRNA sequence (1995).
GenBank™ Accession No. AA073904 for Stratagene mouse heart (#937316) *Mus musculus* cDNA clone 536577 5', mRNA sequence (1997).
GenBank™ Accession No. AA088618 for Soares_pregnant_uterus_NbHPU *Homo sapiens* cDNA clone IMAGE:487642 5', mRNA sequence (1996).
GenBank™ Accession No. AA107210 for Stratagene mouse testic (#937308) *Mus musculus* cDNA clone IMAGE:516168 5' similar to TR:G517093 G517093 Hypothetical 39.2 kd protein; mRNA sequence (1997).

GenBank™ Accession No. AA115249 for Soares_pregnant-uterus-NbHPU *Homo sapiens* cDNA clone IMAGE:501425 3', mRNA sequence (1997).
GenBank™ Accession No. AA115337 for Soares_pregnant_uterus_NbHPU *Homo sapiens* cDNA clone 501425 5', mRNA sequence (1997).
GenBank™ Accession No. AA129488 for Stratagene lung carcinoma 937218 *Homo sapiens* cDNA clone IMAGE:564360 3', mRNA sequence (1997).
GenBank™ Accession No. AA136192 for Soares_pregnant_uterus_NbHPU *Homo sapiens* cDNA clone IMAGE:490113 5', mRNA sequence (1996).
GenBank™ Accession No. AA137219 for Soares_pregnant_uterus_NbHPU *Homo sapiens* cDNA clone IMAGE:490113 3', mRNA sequence (1996).
GenBank™ Accession No. AA143670 for Stratagaene pancreas (#937208) *Homo sapiens* cDNA clone IMAGE:591770 5', mRNA sequence (1996).
GenBank™ Accession No. AA155928 for Stratagene endothelial cell 937223 *Homo sapiens* cDNA clone 590026 5', mRNA sequence (1996).
GenBank™ Accession No. AA207078 for NCI_CGAP_GCB1 *Homo sapiens* cDNA clone IMAGE:682716 5', mRNA sequence (1997).
GenBank™ Accession No. AA209468 for Stratagene hNT neuron (#937233) *Homo sapiens* cDNA clone 648310 3', mRNA sequence (1998).
GenBank™ Accession No. AA220766 for Soares mouse 3NME12 5 *Mus musculus* cDNA clone IMAGE:660068 5', mRNA sequence (1997).
GenBank™ Accession No. AA237194 for Soares mouse NML *Mus musculus* cDNA clone IMAGE:678567 5' similar to gb:U11248 *Mus musculus* C57BL/6J ribosomal protein S28 mRNA, complete (MOUSE), mRNA sequence (1997).
GenBank™ Accession No. AA253446 for Soares_NhHMPu_S1 *Homo sapiens* cDNA clone IMAGE:669375 5', mRNA sequence (1997).
GenBank™ Accession No. AA253464 for Soares_NhHMPu_S1 *Homo sapiens* cDNA clone 669375 3', mRNA sequence (1997).
GenBank™ Accession No. AA259742 for Soares mouse 3NME12 5 *Mus musculus* cDNA clone IMAGE:734543 5' similar to gb:U11248 *Mus musculus* C57BL/6J ribosomal protein S28 mRNA, complete (MOUSE), mRNA sequence (1997).
GenBank™ Accession No. AA265561 for Soares mouse lymph node NbMLN *Mus musculus* cDNA clone 718668 5' similar to TR:G517093 G517093 Hypothetical 39.2 KD Protein; mRNA sequence (1997).
GenBank™ Accession No. AA269333 for Soares mouse 3NME12 5 *Mus musculus* cDNA clone IMAGE:733911 5', mRNA sequence (1997).
GenBank™ Accession No. AA273430 for Soares mouse lymph node NbMLN *Mus musculus* cDNA clone IMAGE:764999 5, mRNA sequence (1997).
GenBank™ Accession No. AA292828 for Soares_testis_NHT *Homo sapiens* cDNA clone IMAGE:727099 5', mRNA sequence (1997).
GenBank™ Accession No. AA304984 for Colon Carcinoma (Caco-2) cell line II *Homo sapiens* cDNA 5' end, mRNA sequence (1997).
GenBank™ Accession No. AA336797 for Enbdometrial tumor *Homo sapiens* cDNA 5' end, mRNA sequence (1997).
GenBank™ Accession No. AA351624 for Infant brain *Homo sapiens* cDNA 5' end similar to RIG, mRNA sequence (1997).
GenBank™ Accession No. AA371363 for Prostate gland I *Homo sapiens* cDNA 5' end, mRNA sequence (1997).
GenBank™ Accession No. AA393069 Soares_testis_NHT *Homo sapiens* cDNA clone IMAGE:727624 5', mRNA sequence (1997).
GenBank™ Accession No. AA397836 for Soares_testis_NHT *Homo sapiens* cDNA clone 728407 5' similar to TR:G517093 G517093 Hypothetical 39.2 KD Protein; mRNA sequence ( 1997).
GenBank™ Accession No. AA402127 Soares_testis_NHT *Homo sapiens* cDNA clone IMAGE:727430 5', mRNA sequence (1997).
GenBank™ Accession No. AA405079 Soares_testis_NHT *Homo sapiens* cDNA clone IMAGE:731664 5', mRNA sequence (1997).

GenBankTM Accession No. AA425947 for Soares_total_fetus_Nb2HF8_9w *Homo sapiens* cDNA clone 760299 3', mRNA sequence (1997).
GenBankTM Accession No. AA426107 Soares_testis_NHT *Homo sapiens* cDNA clone IMAGE:743011 5', mRNA sequence (1997).
GenBankTM Accession No. AA431512 Soares_testis_NHT *Homo sapiens* cDNA clone IMAGE:782156 5', mRNA sequence (1997).
GenBankTM Accession No. AA497850 for Stratagene mouse testis (#937308) *Mus musculus* cDNA clone 917486 5' similar to TR:G517093 G517093 Hypothetical 39.2 KD Protein; mRNA sequence (1997).
GenBankTM Accession No. W61716 for Soares mouse embryo NbME13.5 14.5 *Mus musculus* cDNA clone IMAGE:372542 5' similar to gb:U01317_cds4 Hemoglobin Delta Chain (HUMAN); gb:V00722 Mouse gene for beta-1-globin (MOUSE) (1996).
GenBankTM Accession No. W72126 for Soares_fetal_heart_NbHH19W *Homo sapiens* cDNA clone 345970 3', mRNA sequence (1996).
GenBankTM Accession No. W79975 for Soares mouse embryo NbME13.5 14.5 *Mus musculus* cDNA clone 402616 5', mRNA sequence (1996).
GenBankTM Accession No. X22249 for Human secreted protein gene 39 clone HPMBZ15 (1999).
GenBankTM Accession No. X51459 for Human secreted protein 5' EST SEQ ID No. 38 (1999).
GenBankTM Accession No. X52255 for Protein PRO295 cDNA clone DNA38268-1188 (1999).
GenBankTM Accession No. AA497886 for Stratagene mouse testis (#937308) *Mus musculus* cDNSA clone 917858 5' similar to TR:G517093 G517093 Hypothetical 39.2 KD Protein; mRNA sequence (1997).
GenBankTM Accession No. AA522097 for Barstead mouse proximal colon MPLRB6 *Mus musculus* cDNA clone IMAGE:903996 5' similar to gb:U11248 *Mus musculus* C57BL/6J ribosomal protein S28 mRNA, complete (MOUSE), mRNA sequence (1997).
GenBankTM Accession No. AA528575 for NCI_CGAP_ Kid1 *Homo sapiens* cDNA clone IMAGE:912545 similar to SW: RL37_Human PO2403 60S Ribosomal Protein L37, mRNA sequence (1997).
GenBankTM Accession No. AA538551 for Knowles Solter mouse blastocyst B1 *Mus musculus* cDNA clone IMAGE:932825 5' similar to gb:U11248 *Mus musculus* C57BL/6J ribosomal protein S28 mRNA, complete (MOUSE), mRNA sequence (1997).
GenBankTM Accession No. AA565546 for NCI_CGAP_GC2 *Homo sapiens* cDNA clone IMAGE:1016173 3', mRNA sequence (1997).
GenBankTM Accession No. AA616966 for Barstead mouse proximal colon MPLRB6 *Mus musculus* cDNA clone IMAGE:904368 5', mRNA sequence (1997).
GenBankTM Accession No. AA619642 Knowles Solter mouse blastocyst B1 *Mus musculus* cDNA clone IMAGE:962896 5' similar to TR:G517093 G517093 Hypothetical 39.2 KD Protein, mRNA sequence (1997).
GenBankTM Accession No. AA628979 for Soares testis NHT *Homo sapiens* cDNA clone 743604 3' similar to TR: G517093 G517093 Hypothetical 39.2 KD Protein; mRNA sequence ( 1997).
GenBankTMAccession No. AA641247 for NCI_CGAP_Pr24 *Homo sapiens* cDNA clone IMAGE:1173698 3', mRNA sequence (1997).
GenBankTM Accession No. AA653979 for NCI_CGAP_Pr25 *Homo sapiens* cDNA clone IMAGE:1198589 3', mRNA sequence (1997).
GenBankTM Accession No. AA689611 for Barstead mouse irradiated colon MPLRB7 *Mus musculus* cDNA clone IMAGE:1137654 5', mRNA sequence (1997).
GenBankTM Accession No. AA691908 for Barstead mouse myotubes MPLRB5 *Mus musculus* cDNA clone 1163091 5' similar to gb:U11248 *Mus musculus* C57BL/6J ribosomal S28 mRNA, complete (MOUSE) (1997).
GenBankTM Accession No. AA692959 for Knowles Solter mouse 2 cell *Mus musculus* cDNA clone 1125007 5', mRNA sequence (1997).

GenBankTM Accession No. AA693679 for Soares_fetal_liver_spleen_1NFLS_S1 *Homo sapiens* cDNA clone IMAGE:434242 3', mRNA sequence (1997).
GenBankTM Accession No. AA710868 for Barstead mouse irradiated colon MPLRB7 *Mus musculus* cDNA clone IMAGE:1166873 5', mRNA sequence (1997).
GenBankTM Accession No. AA731642 for NCI_CGAP_GCB1 *Homo sapiens* cDNA clone IMAGE:1251357 3', mRNA sequence (1998).
GenBankTM Accession No. AA741294 for NCI_CGAP_GCB1 *Homo sapiens* cDNA clone IMAGE:1286515 3' similar to SW:ANP2_AUSBR P12101 Antifreeze Peptide AB2. (1), mRNA sequence (1998).
Results of BLASTN Search of GenBankTM Non-Redundant Nucleic Acid Database (nuc) using human CRSP-2 Nucleic Acid Sequence (Feb. 5, 1998).
Results of BLASTN Search of GenBankTM Non-Redundant Nucleic Acid Database (nuc) using human CRSP-3 Nucleic Acid Sequence (Feb. 5, 1998).
Results of BLASTN Search of GenBankTM Non-Redundant Nucleic Acid Database (nuc) using Human CRSP-N Nucleic Acid Sequence (Feb. 5, 1998).
Results of BLASTN Search of GenBankTM Non-Redundant Nucleic Acid Database (nuc) using human CRSP-4 Nucleic Acid Sequence (Feb. 5, 1998).
Results of BLASTX Search of GenBankTM Non-Redundant Protein Database (prot) using human CRSP-2 Nucleic Acid Sequence (Feb. 5, 1998).
Results of BLASTX Search of GenBankTM Non-Redundant Protein Database (prot) using human CRSP-3 Nucleic Acid Sequence (Feb. 5, 1998).
Results of BLASTX Search of GenBankTM Non-Redundant Protein Database (prot) using human CRSP-N Nucleic Acid Sequence (Feb. 5, 1998).
Results of BLASTX Search of GenBankTM Non-Redundant Protein Database (prot) using human CRSP-4 Nucleic Acid Sequence (Feb. 5, 1998).
Sambrook et al., "Molecular Cloning: A Laboratory Manual," Second Edition, vol. 1, 2 & 3 (Cold Spring Harbor Laboratory Press, Cold Spring Harbor, New York, Nov. 1989) p. 9.5.
Sawada, K. et al., "Characterization of termanally differentiated cell state by categorizing cDNA clones derived from chicken lens fibers," Intl. J. Dev. Biol., 40:531-535 (1996).
Schwartz et al., "A superactive insulin: [B10-aspartic acid]insulin(human)," PNAS USA 84:6408-6411 (1987).
Sidman et al., "Controlled Release of Macromolecules and Pharmaceuticals from Synthetic Polypeptides Based on GlutamicAcid", Biopolymers, 22:547-556 (1983).
Soule et al., Cancer Research, 50:6075-6086 (1990).
Tate, G. and T. Mitsuya, "Human Dickkopf as well as DAN Family Members, Cerbeus, and Gremlin, are preferentially expressed in epithelial malignant cell lines," J. Biochem. Mol. Biol. & Biophys., 3:239-242 (1999).
Taurog et al., "HLA-B27 in inbred and non-inbred transgenic mice," J. Immunol., 141:4020 4023 (1988).
Tian, E. et al., "The Role of the Wnt-Signaling Antagonist DKK1 in the Development of Osteolytic Lesions in Multiple Myeloma," New England Journal of Medicine, 349(26):2483 2494 (2003).
Van Tilbeurgh, H. et al., "Colipase: structure and interaction with pancreatic lipase," Biochem. Biophys. Acta, 1441:173-184 (1999).
Wall, "Transgenic Livestock: Progress and Prospects for the Future," Theriogenology, 45:57 68 (1996).
TBLASTN search of human Genbank dbEST from Oct. 15, 1997.
TFASTA search of human Genbank dbEST from Oct. 15, 1997.
Aravind, L. And Koonin, E.V., "A colipase fold in the carboxy-terminal domain of the Wnt antagonists-the Dickkopfs," Curr. Biol., 8(14):R477-8 (1998).
Austin, T.W. et al., "A role for the Wnt gene family in hematopoiesis: Expansion of multilineage progenitor cells," Blood 89(10):3624-3635 (1997).
Ausubel et al., eds, Current Protocols in Molecular Biology, Green Publishers Inc. and Wiley and Sons, NY (1994) (Table of Contents Provided).

Ausubel et al., eds., "Metal-Chelate Affinity Chromatography", Current Protocols in Molecular Biology, Section 10.11.8, John Wiley & Sons, New York (1993).

Barton, "Protein sequence alignment and database scanning," in M.J. E. Sternberg, Ed., Protein Structure Prediction, A Practical Approach, IRL Press, Oxford University Press, Oxford, UK, pp. 31-63 (Jan. 1997).

Bowie et al., "Deciphering the message in protein sequences: tolerance to amino acid substitutions," Science, 247 (4948):1306-1310 1990).

Burgess et al., "Possible dissociation of the heparin-binding and mitogenic activities of heparin-binding (Acidic Fibroblast) growth factor-1 from its receptor-binding activities by site-directed mutagenesis of a single lysine residue," J Cell Biol 111:2129-2138 (1990).

Cadigan, K.M. et al., "Wnt signaling: A common theme in animal development," Genes & Develop., 11:3286-3305 (1997).

Cameron, "Recent Advances in Transgenic Technology," Mol. Biotechnol. 7:253-265 (1997).

Cook, "Scintillation proximity assay: a versatile high-throughput screening technology", Drug Discovery Today, 1: 287-294 (1996).

Daniel, C. et al., "Mapping of linear antigenic sites on the S glycoprotein of a neurotropic murine coronavirus with synthetic peptides: A combination of nine prediction algorithms fails to identify relevant epitopes and peptide immunogenicity is drastically influenced by the nature of the protein carrier," Virology, 202: 540-549, 1994.

Dayhoff et al., Atlas of Protein Sequence and Structure, vol. 5, Supp. 3 (1978) (Table of Contents Provided).

Engels et al., "Gene Synthesis", Angew. Chem. Intl. Ed., 28:716-734 (1989).

Eppstein et al., "Biological activity of liposome-encapsulated murine interferon y is mediated by a cell membrane receptor", Proc. Natl. Acad. Sci. USA, 82:3688-3692 (1985).

Ethier et al., "Insulin like growth factor-I independence in rat mammary carcinoma cells: a dominant phenotype in somatic cell hybrid experiments," Cancer Letters, 74:189-195 (1993).

Fedi, P. et al., "Isolation and biochemical characterization of the human Dkk-1 homologue, a novel inhibitor of mammalian Wnt signaling," J. Biol. Chem., 274(27):19465-19472 (1999).

Finch, P.W. et al., "Purification and molecular cloning of a secreted, Fizzled-related antagonist of Wnt action," Proc. Natl. Acad. Sci. USA, 94(13):6770-6775 (1997).

Francis, "Protein modification and fusion proteins", Focus on Growth Factors, 3:4-10 (1992).

GenBankTM Accession No. AA226979 for Stratagene NT2 neuronal precursor 937230 *Homo sapiens* cDNA clone 663810 5' similar to TR:G517093 G517093 Hypothetical 39.2 KD Protein; mRNA sequence (1998).

GenBankTM Accession No. AA324686 for Cerebellum II *Homo sapiens* cDNA 5' end similar to RIG, mRNA sequence (1997).

GenBankTM Accession No. AA349552 for Infant brain *Homo sapiens* cDNA 5' end similar to RIG, mRNA sequence (1997).

GenBankTM Accession No. AA424460 for Soares_total_fetus_Nb2HF8_9w *Homo sapiens* cDNA clone 760183 5' similar to TR:G517093 G517093 Hypothetical 39.2 KD Protein; mRNA sequence (1997).

GenBankTM Accession No. AA633061 for NCI_CGAP_Thy1 *Homo sapiens* cDNA clone IMAGE:1143486 similar to gb: L06498 40s Ribosomal Protein S20 (HUMAN); mRNA sequence (1997).

GenBankTM Accession No. AA683017 for Stratagene schizo brain s11 *Homo sapiens* cDNA clone 970562 3' similar to TR:G517093 G517093 Hypothetical 39.2 KD Protein; mRNA sequence (1997).

GenBankTMAccession No. AF043208 for *Equus caballus* microsatellite 1CA28 sequence, sequence tagged site (1998).

GenBankTM Accession No. C94299 for *Dictyostelium discoideum* SS (*H. urushihara*) *Dictyostelium discoideum* cDNA clone SSK759, mRNA sequence (1998).

GenBankTM Accession No. D63286 for Clontech human placenta polyA+ mRNA (#6572) *Homo sapiens* cDNA clone GEN-517H04 5', mRNA sequence (1995).

GenBankTM Accession No. R57834 for Fetal heart *Homo sapiens* cDNA clone F5953 5' end, mRNA sequence (1996).

GenBankTM Accession No. R58671 for Fetal heart *Homo sapiens* cDNA clone G4596 5' end, mRNA sequence (1996).

GenBankTM Accession No. T08793 for Infant Brain, Bento Soares *Homo sapiens* cDNA clone HIBBJ81 5' end, mRNA sequence (1993).

GenBankTM Accession No. T30923 for Human Brain *Homo sapiens* DNA 5' end similar to None, mRNA sequence (1995).

GenBankTM Accession No. T31076 for Human Brain *Homo sapiens* cDNA 5' end similar to None, mRNA sequence (1995).

GenBankTM Accession No. 2724106 for RIG-like 7-1 [*Homo sapiens*] (1997).

GenBankTM Accession No. 2736292 for mdkk-1 [*Mus musculus*] (1998).

GenBankTM Accession No. 2736294 for Xdkk-1 [*Xenopus laevis*] (1998).

GenBankTM Accession No. 3660556 for hdkk-4 [*Homo sapiens*] (1998).

GenBankTM Accession No. 3688630 for hdkk-4 [*Homo sapiens*] (1998).

GenBankTM Accession No. A39976 for Sequence 9 from Patent WO942179 (1997).

GenBankTM Accession No. AA 018255 for Soares retina N2b4HR *Homo sapiens* cDNA clone 361535 5', mRNA sequence (1996).

GenBankTM Accession No. AA031969 for Soares_pregnant_uterus_NbHPU *Homo sapiens* cDNA clone 470646 3', mRNA sequence (1996).

GenBankTM Accession No. AA032060 for Soares_pregnant_uterus_NbHPU *Homo sapiens* cDNA clone IMAGE:470646 5', mRNA sequence (Aug. 21, 1996).

GenBankTM Accession No. AA035345 for Soares_pregnant_uterus_NbHPU *Homo sapiens* cDNA clone IMAGE:471479 3', mRNA sequence (1997).

GenBankTM Accession No. AA035443 for Soares_pregnant_uterus_NbHPU *Homo sapiens* cDNA clone IMAGE:471724 3', mRNA sequence (1997).

GenBankTM Accession No. AA035583 for Soares_pregnant_uterus_NbHPU *Homo sapiens* clone IMAGE:471724 5', mRNA sequence (1997).

GenBankTM Accession No. AA037322 for Soares_senescent_fibroblasts_NbHSF *Homo sapiens* cDNA clone 325915 5', mRNA sequence (1996).

GenBankTM Accession No. AA041360 for Soares_fetal_heart_NbHH19W *Homo sapiens* cDNA clone 376472 3', mRNA sequence (1997).

GenBankTM Accession No. AA042806 for Soares_pregnant_uterus_NbHPU *Homo sapiens* cDNA clone IMAGE:486515 3', mRNA sequence (1996).

GenBankTM Accession No. AA043027 for Soares_pregnant_uterus_NbHPU *Homo sapiens* cDNA clone IMAGE:486515 5', mRNA sequence (1996).

GenBankTM Accession No. AA063859 for Stratagene mouse testis (#937309) *Mus musculus* cDNA clone 514640 5' similar to TR:G517093 G517093 Hypothetical 39.2 KD Protein; mRNA sequence (1997).

GenBankTM Accession No. AA065307 for Testis 5 *Homo sapiens* cDNA clone a03500 5' end, mRNA sequence (1996).

GenBankTM Accession No. X56830 for Human phdkk-2 cDNA (1999).

GenBankTM Accession No. X78612 for *G. gallus* genomic DNA repeat region, clone 12F6 (1994).

GenBankTM Accession No. X97746 for Extended human secreted protein coding sequence, SEQ ID No. 311 (1999).

GenBankTM Accession No. Z31224 Mouse testis t-ZAP *Mus musculus* cDNA, mRNA sequence (1995).

George et al., "Current methods in sequence comparison and analysis" in Macromolecular Sequencing and Synthesis Selected Methods and Applications (D.H. Schlesinger, ed., Alan R. Liss, Inc., New York, NY, Mar. 1988) pp. 127-149.

Glinka, A. et al., "Dickkopf-1 is a member of a new family of secreted proteins and functions in head induction," Nature, 391:357-362 (1998).

Grotewold, L. et al., "Expression pattern of Dkk-1 during mouse limb development" Mech. Dev., 89:151-153 (1999).

Grothues et al., "PCR amplification of megabase DNA with tagged random primers (T-PCR)," Nucleic Acids Res. 21 (5):1321-1322 (1993).

Gudas et al., "Nuclear posttranscriptional processing of thymidine kinase mRNA at the onset of DNA synthesis", Proc. Natl. Acad. Sci. USA, 85:4705-4709 (1988).

Henikoff et al., "Amino acid substitution matrices from protein blocks", Proc. Natl. Acad. Sci. USA, 89:10915-10919 (1992).

Houdebine, "Production of pharmaceutical proteins from transgenic animals," J. Biotechnol., 34:269-287 (1994).

Houghten et al., "General method for the rapid solid-phase synthesis of large numbers of peptides: Specificity of antigen-antibody interaction at the level of individual amino acids", Proc Natl Acad. Sci. USA, 82:5131-5135 (1985).

Hunter, "Oncoprotein Networks", Cell, 88:333-346 (1997).

Kappel et al., "Regulating gene expression in transgenic animals," Curr Opin Biotechnol, 3:548-553 (1992).

Kitts et al., "A Method for Producing Recombinant Baculovirus Expression Vectors at High Frequency", Biotechniques, 14:810-817 (1993).

Klein, R.D. et al., "Selection for genes encoding secreted proteins and receptors," Pro. Natl. Acad. Sci. USA, 93:7108-7113 (1996).

Kratzschmar et al., "The human cysteine-rich secretory protein (CRISP) family. Primary structure and tissue distribution of CRISP-1, CRISP-2 and CRISP-3," Eur J Biochem 236:827-836 (1996).

Krupnick, V.E. et al., "Functional and structural diversity of the human Dickkopf gene family," Gene, 238(2):301 313 (1999).

Langer et al., "Biocompatibility of polymeric delivery systems for cacromolecules", J. Biomed. Mater. Res., 15:167-277 (1981).

Langer, "Controlled release of macromolecules", Chem. Tech., 12:98-105 (1982).

Lazar et al., "Transforming growth factor α: mutation of aspartic acid 47 and leucine 48 results in different biological activities," Molecular & Cell Biol 8(3):1247-1252 (1988).

Lee et al., "Dickkopf-1 antagonizes Wnt signaling independent of beta-catenin in human mesothelioma," Biochem Biophys Res Commun 323(4):1246-1250 (2004).

Lennon et al., "The I.M.A.G.E. Consortium: an integrated molecular analysis of genomes and their expression," Genomics, 33(1):151-152 (1996).

Ligon et al., "Differentially expressed gene products in glioblastoma cells suppressed for tumorigenicity", J. NeuroVirology, 4:217-226 (1998).

Ligon, A.H. et al., "Identification of a novel gene product, RIG, that is down-regulated in human glioblastoma," Oncogene, 14(9):1075-1081 (1997).

Lin et al., "Structure-function relationships in glucagon: properties of highly purified Des-His1-, Monoiodo-, and [Des-Asn28,Thr29](homoserine lactone27)-glucagon," Biochemistry 14:1559 1563 (1975).

Lodish, et al, Molecular Cell Biology, 3rd Edition (W.H. Freeman & Co., Mar. 1995), p. 266.

Lucklow et al., "Efficient Generation of Infectious Recombinant Baculoviruses by Site-Specific Transposon-Mediated Insertion of Foreign Genes into a Baculovirus Genome Propagated in *Escherichia coli*", J. Virol., 67:4566-4579 (1993).

Lucklow, "Baculovirus systems for the expression of human gene products", Curr. Opin. Biotechnol., 4:564-572 (1993).

Mao, B. et al., "Kremen2 modulates Dickkopf2 activity during Wnt/LRP6 signaling," Gene, 302:179-183 (2003).

Marston et al., "Solubilization of Protein Aggregates", Meth. Enz., 182:264-275 (1990).

Merrifield et al., "Solid Phase Peptide Synthesis. I. The Synthesis of a Tetrapeptide", J. Am. Chem. Soc., 85:2149 (1963).

Mikheev et al., "A functional genomics approach for the identification of putative tumor suppressor genes: Dickkopf-1 as suppressor of HeLa cell transformation," Carcinogenesis 25(1):47-59 (2004).

Monaghan, A.P. et al., "Dickkopf genes are co-ordinately expressed in mesodermal lineages," Mech. Dev., 87(12):45-56 (1999).

Mullins et al., "Expression of the DBA/2J Ren-2 gene in the adrenal gland of transgenic mice," EMBO J., 8:4065-4072 (1989).

Mullins et al., "Fulminant hypertension in transgenic rats harbouring the mouse Ren-2 gene," Nature, 344:541-544 (1990).

Mullins and Mullins, "Transgenesis in Nonmurine Species," Hypertension, 22:630-633 (1993).

Mullins and Mullins, "Perspectives Series: Molecular medicine in genetically entineered animals. Transgenesis in the rat and larger mammals," J. Clin. Invest. 98:S37-S40 (1996).

Ngo et al., "14. Computational complexity, protein structure prediction, and the levinthal paradox," In: The Protein Folding Problem and Tertiary Structure Prediction, Merz & Le Grand eds., Birkhauser Boston, 1994; pp. 433, 492 495.

Niemann, "Transgenic farm animals get off the ground," Transg. Res., 7:73-75 (1997).

Nusse, R. et al., "Wnt Genes," Cell, 69:1073-1087 (1992).

O'Reilly et al., "Endostatin: An Endogenous Inhibitor of Angiogenesis and Tumor Growth", Cell, 88:277-285 (1997).

Overbeek, "Factors affecting transgenic animal production," in Transgenic Animal Technology, C.A. Pinkert, Ed., Academic Press, Inc. pp. 96-98 (1994).

Parr, B.A. et al., "Wnt genes and vertebrate development," Current Opinion in Genetics and Development, 4:523-528 (1994).

Results of BLASTN Search of GenBankTM Non-Redundant EST Database (dbEST) using human CRSP-2 Nucleic Acid Sequence (Feb. 5, 1998).

Results of BLASTN Search of GenBankTM Non-Redundant EST Database (dbEST) using human CRSP-3 Nucleic Acid Sequence (Feb. 5, 1998).

Results of BLASTN Search of GenBankTM Non-Redundant EST Database (dbEST) using human CRSP-N Nucleic Acid Sequence (Feb. 5, 1998).

Results of BLASTN Search of GenBankTM Non-Redundant EST Database (dbEST) using human CRSP-4 Nucleic Acid Sequence (Feb. 5, 1998).

GenBankTM Accession No. F08729 Normalized infant brain cDNA *Homo sapiens* cDNA clone c-15d12, mRNA sequence (1995).

GenBankTM Accession No. G05905 for human STS WI-6501 (1995).

GenBankTM Accession No. H71273 for Soares fetal liver spleen 1NFLS *Homo sapiens* cDNA clone 229921 5', mRNA sequence (1995).

GenBankTM Accession No. H83446 for Soares melanocyte 2NbHM *Homo sapiens* cDNA clone IMAGE:249345 3', mRNA sequence (1995).

GenBankTM Accession No. H83554 for Soares melanocyte 2NbHM *Homo sapiens* cDNA clone IMAGE:249345 5'; mRNA sequence (1995).

GenBankTM Accession No. H99266 for Soares melanocyte 2NbHM *Homo sapiens* cDNA clone 260362 3', mRNA sequence (1995).

GenBankTM Accession No. I80064 for Sequence 37 from patent US 5708157 (1998).

GenBankTM Accession No. L17318 for *Rattus norvegicus* proline-rich proteoglycan (PRG2) mRNA, complete cds (1993).

GenBankTM Accession No. L47975 *Equus caballus* TATA-box binding protein (TBP) gene, partial cds (1996).

GenBankTM Accession No. L49359 *Homo sapiens* huntingtin gene, partial exon (1996).

GenBankTM Accession No. M29111 for *D. discoideum* actin A-2-sub-2 gene, 5' flank (1990).

GenBankTM Accession No. M29121 for *D. discoideum* actin A-11 gene, 5' flank (1990).

GenBankTM Accession No. M32514 Rat simple sequence DNA, clone 5 (1990).

GenBankTM Accession No. M32515 Rat simple sequence DNA, clone 8 (1990).

GenBankTM Accession No. M36626 Rat simple sequence DNA, clone 5 (1990).

GenBankTM Accession No. M64793 M36414 for Rat salivary proline-rich protein (RP15) gene, complete cds (1991).

GenBankTM Accession No. M95930 for *Manihot esculenta* (clone rubssr37) ribulose-1, 5-bisphosphate caraboxylase/oxygenase small subunit EC 4.1.1.39 (rbc S) mRNA sequence (1992).

GenBankTM Accession No. M98807 for *Xenopus laevis* noggin mRNA, complete cds (1992).

GenBank™ Accession No. N26884 for Soares melanocyte 2NbHM *Homo sapiens* cDNA clone IMAGE:269713 3', mRNA sequence (1995).
GenBank™ Accession No. N94525 for Soares_senescent_fibroblasts_NbHSF *Homo sapiens* cDNA clone 309678 3', mRNA sequence (1996).
GenBank™ Accession No. P18563 for integrin subunit Beta 6 (*Cavia porcellus*) (1999).
GenBank™ Accession No. Q90839 Unknown lens fiber protein CLFEST4 precursor (1997).
GenBank™ Accession No. R14945 for Soares infant brain 1NIB *Homo sapiens* cDNA clone IMAGE:30231 5', mRNA sequence (1995).
GenBank™ Accession No. R27865 for Soares placenta *Homo sapiens* cDNA clone IMAGE:133741 5', mRNA sequence (1995).
GenBank™ Accession No. R32328 for Soares placenta Nb2HP *Homo sapiens* cDNA clone IMAGE:134911 3' similar to gb:X70218 Protein Phosphatase PP-X (HUMAN); contains L1 repetitive element, mRNA sequence (1995).
GenBank™ Accession No. R52311 for Soares infant brain 1NIB *Homo sapiens* cDNA clone IMAGE:39710 5', mRNA sequence (1995).
GenBank™ Accession No. R54473 for Soares infant brain 1NIB *Homo sapiens* cDNA clone IMAGE:39710 3', mRNA sequence (1995).
GenBank™ Accession No. T02494 for Debopam Chakrabarti *Plasmodium falciparum* cDNA clone PF0093C, mRNA sequence (*Plasmodium falciparum*) (1992).
GenBank™ Accession No. U32331 for *Homo sapiens* RIG mRNA, complete cds (1998).
GenBank™ Accession No. U38801 for *Rattus norvegicus* high molecular weight DNA polymerase beta (rnpolb) mRNA, complete cds (1996).
GenBank™ Accession No. U83980 for *Oncorhynchus mykiss* cytochrome c oxidase subunit VIa mRNA, complete cds. (1997).
GenBank™ Accession No. V00185 J01268 for Slime mold (*D. discoideum*) gene for actin 2 sub2 (1989).
GenBank™ Accession No. V38798 for *Homo sapiens* cerebellum and embryo specific protein (1998).
GenBank™ Accession No. W10587 Soares mouse p3NMF 19.5 *Mus musculus* cDNA clone IMAGE:313054 5', mRNA sequence (1997).
GenBank™ Accession No. W30750 for Soares_senescent_fibroblasts_NbHSF *Homo sapiens* cDNA clone IMAGE:309678 5', mRNA sequence (1996).
GenBank™ Accession No. W39572 for Soares_senescent_fibroblasts_NbHSF *Homo sapiens* cDNA clone 322829 5', mRNA sequence (1996).
GenBank™ Accession No. W39690 for Soares_senescent_fibroblasts_NbHSF *Homo sapiens* cDNA clone IMAGE:322977 5', mRNA sequence (1996).
GenBank™ Accession No. W45045 for Soares_senescent_fibroblasts_NbHSF *Homo sapiens* cDNA clone IMAGE:322981 3', mRNA sequence (1996).
GenBank™ Accession No. W45126 for Soares_senescent_fibroblasts_NbHSF *Homo sapiens* cDNA clone 322864 3', mRNA sequence (1996).
GenBank™ Accession No. W46824 for Soares_senescent_fibroblasts_NbHSF *Homo sapiens* cDNA clone IMAGE:324601 3', mRNA sequence (1996).
GenBank™ Accession No. W46873 for Soares_senescent_fibroblasts_NbHSF *Homo sapiens* cDNA clone IMAGE:324601 5', mRNA sequence (1996).
GenBank™ Accession No. W51876 for Soares_senescent_fibroblasts_NbHSF *Homo sapiens* cDNA clone 324400 3', mRNA sequence (1996).
GenBank™ Accession No. W55979 for Soares_senescent_fibroblasts_NBhh19w *Homo sapiens* cDNA clone 340680 5', mRNA sequence (1996).
GenBank™ Accession No. W61032 for Soares_senescent_fibroblasts_NBHSF *Homo sapiens* cDNA clone 326135 5' similar to contains element MER22 repetitive element; mRNA sequence (1996).
Sequence search alignment for SEQ ID No. 1 and 8 (McCarthy) (pp. 1-2), U.S. Appl. No. 10/998,271 PTO 892 form of Feb. 15, 2007.
Sequence search alignment for SEQ ID No. 9 (Eaton et al.) (pp. 1-2), U.S. Appl. No. 10/998,271 PTO 892 form of Feb. 15, 2007.
Sequence search alignment for SEQ ID No. 9 (Soppet) (p. 1), U.S. Appl. No. 10/998,271 PTO 892 form of Feb. 15, 2007.
Stewart and Young, Solid Phase Peptide Synthesis, Pierce Chemical co., Rockford, IL (1984) (Table of Contents Provided).
Gennaro, ed., Remington's Pharmaceutical Sciences, 18th Edition, Mack Publishing Company (1990) (Table of Contents Provided).
Sambrook et al., Molecular Cloning: A Laboratory Manual, Cold Spring Harbor Laboratory Press, Cold Spring Harbor, NY (1989) (Table of Contents Provided).

* cited by examiner

FIG. 1

```
   1  ATGCAGCGGC  TCGGGGGTAT  TTTGCTGTGT  ACACTGCTGG  CGGCGGCGGT
  51  CCCCACTGCT  CCTGCTCCTT  CCCCGACGGT  CACTTGGACT  CCGGCGGAGC
 101  CGGGCCCAGC  TCTCAACTAC  CCTCAGGAGG  AAGCTACGCT  CAATGAGATG
 151  TTTCGAGAGG  TGGAGGAGCT  GATGGAAGAC  ACTCAGCACA  AACTGCGCAG
 201  TGCCGTGGAG  GAGATGGAGG  CGGAAGAAGC  AGCTGCTAAA  ACGTCCTCTG
 251  AGTGAAACCT  GGCAAGCTTA  CCTCCCAACT  ATCACAAATGA  GACCAGCACG
 301  GAGACCAGGG  TGGGAAATAA  CACAGTCCAT  GTGCACCAGG  AAGTTCACAA
 351  GATAACCAAC  AACCAGAGTG  GACAGGTGGT  CTTTTCTGAG  ACAGTCATTA
 401  CATCTGTAGG  GGATGAAGAA  GGCAAGAGGA  GCCATGAAATG  TATCATTGAT
 451  GAAGACTGTG  GGCCCACCAG  GTACTGCCAG  TTCTCCAGCT  TCAAGTACAC
 501  CTGCCAGCCA  TGCCGGGACC  AGCAGATGCT  ATGCACCCGA  GACAGTGAGT
 551  GCTGTGGAGA  CCAGCTGTGT  GCCTGGGGTC  ACTGCACCCA  AAAGGCCACC
 601  AAAGGTGGCA  ATGGACCAT   CTGTGACAAC  CAGAGGGATT  GCCAGCCTGG
 651  CCTGTGTTGT  GCCTTCCAAA  GAGGCCTGCT  GTTCCCCGTG  TGCACACCCC
 701  TGCCCGTGGA  GGGAGAGCTC  TGCCATGACC  CCACCAGCCA  GCTGCTGGAT
 751  CTCATCACCT  GGGAACTGGA  GCCTGAAGGA  GCTTTGGACC  GATGCCCCTG
 801  CGCCAGTGCC  CTCCTATGCC  AGCCACACAG  CCACAGTCTG  GTGTACATGT
 851  GCAAGCCAGC  CTTCGTGGGC  AGCCATGACC  ACAGTGAGGA  GAGCCAGCTG
 901  CCCAGGGAGG  CCCCGGATGA  GTACGAAGAT  GTTGGCTTCA  TAGGGAAGT
 951  GCGCCAGGAG  CTGGAAGACC  TGGAGCGGAG  CCTAGCCCAG  GAGATGGCAT
1001  TTGAGGGGCC  TGCCCCTGTG  GAGTCACTAG  GCGGAGAGGA  GGAGATTTAG
```

FIG. 2

```
   1 ATGCAGCGGC TTGGGGCCAC CCTGCTGTGC CTGCTGCTGG CGGCGGCGGT
  51 CCCCACGGCC CCCGGCCGCC CTCCGACGGC GACCTCGGCT CCAGTCAAGC
 101 CCGGCCCGGC TCTCAGCTAC CCGCAGGAGG AGGCCACCCT CAATGAGATG
 151 TTCCGCGAGG TTGAGAACT GATGGAGGAC ACGCAGCACA AATTGCGCAG
 201 CGCGGTGGAA GAGATGGAGG CAGAAGAAGC TGCTGCTAAA GCATCATCAG
 251 AAGTGAACCT GGCAAACTTA CCTCCCAGCT ATCACAATGA GACCAACACA
 301 GACACGAAGG TTGGAAATAA TACCATCCAT GTGCACCGAG AAATTCACAA
 351 GATAACCAAC AACCAGACTG GACAAATGGT CTTTTCAGAG ACAGTTATCA
 401 CATCTGTGGG AGACGAAGAA GGCAGAAGGA GCCACGAGTG CATCATCGAC
 451 GAGGACTGTG GGCCCAGCAT GTACTGCCAG TTTGCCAGCT TCCAGTACAC
 501 CTGCCAGCCA TGCCGGGGCC AGAGGATGCT CTGCACCCGG GACAGTGAGT
 551 GCTGTGGAGA AACCAGACTG CCAGCTGTGT GTCTGGGGTC ACTGCACCAA AATGGCCACC
 601 AGGGGCAGCA ATGGGACCAT CTGTGACAAC CAGAGGACT GCCAGCCGGG
 651 GCTGTGCTGT GCCTTCCAGA GAGGCCTGCT GTTCCCTGTG TGCACACCCC
 701 TGCCCGTGGA GGGCGAGCTT TGCCATGACC CCGCCAGCCG GCTTCTGGAC
 751 CTCATCACCT GGGAGCTAGA GCCTGATGGA GCCTTGACC GATGCCCTTG
 801 TGCCAGTGCC CTCCTCTGCC AGCCCCACAG CCACAGCCTG GTGTATGTGT
 851 GCAAGCCGAC CTTCGTGGGG AGCCGTGACC AAGATGGGGA GATCCTGCTG
 901 CCCAGAGAGG TCCCCGATGA GTATGAAGTT GGCAGCTTCA TGGAGGAGGT
 951 GCGCCAGGAG CTGGAGGACC TGGAGAGGAG CCTGACTGAA GAGATGGCGC
1001 TGGGGAGCC TGCGGCTGCC GCCGCTGCAC TGCTGGGAGG GGAAGAGATT
1051 TAG
```

FIG. 3

```
1    ATGATGGCTC TGGGCGCAGC GGGAGCTACC CGGGTCTTTG TCGCGATGGT
51   AGCGGCGGCT CTCGGCGGCC ACCCTCTGCT GGGAGTGAGC GCCACCTTGA
101  ACTCGGTTCT CAATTCCAAC GCTATCAAGA ACCTGCCCCC ACCGCTGGGC
151  GGCGCTGCGG GGCACCCAGG CTCTGCAGTC AGCGCCGCGC CGGGAATCCT
201  GTACCCGGGC GGGAATAAGT ACCAGACCAT TGACAACTAC CAGCCGTACC
251  CGTGCGCAGA GGACGAGGAG TGCGGCACTG ATGAGTACTG CGCTAGTCCC
301  ACCCGCGGAG GGGACGCGGG CGTGCAAATC TGTCTCGCCT GCAGGAAGCG
351  CCGAAAACGC TGCATGCGTC ACGCTATGTG CTGCCCCGGG AATTACTGCA
401  AAAATGGAAT ATGTGTGTCT TCTGATCAAA ATCATTTCCG AGGAGAAATT
451  GAGGAAACCA TCACTGAAAG CTTTGGTAAT GATCATAGCA CCTTGGATGG
501  GTATTCCAGA AGAACCACCT TGTCTTCAAA AATGTATCAC ACCAAAGGAC
551  AAGAAGGTTC TGTTTGTCTC CGGTCATCAG ACTGTGCCTC AGGATTGTGT
601  TGTGCTAGAC ACTTCTGGTC CAAGATCTGT AAACCCTGTC TGAAAGAAGG
651  TCAAGTGTGT ACCAAGCATA GGAGAAAAGG CTCTCATGGA CTAGAAATAT
701  TCCAGCGTTG TTACTGTGGA GAAGGTCTGT CTTGCCGGAT ACAGAAAGAT
751  CACCATCAAG CCAGTAATTC TTCTAGGCTT CACACTTGTC AGAGACACTA
801  A
```

FIG. 4

```
  1 ATGGCCGCGC TGATGCGGGT CAAGGATTCA TCCCGCTGCC TTCTCCTACT
 51 GGCCGCGGGTG CTGATGGTGG AGAGCTCACA GCTAGGCAGC TCGGGGCCA
101 AACTCAACTC CATCAAGTCC TCTCTAGGAG GGGAGACTCC TGCTCAGTCA
151 GCCAACCGAT CTGCAGGCAT GAACCAAGGA CTGGCTTTCG GCGGCAGTAA
201 GAAGGGCAAA AGCCTGGGGC AGGCCTACCC TTGCAGCAGT GATAAGGAAT
251 GTGAAGTTGG AAGATACTGC CACAGTCCCC ACCAAGGATC ATCAGCCTGC
301 ATGCTCTGTA GGAGGAAAAA GAAACGATGC CACAGAGATG GGATGTGTTG
351 CCCTGGTACC CGCTGCAATA ATGGAATCTG CATCCCAGTC ACTGAGAGCA
401 TCCTCACCCC ACATATCCCA GCTCTGGATG GCACCCGGCA TAGAGATCGC
451 AACCATGGTC ACTATTCCAA CCATGACCTG GGATGGCAGA ATCTAGGAAG
501 GCCACACTCC AAGATGCCTC ATATAAAAGG ACATGAAGGA GACCCATGCC
551 TACGGTCATC AGACTGCATT GATGGGTTTT GTTGTGCTCG CCACTTCTGG
601 ACCAAAATCT GCAAACCAGT GCTCCATCAG GGGGAAGTCT GTACCAAACA
651 ACGCAAGAAG GGCTGCACG GGCTGGAGAT TTTCCAGAGG TGTGACTGTG
701 CAAAGGGCCT GTCCTGCAAA GTGTGGAAAG ATGCCACCTA CTCTTCCAAA
751 GCCAGACTCC ATGTATGCCA GAAGATCTGA
```

FIG. 5

```
  1 ATGGCCGCGT TGATGCGGAG CAAGGATTCG TCCTGCTGCC TGCTCCTACT
 51 GGCCGCGGTG CTGATGGTGG AGAGCTCACA GATCGGCAGT TCGCGGGCCA
101 AACTCAACTC CATCAAGTCC TCTCTGGGCG GGGAGACGCC TGGTCAGGCC
151 GCCAATCGAT CTGCGGGCAT CTGGCATTCG GCGGCAGTAA
201 GAAGGGCAAA AACCTGGGGC GTACCAAGGA TTGTAGCAGT GATAAGGAGT
251 GTGAAGTTGG GAGGTATTGC AGGCCTACCC ACCAAGGATC ATCGGCCTGC
301 ATGGTGTGTC GGAGAAAAAA CACAGTCCCC CACCGAGATG GCATGTGCTG
351 CCCCAGTACC CGCTGCAATA GAAGCGCTGC TATCCCAGTT ACTGAAAGCA
401 TCTTAACCCC TCACATCCCG ATGGCATCTG GTACTCGGCA CAGAGATCGA
451 AACCACGGTC ATTACTCAAA GCTCTGGATG GGATGGCAGA ATCTAGGAAG
501 ACCACACACT AAGATGTCAC CCATGACTTG GCATGAAGGA GACCCCTGCC
551 TACGATCATC AGACTGCATT ATATAAAAGG GCTGTGCTCG TCATTTCTGG
601 ACCAAAATCT GCAAACCAGT GAAGGGTTTT GGGGAAGTCT GTACCAAACA
651 ACGCAAGAAG GGTTCTCATG GCTGGAAAT TTTCCAGCGT TGCGACTGTG
701 CGAAGGGCCT GTCTTGCAAA GTATGGAAAG ATGCCACCTA CTCCTCCAAA
751 GCCAGACTCC ATGTGTGTCA GAAAATTTGA
```

FIG. 6

```
1    ATGGCCGCGT TGATGCGGAG CAAGGATTCG TCCTGCTGCC TGCTCCTACT
51   GGCCGCGGTG CTGATGGTGG AGAGCTCACA GATCGGCAGT TCGCGGGCCA
101  AACTCAACTC CATCAAGTCC TCTCTGGGCG GGAGACGCCC TGGTCAGGCC
151  GCCAATCGAT CTGCGGGCAT GTACCAAGGA CTGGCATTCG GCGGCAGTAA
201  GAAGGGCAAA AACCTGGGGC AGGCCTACCC TTGTAGCAGT GATAAGGAGT
251  GTGAAGTTGG GAGGTATTGC CACAGTCCCC ACCAAGGATC ATCGGCCTGC
301  ATGGTGTGTC GGAGAAAAAA GAAGCGCTGC CACCGAGATG GCATGTGCTG
351  CCCCAGTACC CGCTGCAATA ATGGGCATGA AGGAGACCCC TGCCTACGAT
401  CATCAGACTG CATTGAAGGG TTTTGCTGTG CTCGTCATTT CTGGACCAAA
451  ATCTGCAAAC CAGTGCTCCA TCAGGGGGAA GTCTGTACCA AACAACGCAA
501  GAAGGGTTCT CATGGGCTGG AAATTTCCA GCGTTGCGAC TGTGCGAAGG
551  GCCTGTCTTG CAAAGTATGG AAAGATGCCA CCTACTCCTC CAAAGCCAGA
601  CTCCATGTGT GTCAGAAAAT TTGA
```

FIG. 7

```
1    ATGGTGGCGG CCGTCCTGCT GGGGCTGAGC TGGCTCTGCT CTCCCCTGGG
51   AGCTCTGGTC CTGGACTTCA ACAACATCAG GAGCTCTGCT GACCTGCATG
101  GGGCCCGGAA GGGCTCACAG TGCCTGTCTG ACACGGACTG CAATACCAGA
151  AAGTTCTGCC TCCAGCCCCG CGATGAGAAG CCGTTCTGTG CTACATGTCG
201  TGGGTTGCGG AGGAGGTGCC AGCGAGATGC CATGTGCTGC CCTGGGACAC
251  TCTGTGTGAA CGATGTTTGT ACTACGATGG AAGATGCAAC CCCAATATTA
301  GAAAGGCAGC TTGATGAGCA AGATGGCACA CATGCAGAAG GAACAACTGG
351  GCACCCAGTC CAGGAAAACC AACCCAAAAG GAAGCCAAGT ATTAAGAAAT
401  CACAAGGCAG GAAGGGACAA GAGGGAGAAA GTTGTCTGAG AACTTTTGAC
451  TGTGGCCCTG GACTTTGCTG TGCTCGTCAT TTTGGACGA AAATTTGTAA
501  GCCAGTCCTT TTGGAGGGAC AGGTCTGCTC CAGAAGAGGG CATAAAGACA
551  CTGCTCAAGC TCCAGAAATC AGGTCTGTT GCGACTGTGG CCCTGGACTA
601  CTGTGTCGAA GCCAATTGAC CAGCAATCGG CAGCATGCTC GATTAAGAGT
651  ATGCCAAAAA ATAGAAAAGC TATAA
```

FIG. 8

```
1   MQRLGGILLC TLLAAAVPTA PAPSPTVTWT PAEPGPALNY PQEEATLNEM
51  FREVEELMED TQHKLRSAVE EMEAEEAAAK TSSEVNLASL PPNYHNETST
101 ETRVGNNTVH VHQEVHKITN NQSGQVVFSE TVITSVGDEE GKRSHECIID
151 EDCGPTRYCQ FSSFKYTCQP CRDQQMLCTR DSECCGDQLC AWGHCTQKAT
201 KGGNGTICDN QRDCQPGLCC AFQRGLLFPV CTPLPVEGEL CHDPTSQLLD
251 LITWELEPEG ALDRCPCASG LLCQPHSHSL VYMCKPAFVG SHDHSEESQL
301 PREAPDEYED VGFIGEVRQE LEDLERSLAQ EMAFEGPAPV ESLGGEEEI*
```

FIG. 9

```
1   MQRIGATLLC LLLAAAVPTA PAPAPTATSA PVKPGPALSY PQEEATLNEM
51  FREVEELMED TQHKLRSAVE EMEAEEAAAK ASSEVNLANL PPSYHNETNT
101 DTKVGNNTIH VHREIHKITN NQTGQMVFSE TVITSVGDEE GRRSHECIID
151 EDCGPSMYCQ FASFQYTCQP CRGQRMLCTR DSECCGDQLC VWGHCTKMAT
201 RGSNGTICDN QRDCQPGLCC AFQRGLLFPV CTPLPVEGEL CHDPASRLLD
251 LITWELEPDG ALDRCPCASG LLCQPHSHSL VYVCKPTFVG SRDQDGEILL
301 PREVPDEYEV GSFMEEVRQE LEDLERSLTE EMALGEPAAA AAALLGGEEI
351 *
```

FIG. 10

```
1   MMALGAAGAT RVFVAMVAAA LGGHPLLGVS ATLNSVLNSN AIKNLPPPLG
51  GAAGHPGSAV SAAPGILYPG GNKYQTIDNY QPYPCAEDEE CGTDEYCASP
101 TRGGDAGVQI CLACRKRRKR CMRHAMCCPG NYCKNGICVS SDQNHFRGEI
151 EETITESFGN DHSTLDGYSR RTTLSSKMYH TKGQEGSVCL RSSDCASGLC
201 CARHFWSKIC KPVLKEGQVC TKHRRKGSHG LEIFQRCYCG EGLSCRIQKD
251 HHQASNSSRL HTCQRH*
```

FIG. 11

```
  1  MAALMRVKDS  SRCLLLLAAV  LMVESSQLGS  SRAKLNSIKS  SLGGETPAQS
 51  ANRSAGMNQG  LAFGGSKKGK  SLGQAYPCSS  DKECEVGRYC  HSPHQGSSAC
101  MLCRRKKKRC  HRDGMCCPGT  RCNNGICIPV  TESILTPHIP  ALDGTRHRDR
151  NHGHYSNHDL  GWQNLGRPHS  KMPHIKGHEG  DPCLRSSDCI  DGFCCARHFW
201  TKICKPVLHQ  GEVCTKQRKK  GSHGLEIFQR  CDCAKGLSCK  VWKDATYSSK
251  ARLHVCQKI*
```

FIG. 12

```
1    MAALMRSKDS SCCLLLLAAV LMVESSQIGS SRAKLNSIKS SLGGETPGQA
51   ANRSAGMYQG LAFGGSKRGK NLGQAYPCSS DKECEVGRYC HSPHQGSSAC
101  MVCRRKKKRC HRDGMCCPST RCNNGICIPV TESILTPHIP ALDGTRHRDR
151  NHGHYSNHDL GWQNLGRPHT RMSHIKGHEG DPCLRSSDCI EGFCCARHFW
201  TKICKPVLHQ GEVCTKQRKK GSHGLEIFQR CDCAKGLSCK VWKDATYSSK
251  ARLHVCQKI*
```

FIG. 13

```
1   MAALMRSKDS SCCLLLLAAV LMVESSQIGS SRAKLNSIKS SLGGETPGQA
51  ANRSAGMYQG LAFGGSKKGK NLGQAYPCSS DKECEVGRYC HSPHQGSSAC
101 MVCRRKKKRC HRDGMCCPST RCNNGHEGDP CLRSSDCIEG FCCARHFWTK
151 ICKPVLHQGE VCTKQRKKGS HGLEIFQRCD CAKGLSCKVW KDATYSSKAR
201 LHVCQKI*
```

FIG. 14

```
1   MVAAVLLGLS WLCSPLGALV LDFNNIRSSA DLHGARKGSQ CLSDTDCNTR
51  KFCLQPRDEK PFCATCRGLR RRCQRDAMCC PGTLCVNDVC TTMEDATPIL
101 ERQLDEQDGT HAEGTTGHPV QENQPKRKPS IKKSQGRKGQ EGESCLRTFD
151 CGPGLCCARH FWTKICKPVL LEGQVCSRRG HKDTAQAPEI FQRCDCGPGL
201 LCRSQLTSNR QHARLRVCQK IEKL*
```

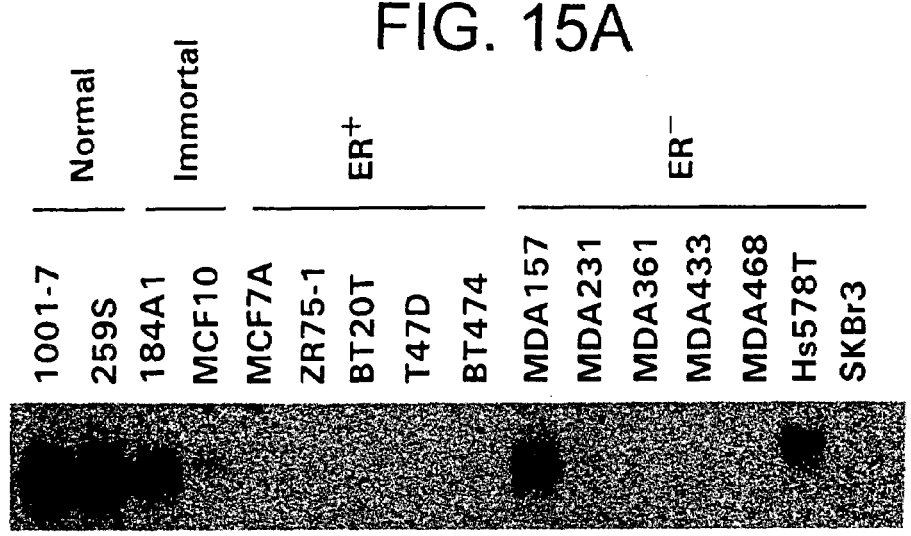
FIG. 15A
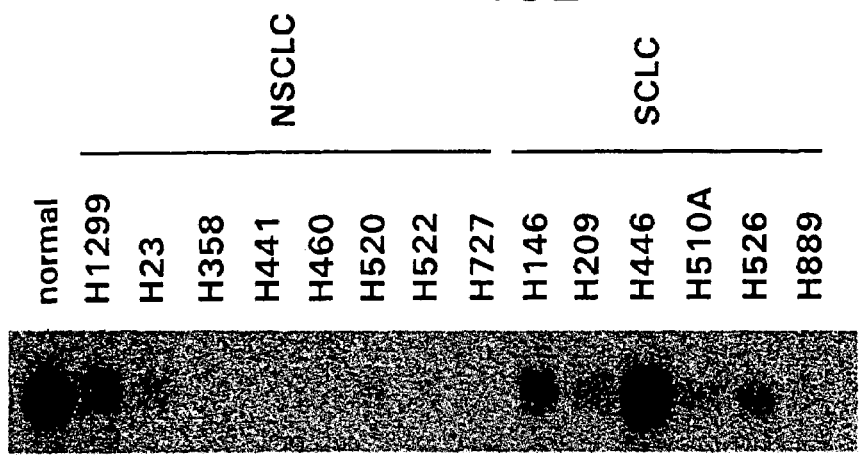
FIG. 15B
FIG. 15C
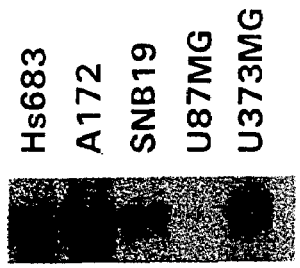
FIG. 15D
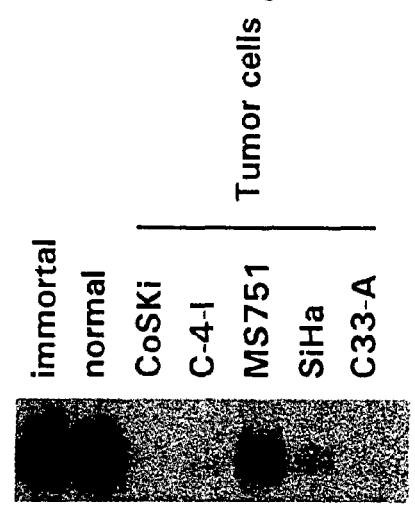

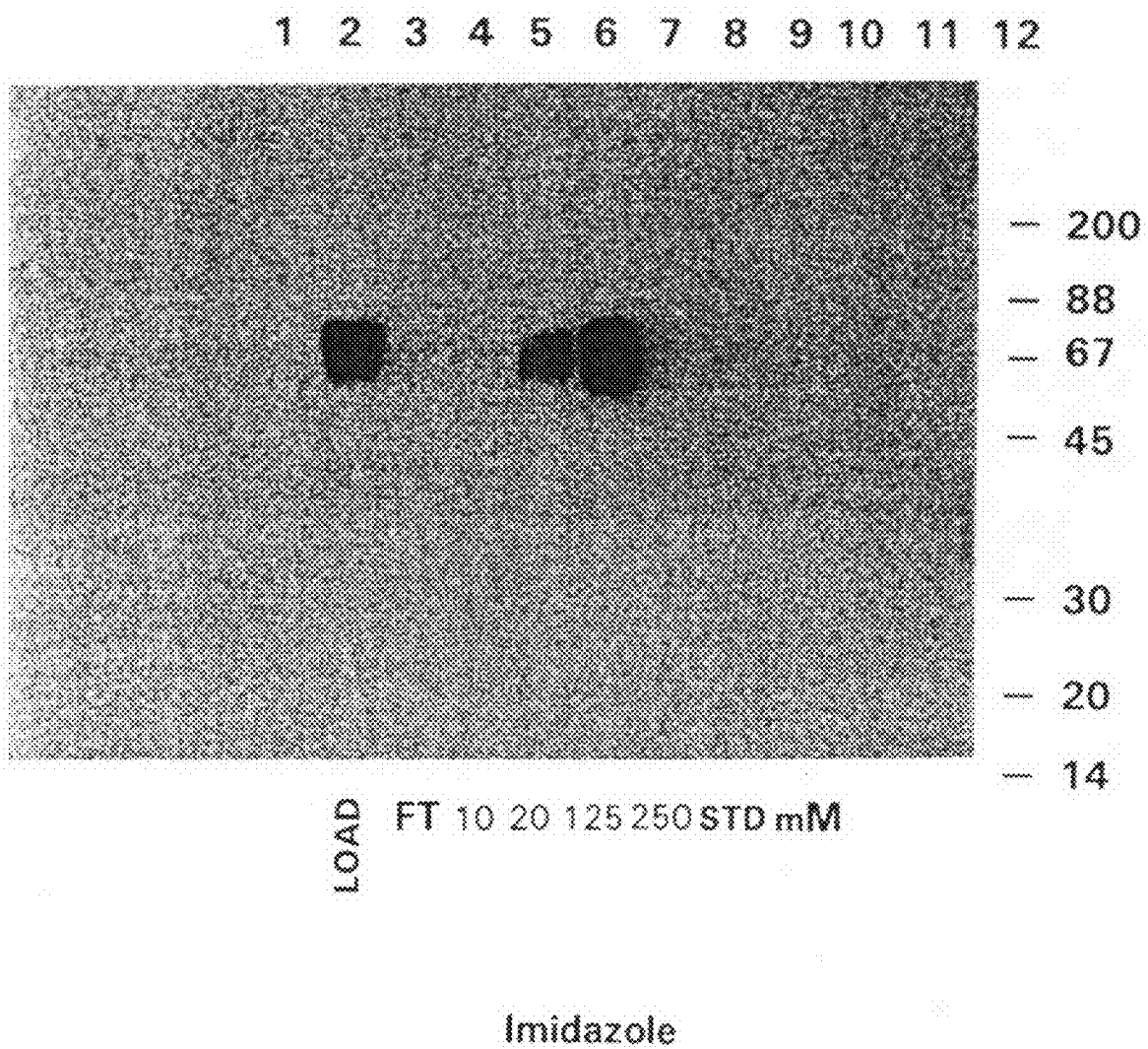

FIG. 22

```
  1  ATGATGGCTC TGGGTGCTGC TGGTGCTACC CGTGTTTTCG TTGCTATGGT
 51  TGCTGCTGCT CTGGGTGGTC ACCCGCTGCT GGGTGTTTCC GCTACCCTGA
101  ACTCCGTTCT GAACTCCAAC GCTATCAAAA ACCTGCCGCC GCCGCTGGGT
151  GGTGCTGCTG GTCACCCGGG TTCCGCTGTT TCCGCTGCTC CGGGTATCCT
201  GTACCCGGGT GGTAACAAAT ACCAGACCAT CGACAACTAC CAGCCGTACC
251  CGTGCGCTGA AGACGAAGAA TGCGGTACCG ACGAATACTG CGCTTCCCCG
301  ACCCGTGGTG GTGACGCTGG TGTTTCAGAT CTGCCTGCTT GCCGTAAACG
351  TCGTAAACGT TGCATGCGTC ACGCTATGTG CTGCCCGGGT AACTACTGCA
401  AAAACGGTAT CTGCGTTTCC TCCGACCAGA ACCACTTCCG TGGTGAAATC
451  GAAGAAACCA TCACCGAATC CTTCGGTAAC GACCACTCCA CCCTGGACGG
501  TTACTCCCGT CGTACCACCC TGTCCTCCAA AATGTACCAC ACCAAAGGTC
551  AGGAAGGTTC CGTTTGCCTG CGTTCCCTCG ACTGCGCTTC CGGTCTGTGC
601  TGCGCTCGTC ACTTCTGGTC CAAAATCTGC AAACCGGTTC TGAAAGAAGG
651  TCAGGTTTGC ACCAAACACC GTCGTAAAGG TTCCCACGGT CTGGAAATCT
701  TCCAGCGGTTG CTACTGCGGT GAAGGTCTGT CCTGCCGTAT CCAGAAAGAC
751  CACCACCAGG CTCCCAACTC CTTCCAACTC CACACCTGCC AGCGTCAC
```

FIG. 23

```
  1  ATGGCTGCTC TGATGGGTTC CAAAGACTCC TCCTGCTGCC TGCTGCTGCT
 51  GGCTGCTGTT CTGATGGTTG AATCCTCCCA GATCGGTTCC TCCCGTGCTA
101  AACTGAACTC CATCAAATCC TCCCTGGGTG GTGAAACCCC GGGTCAGGCT
151  GCTAACCGTT CCGCTGGTAT GTACCAGGGT CTGGCTTTCG GTGGTTCCAA
201  AAAAGGTAAA AACCTGGGTC AGGCTTACCC GTGCTCCTCC GACAAAGAAT
251  GCGAAGTTGG TCGTTACTGC CACTCCCCGC ACCAGGGTTC CTCCGCTTGC
301  ATGGTTTGCC GTCGTAAAAA AAAACGTTGC CACCGTGACG GTATGTGCTG
351  CCCGTCCACC CGTTGCAACA ACGGTATCTG CATCCCGGTT ACCGAATCCA
401  TCCTGACCCC GCACATCCCG GCTCTGGACG GTACCCGTCA CCGTGACCGT
451  AACCACGGTC ACTACTCCAA CCACGACCTG GGTTGGCAGA ACCTGGGTCG
501  TCCGCACACC AAAATGTCCC ACATCAAAGG TCACGAAGGT GACCCGTGCC
551  TGCGTTCCTC CGACTGCATC GAAGGTTTCT GCTGCGCTCG TCACTTCTGG
601  ACCAAAATCT GCAAACCGGT TCTGCACCAG GGTGAAGTTT GCACCAAACA
651  GCGTAAAAAA GGTTCCCACG GTCTGGAAAT CTTCCAGCGT TGGCACTGCG
701  CTAAAGGTCT GTCCTGCAAA GTTTGGAAAG ACGCTACCTA CTCCTCCAAA
751  GCTCGTCTGC ACGTTTGCCA GAAAATC
```

FIG. 24

```
   1 ATGCAGCGTC TGGGTGCTAC CCTGCTGTGC CTGCTGCTGG CTGCTGCTGT
  51 TCCGACCGCT CCGGCTCCGG CTCCGACCGC TACCTCCGCT CCGGTTAAAC
 101 CGGGTCCGGC TCTGTCCTAC CCGCAGGAAG AAGCTACCCT GAACGAAATG
 151 TTCCGTGAAG TTGAAGAACT GATGGAAGAC ACCCAGCACA AACTGCGTTC
 201 CGCTGTTGAA GAAATGGAAG CTGAAGAAGC TGTGCTAAAA GCTTCCTCCG
 251 AAGTTAACCT GGCTAACCTG CCGCCGTCCT ACCACAACGA AACCAACACC
 301 GACACCAAAG TTGGTAACAA CACCATCCAC GTTCACCGTG AAATCCACAA
 351 AATCACCAAC AACCAGACCG GTCAGATGGT TTTCTCCGAA ACCGTTATCA
 401 CCTCCGTTGG TGACGAAGAA GGTCGTCGTT CCCACGAATG CATCATCGAC
 451 GAAGACTGCG GTCCGTCCAT GTACTGCCAG TTCGCTTCCT TCCAGTACAC
 501 CTGCCAGCCG TGCCGTGGTC AGCCGTATGCT GTGCACCCGT GACTCCGAAT
 551 GCTGCGGTGA CCAGTCGGTGA GTTTGGGGTC ACTGCACCAA AATGGCTACC
 601 CGTGGTTCCA ACGGTACCAT CTGCGACAAC CAGCGTGACT GCCAGCCGGG
 651 TCTGTGCTGC GCTTTCCAGC GTGGTCTGCT GTTCCCGGTT GCCACCCCGC
 701 TGCCGGTTGA AGGTGAACTG GCCACGACC CGGCTTCCCG TCTGCTGGAC
 751 CTGATCACCT GGGAACTGGA ACCGGACGGT GCTCTGGACC GTTGCCCGTG
 801 CGCTTCCGGT CTGCGTGCC AGCCGCACTC CCACTCCCTG GTTTACGTTT
 851 GCAAACCGAC CTTCGTTGGT TCCCGTTGACC AGGACGGTGA AATCCTGCTG
 901 CCGCGTGACG TTCCGGACGA ATACGAAGTT GGTTCCTTCA TGGAAGAAGT
 951 TCGTCAGGAA CTGGAAGACC TGGAACGTTC CCTGACCGAA GAAATGGCTC
1001 TGGGTGAACC GCTGCTGCTC TGCTGGGTGG TGAAGAAATC
```

FIG. 25

```
1   ATGGTTGCTG CTGTTCTGCT GGGTCTGTCC TGGCTGTGCT CCCCGCTGGG
51  TGCTCTGGTT CTGGACTTCA ACAACATCCG TTCCTCCGCT GACCTGCACG
101 GTGCTCGTAA AGGTTCCCAG TGCCTGTCCG ACACCGACTG CAACACCCGT
151 AAATTCTGCC TGCAGCCGCG TGACGAAAAA CCGTTCTGCG CTACCTGCCG
201 TGGTCTGCGT CGTCGTTGCC AGCGTGACGC TATGTGCTGC CCGGGTACCC
251 TGTGCGTTAA CGACGTTTGC ACCACCATGG AAGACGCTAC CCCGATCCTG
301 GAACGGTCAGC TGGACGAACA GGACGGGTACC CACGCTGAAG GTACCACCGG
351 TCACCCGGTT CAGGAAAAACC AGCCGAAACG TAAACCGTCC ATCAAAAAAT
401 CCCAGGGTCG TAAAGGTGAAT GAAGGTGAAT CCTGCCTGCG TACCTTCGAC
451 TGCGGGTTCTG GTCTCGTGCTG CGCTCGTCAC TTCTGGACCA AAATCTGCAA
501 ACCGGTTCTG CTGGAAGGTC AGGTTTGCTC CCGTCGTGGT CACAAAGACA
551 CCGCTCAGGC TCCGGAAATC TTCCAGCGTT GCGACTGCGG TCCGGGTCTG
601 CTGTGCCGTT CCCAGCTGAC CTCCAACCGT CAGCACGCTC GTCTGCGTGT
651 TTGCCAGAAA ATCGAAAAAC TG
```

DKR POLYPEPTIDES

This application is a continuation of U.S. Ser. No. 10/998,271, filed Nov. 24, 2004, which is a continuation of U.S. Ser. No. 09/976,736, filed Oct. 9, 2001 (now abandoned), which is a divisional of U.S. Ser. No. 09/161,241, filed Sep. 25, 1998 (now U.S. Pat. No. 6,344,541), which are hereby incorporated by reference.

FIELD OF THE INVENTION

This invention relates generally to novel genes encoding proteins that have use as anti-cancer therapeutics.

BACKGROUND

Related Art

One of the hallmarks of cells that have become cancerous is the change in the gene expression pattern in those cells as compared to normal, non-cancerous cells. An intricate series of cell signaling events leads to this so called "differential gene expression", resulting in conversion of a normal cell to a cancer cell (also known as "oncogenesis" or "cell transformation"). A number of cell signaling pathways have been implicated in the process of cell transformation, such as, for example, the cadherin pathway, the delta/jagged pathway, the hedgehog/sonic hedgehog pathway, and the wnt/wingless pathway (Hunter, *Cell*, 88:333-346 [1997]; Currie, *J. Mol. Med.*, 76:421-433 [1998]; Peifer, *Science*, 275:1752-1753 [1997]. Interestingly, these same pathways are involved in cell morphogenesis, or cell differentiation, during embryo development (Hunter, supra; Cadigan et al., *Genes and Develop.*, 11:3286-3305 [1997]).

The wnt genes encode glycoproteins that are secreted from the cell. These glycoproteins are found in both vertebrate and invertebrate organisms. Currently, there are at least 20 wnt family members, and these members are believed to function variously in control of growth and in tissue differention. Recently, discovery of a novel gene was identified in *Xenopus* and mouse and has been termed dickkopf-1 ("dkk-1"). This gene is purportedly a potent antagonist of wnt-8 signaling (Glinka et al., *Nature*, 391:357-362 [1998]). Interestingly, this gene is also purportedly involved in morphogenesis in the developing embryo (Glinka et al., supra). This gene thus represents a novel growth factor which may be useful in tissue regeneration, and also represents a means for potentially inhibiting cell transformation via wnt signaling.

The Frzb proteins and the protein Cerberus are examples of secreted proteins that purportedly inhibit wnt signaling (Brown, *Curr. Opinion Cell Biol.*, 10:182-187 [1998]).

PCT WO 98/35043, published 13 Aug. 1998 describes human SDF-5 proteins which are purportedly useful in regulating the binding of wnt polypeptides to their receptors.

PCT WO 98/23730, published 4 Jun. 1998, describes transfecting tumors cells with wnt-5a to purportedly decrease tumorigenicity. Wnt-5a purportedly is an antagonist of other wnts.

In view of the devastating effects of cancer, there is a need in the art to identify additional genes that may serve as antagonists of proteins involved in cell transformation.

Accordingly, it is an object of this invention to provide nucleic acid molecules and polypeptides that may be useful as anti-cancer compounds.

It is a further object to provide methods of altering the level of expression and/or activity of such polypeptides in the human body.

Other related objects will readily be apparent from a reading of this disclosure.

SUMMARY OF THE INVENTION

In one embodiment, the present invention provides an isolated nucleic acid molecule encoding a biologically active DKR polypeptide selected from the group consisting of:
 (a) the nucleic acid molecule comprising SEQ ID NO:1;
 (b) the nucleic acid molecule comprising SEQ ID NO:2;
 (c) the nucleic acid molecule comprising SEQ ID NO:3;
 (d) the nucleic acid molecule comprising SEQ ID NO:4;
 (e) the nucleic acid molecule comprising SEQ ID NO:5;
 (f) the nucleic acid molecule comprising SEQ ID NO:6;
 (g) the nucleic acid molecule comprising SEQ ID NO:7;
 (h) the nucleic acid molecule comprising SEQ ID NO:75;
 (i) the nucleic acid molecule comprising SEQ ID NO:76;
 (j) the nucleic acid molecule comprising SEQ ID NO:77;
 (k) the nucleic acid molecule comprising SEQ ID NO:78;
 (l) the nucleic acid molecule encoding the polypeptide of SEQ ID NO:8;
 (m) a nucleic acid molecule encoding the polypeptide of SEQ ID NO:9;
 (n) a nucleic acid molecule encoding the polypeptide of SEQ ID NO:10, or a biologically active fragment thereof;
 (o) a nucleic acid molecule encoding the polypeptide of SEQ ID NO:11, or a biologically active fragment thereof;
 (p) a nucleic acid molecule encoding the polypeptide of SEQ ID NO:12, or a biologically active fragment thereof;
 (q) a nucleic acid molecule encoding the polypeptide of SEQ ID NO:13, or a biologically active fragment thereof;
 (r) a nucleic acid molecule encoding the polypeptide of SEQ ID NO:14, or a biologically active fragment thereof;
 (s) a nucleic acid molecule that encodes a polypeptide that is at least 85 percent identical to the polypeptide of SEQ ID NOs: 10, 11, 12, 13, or 14;
 (t) a nucleic acid molecule that encodes a biologically active DKR polypeptide that has 1-100 amino acid substitutions and/or deletions as compared with the polypeptide of any of SEQ ID NOs:8, 9, 10, 11, 12, 13, or 14; and
 (u) a nucleic acid molecule that hybridizes under conditions of high stringency to any of (c), (d), (e), (f), (g), (h), (i), (k), (l), (m), (n), (o), (p), (q), (r), (s), and (t) above.

In another embodiment, the invention provides an isolated nucleic acid molecule that is the complement of any of the nucleic acid molecules above.

In yet another embodiment, the invention provides an isolated nucleic acid molecule encoding a biologically active DKR polypeptide selected from the group of: amino acids 16-350, 21-350, 22-350, 23-350, 33-350, or 42-350, 21-145, 40-145, 40-150, 45-145, 45-145, 145-290, 150-290, 300-350, or 310-350 of SEQ ID NO:9; amino acids 15-266, 24-266, or 32-266 of SEQ ID NO:10; amino acids 17-259, 26-259, or 34-359 of SEQ ID NO:12; and amino acids 19-224, 20-224, 21-224, or 22-224 of SEQ ID NO:14.

In other embodiments, the invention provides vectors comprising the nucleic acid molecules, and host cells comprising the vectors.

In still another embodiment, the invention provides a process for producing a biologically active DKR polypeptide comprising the steps of:
 (a) expressing a polypeptide encoded by any of the nucleic acid molecules herein in a suitable host; and
 (b) isolating the polypeptide.

In still one other embodiment, the invention provides a biologically active DKR polypeptide selected from the group consisting of:

(a) the polypeptide of SEQ ID NO:8;
(b) the polypeptide of SEQ ID NO:9;
(c) the polypeptide of SEQ ID NO:10;
(d) the polypeptide of SEQ ID NO:11;
(e) the polypeptide of SEQ ID NO:12;
(f) the polypeptide of SEQ ID NO:13;
(g) the polypeptide of SEQ ID NO:14;
(h) a polypeptide that has 1-100 amino acid substitutions or deletions as compared with the polypeptide of any of (a)-(g) above; and
(i) a polypeptide that is at least 85 percent identical to any of the polypeptides of (c)-(h) above.

In still one other embodiment, the invention provides the following polypeptides: a polypeptide that is amino acids 16-350, 21-350, 22-350, 23-350, 33-350, or 42-350, 21-145, 40-145, 40-150, 45-145, 45-145, 145-290, 145-300, 145-350, 150-290, 300-350, or 310-350 of FIG. 9, a polypeptide that is amino acids 15, 266, 24-266, or 32-266 of FIG. 10, a polypeptide that is amino acids 17-259, 26-259, or 34-259 of FIG. 12, and a polypeptide that is amino acids 19-224, 20-224, 21-224, or 22-224 of FIG. 14.

BRIEF DESCRIPTION OF THE DRAWINGS

FIG. 1 (SEQ ID NO:1) depicts the cDNA sequence of mouse DKR-3.

FIG. 2 (SEQ ID NO:2) depicts the cDNA sequence of human DKR-3.

FIG. 3 (SEQ ID NO:3) depicts the DNA sequence of human DKR-1.

FIG. 4 (SEQ ID NO:4) depicts the cDNA sequence of mouse DKR-2.

FIG. 5 (SEQ ID NO:5) depicts the cDNA sequence of human DKR-2.

FIG. 6 (SEQ ID NO:6) depicts the cDNA sequence of human DKR-2a, a splice variant of the DKR-2 gene.

FIG. 7 (SEQ ID NO:7) depicts the cDNA sequence of human DKR-4.

FIG. 8 (SEQ ID NO:8) depicts the amino acid sequence of mouse DKR-3 as translated from the corresponding cDNA.

FIG. 9 (SEQ ID NO:9) depicts the amino acid sequence of human DKR-3 as translated from the corresponding cDNA.

FIG. 10 (SEQ ID NO:10) depicts the amino acid sequence of human DKR-1 as translated from the corresponding cDNA.

FIG. 11 (SEQ ID NO:11) depicts the amino acid sequence of mouse DKR-2 as translated from the corresponding cDNA.

FIG. 12 (SEQ ID NO:12) depicts the amino acid sequence of human DKR-2 as translated from the corresponding cDNA.

FIG. 13 (SEQ ID NO:13) depicts the amino acid sequence of human DKR-2a as translated from the corresponding cDNA.

FIG. 14 (SEQ ID NO:14) depicts the amino acid sequence of human DKR-4 as translated from the corresponding cDNA.

FIGS. 15A-15D are photographs of Northern blots which were probed with human DKR-3. FIG. 15A shows the transcript level of DKR-3 in various human normal (Lanes 1-2) and immortal (Lanes 3-4) cell lines, and in human estrogen receptor plus ("ER+"; Lanes 5-9) and estrogen receptor minus ("ER−"; Lanes 10-16) breast cancer cell lines. FIG. 15B shows the transcript level of human DKR-3 in human normal lung cells (Lane 1), and in various human non-small cell lung cancer ("NSCLC"; Lanes 2-9) and small cell lung cancer ("SCLC"; Lanes 10-15) cell lines. FIG. 15C shows the amount of transcript of human DKR-3 in five glioblastoma cell lines; three of these lines (SNB-19, U-87MG, and U-373MG) are capable of forming tumors in nude mice, while the other two lines (Hs 683 and A 172) are not. FIG. 15D shows the transcript level of human DKR-3 in human immortal (non-cancerous) and normal cervical cells, and in human cervical cancer cell lines (indicated as "tumor cells").

FIG. 21 is a photograph of a Western blot. Contents of the Lanes are indicated in the Examples herein.

FIG. 22 (SEQ ID NO:75) is a nucleic acid sequence of human DKR-1 with codons optimized for expression in *E. coli*.

FIG. 23 (SEQ ID NO:76) is a nucleic acid sequence of human DKR-2 with codons optimized for expression in *E. coli*.

FIG. 24 SEQ ID NO:77) is a nucleic acid sequence of human DKR-3 with codons optimized for expression in *E. coli*.

FIG. 25 (SEQ ID NO:78) is a nucleic acid sequence of human DKR-4 with codons optimized for expression in *E. coli*.

DETAILED DESCRIPTION OF THE INVENTION

Figure 16:
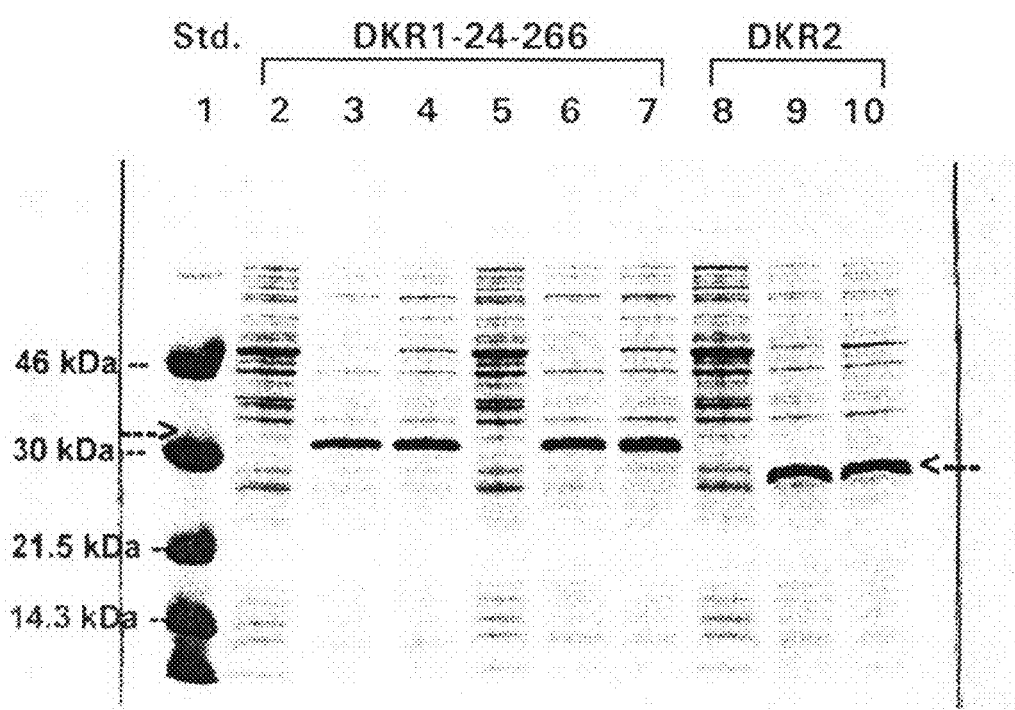
FIG. 16 is a photograph of SDS gel electrophoresis. The contents of the lanes are set forth in the Examples herein.

Included in the scope of this invention are DKR polypeptides such as the polypeptides of SEQ ID NOs:8-14, and related biologically active polypeptide fragments, variants, and derivatives thereof.

Also included within the scope of the present invention are nucleic acid molecules that encode DKR polypeptides such as the nucleic acid molecules of SEQ ID Nos:1-7.

Additionally included within the scope of the present invention are non-human mammals such as mice, rats, rabbits, goats, or sheep in which the gene (or genes) encoding a native DKR polypeptide has (have) been disrupted ("knocked out") such that the level of expression of this gene or genes is (are) significantly decreased or completely abolished. Such mammals may be prepared using techniques and methods such as those described in U.S. Pat. No. 5,557,032. The present invention further includes non-human mammals such as mice, rats, rabbits, goats, or sheep in which the gene (or genes) encoding DKR polypeptides in which either the native form of the gene(s) for that mammal or a heterologous DKR polypeptide gene(s) is (are) over expressed by the mammal, thereby creating a "transgenic" mammal. Such transgenic mammals may be prepared using well known methods such as those described in U.S. Pat. No. 5,489,743 and PCT patent application no. WO94/28122, published 8 Dec. 1994. The present invention further includes non-human mammals in which the promoter for one or more of the DKR polypeptides of the present invention is either activated or inactivated (using homologous recombination methods as described below) to alter the level of expression of one or more of the native DKR polypeptides.

The DKR polypeptides of the present invention are expected to have utility as anti-cancer therapeutics for those cancers such as mammary tumors, stem cell tumors, or other cancers in which the wnt and/or sonic hedgehog (shh) signal transduction pathways are activated. Specific wnt members can transform mammary tissue (Hunter, supra) and are abnormally expressed in many human tumors (Huguet, *Cancer Res.*, 54:2615-2621 [1994]; Dale, *Cancer Res.*, 56:4320-4323 [1996]; see also PCT WO 97/39357). Such activity is expected in view of data presented herein in which the level of DKR-3 transcript is decreased or not detectable at all in many cancer cell lines as compared to similar normal cell lines. Further, such activity is expected in view of the relationship of the genes and polypeptides of the present invention to the gene dickkopf-1 (which, as mentioned above, is purportedly a potent antagonist of wnt-8). DKR-1, a novel gene of the present invention, is a human ortholog of dkk-1. DKR-2, DKR-3, and DKR-4, all novel genes of the present invention, are each related to DKR-1 by their cysteine pattern. In particular, these DKR polypeptides may be of use for treatment of stem cell tumors, mammary tumors, and other cancers in which wnt genes are expressed, and in cancers where wnt and/or shh signaling is activated.

The DKR polypeptides of the present invention may also be administered as agents that can induce and/or enhance tissue differentiation, such as bone formation, cartilage formation, muscle tissue formation, nerve tissue formation, and hematopoietic cell formation. Such activities are expected in view of the fact that a) *Xenopus* dkk-1 purportedly promotes head induction, heart formation, and differentiation or the developing CNS (Glinka, supra); and b) certain wnt polypeptides appear to function in embryo development (Cadigan, *Genes and Devel.*, 11:3286-3305 [1997]), specifically development of the pituitary (Treier, *Genes and Devel.*, 12:1691-1704 [1998]), myogenesis (Munsterberg et al., *Genes and Devel.*, 9:2911-2922 [1995]), osteogenesis (PCT WO 95/17416; PCT WO98/16641), kidney development (Stark et al., *Nature* 372:679-683 [1994]), development of the CNS (Dickinson et al., *Development*, 120:1453-1471 [1994]), and hematopoiesis (PCT WO 98/06747). Thus, addition of certain DKR polypeptides in such cell cultures or tissues may serve to modify the activity of various wnt polypeptides in cellular differentiation processes.

The DKR polypeptides herein may be used in either an in vivo manner or an ex vivo manner for such applications. For example, one or more of the DKR polypeptides of the present invention may be added to a culture of cartilage tissue or nerve tissue, or hematopoietic stem cells, either alone, or in combination with other growth factors and/or other tissue differentiation factors, so as to induce or enhance the regeneration of such tissues. Alternatively, such DKR polypeptides of the present invention may, for example, be injected directly into a joint in need of cartilage, into the spinal cord where the cord has been damaged, into damaged brain tissue, or into bone marrow to enhance hematopoiesis.

The term "DKR polypeptides" as used herein refers to any protein or polypeptide having the properties described herein for DKR polypeptides. The DKR polypeptides may or may not have amino terminal methionines, depending on the manner in which they are prepared. By way of illustration, DKR polypeptides refers to (1) a biologically active polypeptide encoded by any of the DKR polypeptides nucleic acid molecules as defined in any of items (a)-(f) below; (2) naturally occurring allelic variants and synthetic variants of any of DKR polypeptide in which one or more amino acid substitutions, deletions, and/or insertions are present as compared to the DKR polypeptides of SEQ ID NOs:8-14, and/or (3) biologically active polypeptides, or fragments or variants thereof, that have been chemically modified.

As used herein, the term "DKR polypeptide fragment" refers to a peptide or polypeptide that is less than the full length amino acid sequence of a naturally occurring DKR polypeptide but has the biological activity of any of the DKR polypeptides provided herein. Such a fragment may be truncated at the amino terminus, the carboxy terminus, and/or internally (such as by natural splicing), and may be a variant or a derivative of any of the DKR polypeptides. Such DKR polypeptides fragments may be prepared with or without an amino terminal methionine. In addition, DKR polypeptides fragments can be naturally occurring fragments such as DKR polypeptide splice variants (SEQ ID NO:13), other splice variants, and fragments resulting from naturally occurring in vivo protease activity. Preferred DKR polypeptide fragments include amino acids 16-350, 21-350, 22-350, 23-350, 33-350, 42-350, 21-145, 40-145, 40-150, 45-145, 145-290, 145-300, 145-350, 150-290, 300-350, and 310-350, of SEQ ID NO:9; amino acids 15-266, 24-266, or 32-266 of SEQ ID NO:10; amino acids 17-259, 26-259, or 34-359 of SEQ ID NO:12; and amino acids 19-224, 20-224, 21-224, or 22-224 of SEQ ID NO:14.

As used herein, the term "DKR polypeptide variants" refers to DKR polypeptides whose amino acid sequences contain one or more amino acid sequence substitutions, deletions, and/or insertions as compared to the DKR polypeptides amino acid sequences set forth in SEQ ID NOS:8-14. Such DKR polypeptides variants can be prepared from the corresponding DKR polypeptides nucleic acid molecule variants, which have a DNA sequence that varies accordingly from the DNA sequences for wild type DKR polypeptides as set forth in SEQ ID NOS:7-14. Preferred variants of the human DKR polypeptides include alanine substitutions at one or more of amino acid positions. Other preferred substitutions include conservative substitutions at the amino acid positions indicated in the Examples herein, as well as those encoded by DKR nucleic acid molecules as described below.

As used herein, the term "DKR polypeptide derivatives" refers to DKR polypeptides, variants, or fragments thereof, that have been chemically modified, as for example, by addition of one or more polyethylene glycol molecules, sugars, phosphates, and/or other such molecules, where the molecule or molecules are not naturally attached to wild-type DKR polypeptides.

As used herein, the terms "biologically active DKR polypeptides", "biologically active DKR polypeptide fragments", "biologically active DKR polypeptide variants", and "biologically active DKR polypeptide derivatives" refer to DKR polypeptides that have the ability to decrease cancer cell proliferation in the Anchorage Independent Growth Assay of Example 12 herein, or in the In Vivo Tumor Assay of Example 13 herein, or in both assays.

As used herein, the term "DKR polypeptide nucleic acids" when used to describe a nucleic acid molecule refers to a nucleic acid molecule or fragment thereof that (a) has the nucleotide sequence as set forth in any of SEQ ID NOs:1-7; (b) has a nucleic acid sequence encoding a polypeptide that is at least 85 percent identical, but may be greater than 85 percent, i.e., 86, 87, 88, 89, 90, 91, 92, 93, 94, 95, 96, 97, 98, or 99 percent identical to the polypeptide encoded by any of SEQ ID NOS:10-14; (c) is a naturally occurring allelic variant or alternate splice variant of (a) or (b); (d) is a nucleic acid variant of (a)-(c) produced as provided for herein; (e) has a sequence that is complementary to (a)-(d); (f) hybridizes to any of (a)-(e) under conditions of high stringency and/or (g) has a nucleic acid sequence encoding 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or up to 100 amino acid substitutions and/or deletions of any mature DKR polypeptide (i.e., a DKR polypeptide with its endogenous signal peptide removed).

Percent sequence identity can be determined by standard methods that are commonly used to compare the similarity in position of the amino acids of two polypeptides. By way of example, using a computer algorithm such as GAP (Genetic Computer Group, University of Wisconsin, Madison, Wis.), the two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid by the particular comparison matrix) and a gap extension penalty (which is usually 1/10 times the gap opening penalty), as well as a comparison matrix such as PAM 250 or BLOSUM 62 are used in conjunction with the algorithm. A standard comparison matrix (see Dayhoff et al., in: *Atlas of Protein Sequence and Structure*, vol. 5, supp. 3 [1978] for the PAM250 comparison matrix; see Henikoff et al., *Proc. Natl. Acad. Sci. USA*, 89:10915-10919 [1992] for the BLOSUM 62 comparison matrix) is also used by the algorithm. The percent identity is then calculated by the algorithm by determining the percent identity as follows:

$$\frac{\text{Total number of identical matches in the matched span}}{[\text{length of the longer sequence within the matched span}] + [\text{number of gaps introduced into the longer sequence in order to align the two sequences}]} \times 100$$

Polypeptides that are at least 85 percent identical will typically have one or more amino acid substitutions, deletions, and/or insertions as compared with any of the wild type DKR polypeptides. Usually, the substitutions of the native residue will be either alanine, or a conservative amino acid so as to have little or no effect on the overall net charge, polarity, or hydrophobicity of the protein. Conservative substitutions are set forth in Table I below.

TABLE I

Conservative Amino Acid Substitutions

| | |
|---|---|
| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | proline |
| | methionine |
| | leucine |
| | isoleucine |

The term "conditions of high stringency" refers to hybridization and washing under conditions that permit binding of a nucleic acid molecule used for screening, such as an oligonucleotide probe or cDNA molecule probe, to highly homologous sequences. An exemplary high stringency wash solution is 0.2×SSC and 0.1 percent SDS used at a temperature of between 50° C.-65° C.

Where oligonucleotide probes are used to screen cDNA or genomic libraries, one of the following two high stringency solution may be used. The first of these is 6×SSC with 0.05 percent sodium pyrophosphate at a temperature of 35° C.-62° C., depending on the length of the oligonucleotide probe. For example, 14 base pair probes are washed at 35-40° C., 17 base pair probes are washed at 45-50° C., 20 base pair probes are washed at 52-57° C., and 23 base pair probes are washed at 57-63° C. The temperature can be increased 2-3° C. where the background non-specific binding appears high. A second high stringency solution utilizes tetramethylammonium chloride (TMAC) for washing oligonucleotide probes. One stringent washing solution is 3 M TMAC, 50 mM Tris-HCl, pH 8.0, and 0.2 percent SDS. The washing temperature using this solution is a function of the length of the probe. For example, a 17 base pair probe is washed at about 45-50° C.

As used herein, the terms "effective amount" and "therapeutically effective amount" refer to the amount of a DKR polypeptide necessary to support one or more biological activities of the DKR polypeptides as set forth above.

A full-length DKR polypeptide or fragment thereof can be prepared using well known recombinant DNA technology methods such as those set forth in Sambrook et al. (*Molecular Cloning: A Laboratory Manual*, Cold Spring Harbor Laboratory Press, Cold Spring Harbor, N.Y. [1989]) and/or Ausubel et al., eds., (*Current Protocols in Molecular Biology*, Green Publishers Inc. and Wiley and Sons, N.Y. [1994]). A gene or cDNA encoding a DKR polypeptide or fragment thereof may be obtained for example by screening a genomic or cDNA library, or by PCR amplification. Probes or primers useful for screening the library can be generated based on sequence information for other known genes or gene fragments from the same or a related family of genes, such as, for example, conserved motifs found in other DKR polypeptides such as the cysteine pattern. In addition, where a gene encoding DKR polypeptide has been identified from one species, all or a portion of that gene may be used as a probe to identify homologous genes from other species. The probes or primers may be used to screen cDNA libraries from various tissue sources believed to express the DKR gene. Typically, conditions of high stringency will be employed for screening to minimize the number of false positives obtained from the screen.

Another means to prepare a gene encoding a DKR polypeptide or fragment thereof is to employ chemical synthesis using methods well known to the skilled artisan such as those described by Engels et al. (*Angew. Chem. Intl. Ed.*, 28:716-734 [1989]). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the DKR polypeptide will be several hundred nucleotides in length. Nucleic acids larger than about 100 nucleotides can be synthesized as several fragments using these methods. The fragments can then be ligated together to form the full length DKR polypeptide. Usually, the DNA fragment encoding the amino terminus of the polypeptide will have an ATG, which encodes a methionine residue. This methionine may or may not be present on the mature form of the DKR polypeptide, depending on whether the polypeptide produced in the host cell is designed to be secreted from that cell.

In some cases, it may be desirable to prepare nucleic acid and/or amino acid variants of the naturally occurring DKR polypeptides. Nucleic acid variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. Preferred nucleic acid variants are those containing nucleotide substitutions accounting for codon preference in the host cell that is to be used to produce the DKR polypeptide(s). Such "codon optimization" can be determined via computer algorithers which incorporate codon frequency tables such as "Ecohigh. Cod" for codon preference of highly expressed bacterial genes as provided by the University of Wisconsin Package Version 9.0, Genetics Computer Group, Madison, Wis. Other useful codon frequency tables include "Celegans_high.cod", "Celegans_low.cod", "*Drosophila*_high.cod", "Human_high.cod", "Maize_high.cod", and "Yeast_high.cod". Other preferred variants are those encoding conservative amino acid changes as described above (e.g., wherein the charge or polarity of the naturally occurring amino acid side chain is not altered substantially by substitution with a different amino acid) as compared to wild type, and/or those designed to either generate a novel glycosylation and/or phosphorylation site(s), or those designed to delete an existing glycosylation and/or phosphorylation site(s).

The gene, cDNA, or fragment thereof encoding the DKR polypeptide can be inserted into an appropriate expression or amplification vector using standard ligation techniques. The vector is typically selected to be functional in the particular host cell employed (i.e., the vector is compatible with the host cell machinery such that amplification of the gene and/or expression of the gene can occur). The gene, cDNA or fragment thereof encoding the DKR polypeptide may be amplified/expressed in prokaryotic, yeast, insect (baculovirus systems) and/or eukaryotic host cells. Selection of the host cell will depend in part on whether the DKR polypeptide or fragment thereof is to be glycosylated and/or phosphorylated. If so, yeast, insect, or mammalian host cells are preferable.

Typically, the vectors used in any of the host cells will contain 5' flanking sequence (also referred to as a "promoter") and other regulatory elements as well such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below. Optionally, the vector may contain a "tag" sequence, i.e., an oligonucleotide molecule located at the 5' or 3' end of the DKR polypeptide coding sequence; the oligonucleotide molecule encodes polyHis (such as hexaHis), or other "tag" such as FLAG, HA (hemaglutinin Influenza virus) or myc for which commercially available antibodies exist. This tag is typically fused to the polypeptide upon expression of the polypeptide, and can serve as means for affinity purification of the DKR polypeptide from the host cell. Affinity purification can be accomplished, for example, by column chromatography using antibodies against the tag as an affinity matrix. Optionally, the tag can subsequently be removed from the purified DKR polypeptide by various means such as using certain peptidases.

The human immunoglobulin hinge and Fc region could be fused at either the N-terminus or C-terminus of the DKR polypeptides by one skilled in the art. The subsequent Fc-fusion protein could be purified by use of a Protein A affinity column. Fc is known to exhibit a long pharmacokinetic half-life in vivo and proteins fused to Fc have been found to exhibit a substantially greater half-life in vivo than the unfused counterpart. Also, fusion to the Fc region allows for dimerization/multimerization of the molecule that may be useful for the bioactivity of some molecules.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native DKR polypeptides gene 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by, the host cell machinery.

The 5' flanking sequences useful in the vectors of this invention may be obtained by any of several methods well known in the art. Typically, 5' flanking sequences useful herein other than the DKR gene flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose will be readily apparent to one of ordinary skill in the art.

The origin of replication element is typically a part of prokaryotic expression vectors purchased commercially, and aids in the amplification of the vector in a host cell. Amplification of the vector to a certain copy number can, in some cases, be important for optimal expression of the DKR polypeptide. If the vector of choice does not contain an origin of replication site, one may be chemically synthesized based on a known sequence, and ligated into the vector.

The transcription termination element is typically located 3' of the end of the DKR polypeptide coding sequence and serves to terminate transcription of the DKR polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene.

The ribosome binding element, commonly called the Shine-Dalgarno sequence (prokaryotes) or the Kozak sequence (eukaryotes), is usually necessary for translation initiation of mRNA. The element is typically located 3' to the promoter and 5' to the coding sequence of the DKR polypeptide to be synthesized. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

In those cases where it is desirable for DKR polypeptide to be secreted from the host cell, a signal sequence may be used to direct the DKR polypeptide out of the host cell where it is synthesized, and the carboxy-terminal part of the protein may be deleted in order to prevent membrane anchoring. Typically, the signal sequence is positioned in the coding region of the DKR gene or cDNA, or directly at the 5' end of the DKR gene coding region. Many signal sequences have been identified, and any of them that are functional in the selected host cell may be used in conjunction with the DKR gene or cDNA. Therefore, the signal sequence may be homologous or heterologous to the DKR gene or cDNA, and may be homologous or heterologous to the DKR polypeptides gene or cDNA. Additionally, the signal sequence may be chemically synthesized using methods set forth above.

In most cases, secretion of the polypeptide from the host cell via the presence of a signal peptide will result in the removal of the amino terminal methionine from the polypeptide.

In many cases, transcription of the DKR gene or cDNA is increased by the presence of one or more introns in the vector; this is particularly true where the DKR polypeptide is produced in eukaryotic host cells, especially mammalian host cells. The introns used may be naturally occurring within the DKR gene, especially where the gene used is a full length genomic sequence or a fragment thereof. Where the intron is not naturally occurring within the gene (as for most cDNAs), the intron(s) may be obtained from another source. The position of the intron with respect to the 5' flanking sequence and the DKR gene is generally important, as the intron must be transcribed to be effective. As such, where the DKR gene inserted into the expression vector is a cDNA molecule, the preferred position for the intron is 3' to the transcription start site, and 5' to the polyA transcription termination sequence. Preferably for DKR cDNA, the intron or introns will be located on one side or the other (i.e., 5' or 3') of the cDNA such that it does not interrupt the this coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention are typically constructed from a starting vectors such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

Preferred vectors for practicing this invention are those which are compatible with bacterial, insect, and mammalian host cells. Such vectors include, inter alia, pCRII, pCR3, and pcDNA3.1 (Invitrogen Company, San Diego, Calif.), pBSII (Stratagene Company, La Jolla, Calif.), pET15b (Novagen, Madison, Wis.), pGEX (Pharmacia Biotech, Piscataway, N.J.), pEGFP-N2 (Clontech, Palo Alto, Calif.), pETL (BlueBacII; Invitrogen), and pFastBacDual (Gibco/BRL, Grand Island, N.Y.).

After the vector has been constructed and a nucleic acid molecule encoding full length or truncated DKR polypeptide has been inserted into the proper site of the vector, the completed vector may be inserted into a suitable host cell for amplification and/or polypeptide expression.

Host cells may be prokaryotic host cells (such as *E. coli*) or eukaryotic host cells (such as a yeast cell, an insect cell, or a vertebrate cell). The host cell, when cultured under appropriate conditions, can synthesize DKR polypeptide which can subsequently be collected from the culture medium (if the host cell secretes it into the medium) or directly from the host cell producing it (if it is not secreted). After collection, the DKR polypeptide can be purified using methods such as molecular sieve chromatography, affinity chromatography, and the like.

Selection of the host cell for DKR polypeptide production will depend in part on whether the DKR polypeptide is to be glycosylated or phosphorylated (in which case eukaryotic host cells are preferred), and the manner in which the host cell is able to "fold" the protein into its native tertiary structure (e.g., proper orientation of disulfide bridges, etc.) such that biologically active protein is prepared by the DKR polypeptide that has biological activity, the DKR polypeptide may be "folded" after synthesis using appropriate chemical conditions as discussed below.

Suitable cells or cell lines may be mammalian cells, such as Chinese hamster ovary cells (CHO), human embryonic kidney (HEK) 293 or 293T cells, or 3T3 cells. The selection of suitable mammalian host cells and methods for transformation, culture, amplification, screening and product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for expression of the polypeptides of the present invention.

Additionally, where desired, insect cell systems may be utilized in the methods of the present invention. Such systems are described for example in Kitts et al. (*Biotechniques*, 14:810-817 [1993]), Lucklow (*Curr. Opin. Biotechnol.*, 4:564-572 [1993]) and Lucklow et al. (*J. Virol.*, 67:4566-4579 [1993]). Preferred insect cells are Sf-9 and Hi5 (Invitrogen, Carlsbad, Calif.).

Insertion (also referred to as "transformation" or "transfection") of the vector into the selected host cell may be accomplished using such methods as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

The host cells containing the vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of DKR polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If the DKR polypeptide has been designed to be secreted from the host cells, the majority of polypeptide may be found in the cell culture medium. Polypeptides prepared in this way will typically not possess an amino terminal methionine, as it is removed during secretion from the cell. If however, the DKR polypeptide is not secreted from the host cells, it will be present in the cytoplasm and/or the nucleus (for eukaryotic host cells) or in the cytosol (for gram negative bacteria host cells) and may have an amino terminal methionine.

For DKR polypeptide situated in the host cell cytoplasm and/or nucleus, the host cells are typically first disrupted mechanically or with detergent to release the intra-cellular contents into a buffered solution. DKR polypeptide can then be isolated from this solution.

Purification of DKR polypeptide from solution can be accomplished using a variety of techniques. If the polypeptide has been synthesized such that it contains a tag such as Hexahistidine (DKR polypeptide/hexaHis) or other small peptide such as FLAG (Eastman Kodak Co., New Haven, Conn.) or myc (Invitrogen, Carlsbad, Calif.) at either its carboxyl or amino terminus, it may essentially be purified in a one-step process by passing the solution through an affinity column where the column matrix has a high affinity for the tag or for the polypeptide directly (i.e., a monoclonal antibody specifically recognizing DKR polypeptide). For example, polyhistidine binds with great affinity and specificity to nickel, thus an affinity column of nickel (such as the Qiagen® nickel columns) can be used for purification of DKR polypeptide/polyHis. (See for example, Ausubel et al., eds., *Current Protocols in Molecular Biology*, Section 10.11.8, John Wiley & Sons, New York [1993]).

Where the DKR polypeptide is prepared without a tag attached, and no antibodies are available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If it is anticipated that the DKR polypeptide will be found primarily intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If the DKR polypeptide has formed inclusion bodies in the cytosol, the inclusion bodies can often bind to the inner and/or outer cellular membranes and thus will be found primarily in the pellet material after centrifugation. The pellet material can then be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The DKR polypeptide in its now soluble form can then be analyzed using gel electrophoresis, immunoprecipitation or the like. If it is desired to isolate the DKR polypeptide, isolation may be accomplished using standard methods such as those set forth below and in Marston et al. (*Meth. Enz.*, 182:264-275 [1990]). In some cases, the DKR polypeptide may not be biologically active upon isolation. Various methods for "refolding" or converting the polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization but usually at a lower concentration and is not necessarily the same chaotrope as used for the solubilization. In most cases the refolding/oxidation solution will also contain a reducing agent or the reducing agent plus its' oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol (DTT)/dithiane DTT, 2-mercaptoethanol (bME)/dithio-b (ME). In many instances a cosolvent is necessary to increase the efficiency of the refolding and the more common reagents used for this purpose include glycerol, polyethylene glycol of various molecular weights, and arginine.

If DKR polypeptide inclusion bodies are not formed to a significant degree in the host cell, the DKR polypeptide will be found primarily in the supernatant after centrifugation of the cell homogenate, and the DKR polypeptide can be isolated from the supernatant using methods such as those set forth below.

In those situations where it is preferable to partially or completely isolate the DKR polypeptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

In addition to preparing and purifying DKR polypeptide using recombinant DNA techniques, the DKR polypeptides, fragments, and/or derivatives thereof may be prepared by chemical synthesis methods (such as solid phase peptide synthesis) using techniques known in the art such as those set forth by Merrifield et al., (*J. Am. Chem. Soc.*, 85:2149 [1963]), Houghten et al. (*Proc Natl Acad. Sci. USA*, 82:5132 [1985]), and Stewart and Young (Solid Phase Peptide Synthesis, Pierce Chemical Co., Rockford, Ill. [1984]). Such polypeptides may be synthesized with or without a methionine on the amino terminus. Chemically synthesized DKR polypeptides or fragments may be oxidized using methods set forth in these references to form disulfide bridges. The DKR polypeptides or fragments are expected to have biological activity comparable to DKR polypeptides produced recombinantly or purified from natural sources, and thus may be used interchangeably with recombinant or natural DKR polypeptide.

Chemically modified DKR polypeptide compositions in which DKR polypeptide is linked to a polymer are included within the scope of the present invention. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of DKR polypeptide polymers is a mixture of polymers. Preferably, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol.

For the acylation reactions, the polymer(s) selected should have a single reactive ester group. For reductive alkylation, the polymer(s) selected should have a single reactive aldehyde group. A preferred reactive aldehyde is polyethylene glycol propionaldehyde, which is water stable, or mono C1-C10 alkoxy or aryloxy derivatives thereof (see U.S. Pat. No. 5,252,714).

Pegylation of DKR polypeptides may be carried out by any of the pegylation reactions known in the art, as described for example in the following references: *Focus on Growth Factors* 3: 4-10 (1992); EP 0 154 316; and EP 0 401 384. Preferably, the pegylation is carried out via an acylation reaction or an alkylation reaction with a reactive polyethylene glycol molecule (or an analogous reactive water-soluble polymer) as described below.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1-C10) alkoxy- or aryloxy-polyethylene glycol.

In general, chemical derivatization may be performed under any suitable conditions used to react a biologically active substance with an activated polymer molecule. Methods for preparing pegylated DKR polypeptides will generally comprise the steps of (a) reacting the polypeptide with polyethylene glycol (such as a reactive ester or aldehyde derivative of PEG) under conditions whereby DKR polypeptide becomes attached to one or more PEG groups, and (b) obtaining the reaction product(s). In general, the optimal reaction conditions for the acylation reactions will be determined based on known parameters and the desired result. For example, the larger the ratio of PEG:protein, the greater the percentage of poly-pegylated product.

Generally, conditions which may be alleviated or modulated by administration of the present polymer/polypeptides include those described herein for DKR polypeptides molecules. However, the polymer/DKR polypeptides molecules disclosed herein may have additional activities, enhanced or reduced biological activity, or other characteristics, such as increased or decreased half-life, as compared to the non-derivatized molecules.

The DKR polypeptides, fragments thereof, variants, and derivatives, may be employed alone, together, or in combination with other pharmaceutical compositions. The DKR polypeptides, fragments, variants, and derivatives may be used in combination with cytokines, growth factors, antibiotics, anti-inflammatories, and/or chemotherapeutic agents as is appropriate for the indication being treated.

DKR nucleic acid molecules, fragments, and/or derivatives that do not themselves encode polypeptides that are active in activity assays may be useful as hybridization probes in diagnostic assays to test, either qualitatively or quantitatively, for the presence of DKR DNA or corresponding RNA in mammalian tissue or bodily fluid samples.

DKR polypeptide fragments, variants, and/or derivatives that are not themselves active in activity assays may be useful for preparing antibodies that recognize DKR polypeptides.

The DKR polypeptides, fragments, variants, and/or derivatives may be used to prepare antibodies using standard methods. Thus, antibodies that react with the DKR polypeptides, as well as reactive fragments of such antibodies, are also contemplated as within the scope of the present invention. The antibodies may be polyclonal, monoclonal, recombinant, chimeric, single-chain and/or bispecific. Typically, the antibody or fragment thereof will either be of human origin, or will be "humanized", i.e., prepared so as to prevent or minimize an immune reaction to the antibody when administered to a patient. The antibody fragment may be any fragment that is reactive with DKR polypeptides of the present invention, such as, $F_{ab}$, $F_{ab}'$, etc. Also provided by this invention are the hybridomas generated by presenting any DKR polypeptide or fragments thereof as an antigen to a selected mammal, followed by fusing cells (e.g., spleen cells) of the mammal with certain cancer cells to create immortalized cell lines by known techniques. The methods employed to generate such cell lines and antibodies directed against all or portions of a human DKR polypeptide of the present invention are also encompassed by this invention.

The antibodies may be used therapeutically, such as to inhibit binding of the DKR polypeptide to its binding partner. The antibodies may further be used for in vivo and in vitro diagnostic purposes, such as in labeled form to detect the presence of DKR polypeptide in a body fluid or cell sample.

Preferred antibodies are human antibodies, either polyclonal or monoclonal.

Therapeutic Compositions and Administration

Therapeutic compositions of DKR polypeptides are within the scope of the present invention. Such compositions may comprise a therapeutically effective amount of the polypeptide or fragments, variants, or derivatives in admixture with a pharmaceutically acceptable carrier. The carrier material may be water for injection, preferably supplemented with other materials common in solutions for administration to mammals. Typically, a DKR polypeptide therapeutic compound will be administered in the form of a composition comprising purified polypeptide, fragment, variant, or derivative in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Other exemplary compositions comprise Tris buffer of about pH 7.0-8.5, or acetate buffer of about pH 4.0-5.5, which may further include sorbitol or a suitable substitute therefor.

The DKR polypeptide compositions can be administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

Therapeutic formulations of DKR polypeptide compositions useful for practicing the present invention may be prepared for storage by mixing the selected composition having the desired degree of purity with optional physiologically acceptable carriers, excipients, or stabilizers (*Remington's Pharmaceutical Sciences,* 18th Edition, A. R. Gennaro, ed., Mack Publishing Company [1990]) in the form of a lyophilized cake or an aqueous solution. Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

An effective amount of the DKR polypeptide composition(s) to be employed therapeutically will depend, for example, upon the therapeutic objectives such as the indication for which the DKR polypeptide is being used, the route of administration, and the condition of the patient. Accordingly, it will be necessary for the therapist to titer the dosage and modify the route of administration as required to obtain the optimal therapeutic effect. A typical daily dosage may range from about 0.1 µg/kg to up to 100 mg/kg or more, depending on the factors mentioned above. Typically, a clinician will administer the composition until a dosage is reached that achieves the desired effect. The composition may therefore be administered as a single dose, or as two or more doses (which may or may not contain the same amount of DKR polypeptide) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing.

The DKR polypeptide composition to be used for in vivo administration must be sterile. This is readily accomplished by filtration through sterile filtration membranes. Where the composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

The route of administration of the composition is in accord with known methods, e.g. oral, injection or infusion by intravenous, intraperitoneal, intracerebral (intraparenchymal), intracerebroventricular, intramuscular, intraocular, intraarterial, or intralesional routes, or by sustained release systems or implantation device which may optionally involve the use of a catheter. Where desired, the compositions may be administered continuously by infusion, bolus injection or by implantation device.

Alternatively or additionally, the composition may be administered locally via implantation into the affected area of a membrane, sponge, or other appropriate material on to which DKR polypeptide has been absorbed.

Where an implantation device is used, the device may be implanted into any suitable tissue or organ, and delivery of DKR polypeptide may be directly through the device via bolus, or via continuous administration, or via catheter using continuous infusion.

DKR polypeptide may be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers,* 22: 547-556 [1983]), poly(2-hydroxyethyl-methacrylate) (Langer et al., *J. Biomed.*

*Mater. Res.*, 15: 167-277 [1981] and Langer, *Chem. Tech.*, 12: 98-105 [1982]), ethylene vinyl acetate (Langer et al., supra) or poly-D(-)-3-hydroxybutyric acid (EP 133,988). Sustained-release compositions also may include liposomes, which can be prepared by any of several methods known in the art (e.g., Eppstein et al., *Proc. Natl. Acad. Sci. USA*, 82: 3688-3692 [1985]; EP 36,676; EP 88,046; EP 143,949).

In some cases, it may be desirable to use DKR polypeptide compositions in an ex vivo manner. Here, cells, tissues, or organs that have been removed from the patient are exposed to DKR polypeptide compositions after which the cells, tissues and/or organs are subsequently implanted back into the patient.

In other cases, DKR polypeptide may be delivered through implanting into patients certain cells that have been genetically engineered, using methods such as those described herein, to express and secrete the polypeptides, fragments, variants, or derivatives. Such cells may be animal or human cells, and may be derived from the patient's own tissue or from another source, either human or non-human. Optionally, the cells may be immortalized. However, in order to decrease the chance of an immunological response, it is preferred that the cells be encapsulated to avoid infiltration of surrounding tissues. The encapsulation materials are typically biocompatible, semi-permeable polymeric enclosures or membranes that allow release of the protein product(s) but prevent destruction of the cells by the patient's immune system or by other detrimental factors from the surrounding tissues.

Methods used for membrane encapsulation of cells are familiar to the skilled artisan, and preparation of encapsulated cells and their implantation in patients may be accomplished without undue experimentation. See, e.g., U.S. Pat. Nos. 4,892,538; 5,011,472; and 5,106,627. A system for encapsulating living cells is described in PCT WO 91/10425 (Aebischer et al.). Techniques for formulating a variety of other sustained or controlled delivery means, such as liposome carriers, bio-erodible particles or beads, are also known to those in the art, and are described, for example, in U.S. Pat. No. 5,653,975 (Baetge et al., CytoTherapeutics, Inc.). The cells, with or without encapsulation, may be implanted into suitable body tissues or organs of the patient.

As discussed above, it may be desirable to treat isolated cell populations such as stem cells, lymphocytes, red blood cells, chondrocytes, neurons, and the like with one or more DKR polypeptides, variants, derivatives and/or fragments. This can be accomplished by exposing the isolated cells to the polypeptide, variant, derivative, or fragment directly, where it is in a form that is permeable to the cell membrane. Alternatively, gene therapy can be employed as described below.

One manner in which gene therapy can be applied is to use the DKR gene (either genomic DNA, cDNA, and/or synthetic DNA encoding a DKR polypeptide, or a fragment, variant, or derivative thereof) which may be operably linked to a constitutive or inducible promoter to form a "gene therapy DNA construct". The promoter may be homologous or heterologous to the endogenous DKR gene, provided that it is active in the cell or tissue type into which the construct will be inserted. Other components of the gene therapy DNA construct may optionally include, as required, DNA molecules designed for site-specific integration (e.g., endogenous flanking sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell specific binding agents (as, for example, for cell targeting) cell-specific internalization factors, and transcription factors to enhance expression by a vector as well as factors to enable vector manufacture.

This gene therapy DNA construct can then be introduced into the patient's cells (either ex vivo or in vivo). One means for introducing the gene therapy DNA construct is via viral vectors. Suitable viral vectors typically used in gene therapy for delivery of gene therapy DNA constructs include, without limitation, adenovirus, adeno-associated virus, herpes simplex virus, lentivirus, papilloma virus, and retrovirus vectors. Some of these vectors, such as retroviral vectors, will deliver the gene therapy DNA construct to the chromosomal DNA of the patient's cells, and the gene therapy DNA construct can integrate into the chromosomal DNA; other vectors will function as episomes and the gene therapy DNA construct will remain in the cytoplasm. The use of gene therapy vectors is described, for example, in U.S. Pat. Nos. 5,672,344 (30 Sep. 1997; Kelly et al., University of Michigan), 5,399,346 (21 Mar. 1995; Anderson et al., U.S Dept. Health and Human Services), 5,631,236 (20 May 1997; Woo et al., Baylor College of Medicine), and 5,635,399 (3 Jun. 1997; Kriegler et al., Chiron Corp.).

Alternative means to deliver gene therapy DNA constructs to a patient's cells without the use of viral vectors include, without limitation, liposome-mediated transfer, direct injection of naked DNA, receptor-mediated transfer (ligand-DNA complex), electroporation, calcium phosphate precipitation, and microparticle bombardment (e.g., "gene gun"). See U.S. Pat. Nos. 4,970,154 (13 Nov. 1990; Chang, Baylor College of Medicine), WO 96/40958 (19 Dec. 1996; Smith et al., Baylor College of Medicine) 5,679,559 (21 Oct. 1997; Kim et al., University of Utah) 5,676,954 (14 Oct. 1997; Brigham, Vanderbilt University), and 5,593,875 (14 Jan. 1997; Wurm et al., Genentech).

Another means to increase endogenous DKR polypeptide expression in a cell via gene therapy is to insert one or more enhancer elements into the DKR polypeptide promoter, where the enhancer element(s) can serve to increase transcriptional activity of the DKR polypeptides gene. The enhancer element(s) used will be selected based on the tissue in which one desires to activate the gene(s); enhancer elements known to confer promoter activation in that tissue will be selected. For example, if a DKR polypeptide is to be "turned on" in T-cells, the lck promoter enhancer element may be used. Here, the functional portion of the transcriptional element to be added may be inserted into a fragment of DNA containing the DKR polypeptide promoter (and optionally, vector, 5' and/or 3' flanking sequence, etc.) using standard cloning techniques. This construct, known as a "homologous recombination construct" can then be introduced into the desired cells either ex vivo or in vivo.

Gene therapy can be used to decrease DKR polypeptide expression by modifying the nucleotide sequence of the endogenous promoter(s). Such modification is typically accomplished via homologous recombination methods. For example, a DNA molecule containing all or a portion of the promoter of the DKR gene(s) selected for inactivation can be engineered to remove and/or replace pieces of the promoter that regulate transcription. Here, the TATA box and/or the binding site of a transcriptional activator of the promoter may be deleted using standard molecular biology techniques; such deletion can inhibit promoter activity thereby repressing transcription of the corresponding DKR gene. Deletion of the TATA box or transcription activator binding site in the promoter may be accomplished by generating a DNA construct comprising all or the relevant portion of the DKR polypeptide promoter(s) (from the same or a related species as the DKR gene(s) to be regulated) in which one or more of the TATA box and/or transcriptional activator binding site nucleotides are mutated via substitution, deletion and/or insertion of one or more nucleotides such that the TATA box and/or activator binding site has decreased activity or is rendered completely inactive. This construct, which also will typically contain at least about 500 bases of DNA that correspond to the native (endogenous) 5' and 3' flanking regions of the promoter segment that has been modified, may be introduced into the appropriate cells (either ex vivo or in vivo) either directly or via a viral vector as described above. Typically, integration of the construct into the genomic DNA of the cells will be via homologous recombination, where the 5' and 3' flanking DNA sequences in the promoter construct can serve to help integrate the modified promoter region via hybridization to the endogenous chromosomal DNA.

Other gene therapy methods may also be employed where it is desirable to inhibit one or more DKR polypeptides. For example, antisense DNA or RNA molecules, which have a sequence that is complementary to at least a portion of the selected DKR polypeptide gene(s) can be introduced into the cell. Typically, each such antisense molecule will be complementary to the start site (5' end) of each selected DKR gene. When the antisense molecule then hybridizes to the corresponding DKR polypeptides mRNA, translation of this mRNA is prevented.

Alternatively, gene therapy may be employed to create a dominant-negative inhibitor of one or more of the DKR polypeptides. In this situation, the DNA encoding a mutant full length or truncated polypeptide of each selected DKR polypeptide can be prepared and introduced into the cells of a patient using either viral or non-viral methods as described above. Each such mutant is typically designed to compete with endogenous polypeptide in its biological role.

Samples of the E. coli cell lines GM121 and GM94 have been deposited with the American Type Culture Collection, 10801 University Blvd., Manassas, Va., USA on DATE as accession numbers X and Y, respectively.

The following examples are intended for illustration purposes only, and should not be construed as limiting the scope of the invention in any way.

EXAMPLES

Example 1

Cloning of the Mouse DKR-3 Gene

About 120 adult mice with an average body weight of about 18 grams were each injected intraperitoneally with a kainate solution (prepared as a stock solution of about 1 mg/ml kainate in sterile PBS) at a dose of about 25 mg kainate per kilogram body weight. About six hours after injection, the mice were sacrificed, and the hippocampus was dissected from each mouse. Total RNA was extracted from hippocampal tissue using the Trizol method (Gibco BRL, Grand Island, N.Y.). The poly(A+) mRNA fraction was isolated from total RNA using Message Maker (Gibco BRL, Grand Island, N.Y.) according to the manufacturer's recommended procedure. Hippocampal tissue was also obtained from control mice (which received an injection of PBS only), and poly(a+) mRNA was obtained from this tissue as well using the same procedures.

Two random primed cDNA libraries were prepared; one from the kainate-treated and one from the control poly (A+) mRNA using the Superscript® plasmid system (Gibco BRL, Gaithersburg, Md.). A random cDNA primer containing an internal NotI restriction site was used to initiate first strand synthesis and had the following sequence:

(SEQ ID NO:15)
GGAAGGAAAAAAGCGGCCGCAACANNNNNNNNNN where N is A, G, C, or T.

Both first strand cDNA synthesis and second strand cDNA synthesis were performed according to the manufacturer's recommended protocol. After second strand synthesis, the reaction products were extracted with phenol:chloroform: isoamyl alcohol (in a volume ratio of 25:24:1), followed by ethanol precipitation. The double strand cDNA products were ligated using standard ligation procedures to the following double stranded oligonucleotide adapter (obtained from Gibco BRL, Grand Island, N.Y.):

(SEQ ID NO:16)
TCGACCCACGCGTCCG (SEQ ID NO:17)
GGGTGCGCAGGC

After ligation, the cDNA was digested to completion with NotI, and size fractionated on a 1 percent agarose gel. The cDNA products between about 250 and 800 base pairs were selected and purified from the gel using the Qiagen® gel extraction kit (Qiagen, Chatsworth, Calif.). The purified cDNA products were directionally ligated into the vector pYY41L (American Type Culture Collection, "ATCC"; 10801 University Blvd., Manassas, Va., USA; accession number 209636) which had been previously digested with NotI and SalI. The ligated cDNA was then introduced into electrocompetent ElectroMax® DH108 E. coli cells (Gibco-BRL, Grand Island, N.Y.) via standard electroporation techniques. The library was then titered by a serial dilution of the transformation cell mixture.

About one million primary clones were divided into 20 pools (50,000 clones each pool) and each pool was plated on 245 mm×245 mm square plate containing MR2001 medium (MacConnel Research, San Diego, Calif.) and about 60 ug/ml carbonocillin. After incubation overnight at 37 C, the colonies were scraped off the plate in about 20 ml SOC (SOC contains about 2 percent Bactotryptone, 0.5 percent yeast extract, 10 mM sodium chloride, 2.5 mM potassium chloride, and 10 mM magnesium sulfate) and were pelleted by centrifugation at about 6000 rpm for about 10 minutes. The plasmids were then recovered from the cells using Qiagen® maxi prep columns (Qiagen, Chatsworth, Calif.) according to the protocol suggested by the manufacturer.

About two hundred and fifty thousand clones (50 ug total plasmids/10 ug from each pool) were used to transform yeast strain YPH499 (ATCC accession number 90834) and an amylase-based signal trap assay was conducted as follows (see co-pending U.S. Ser. No. 09/026,959 filed 20 Feb. 1998 for a detailed description of this technique). Around 1000 transformants were plated on a single starch-containing selection plate (15 cm diameter with a medium containing about 0.6 percent yeast nitrogen base, 2 percent glucose, 0.1 percent CAA, 1.0× trp dropout solution, 0.7 percent potato starch azure, and 1.5 percent agarose). The plates were incubated at about 30 C for 4-5 days until full development of halos was observed. The colonies in the center of the halo were picked and restreaked on a fresh plate to form single colonies. The single colonies with halos were then picked and arrayed into 96 well microtiter plates containing about 100 ul of water per well, thereby generating the "yeast colony solutions".

About ten microliters of each well of each yeast colony solution was used as template to recover the cDNA fragment from that colony through PCR. Therefore, ninety-six PCR reactions were independently performed using PCR-Ready Beads® (96 well format, Amersham-Pharmacia Biotech, Pistcataway, N.J.) and the following oligonucleotides according to the manufacturer's protocol:

ACTAGCTCCAGTGATCTC (SEQ ID NO:18)

CGTCATTGTTCTCGTTCC (SEQ ID NO:19)

PCR was conducted using a Perkin-Elmer 9600 thermocycler with the following cycle conditions: 94 C for 10 minutes followed by 35 cycles of 94 C for 30 seconds, 55 C for 30 seconds and 72 C for 1 minute, after which a final extension cycle of 72 C for 10 minutes was conducted. Most PCR reactions contained a single PCR product. The amplified cDNA products were purified using the Qiagen® PCR purification kit (Qiagen, Chatsworth, Calif.). These products were sequenced on an Applied Biosystems 373A automated DNA sequencer using the following oligonucleotide primer:

GCTATACCAAGCATACAATC (SEQ ID NO:35)

Taq dye-terminator sequencing reactions (Applied Biosystems, Foster City, Calif.) were conducted following the manufacturer's recommended procedures.

Each PCR fragment was translated in all six possible ways to identify those fragments which (1) had a potential signal peptide in the same direction as reporter gene; (2) had a stop codon(s) upstream of the putative methionine translation start site; and (3) appeared to lack a transmembrane domain.

One clone that met these criteria, termed "ymrs2-00009-c4", was selected for further analysis. This clone contained 5' sequence, including a putative signal sequence, but was lacking 3' sequence.

To obtain the 3' sequence of this clone, a 3' RACE reaction was performed using as a template pool number 4 from the YmHK2 cDNA library. This YmHK2 library was prepared as follows: First strand cDNA synthesis was performed using about 2 micrograms of the RNA obtained from the hippocampus of the kainate treated mice and about 1 ug of Not I primer-adapter having the following sequence:

GACTAGTTCTAGATCGCGAGCGGCCGCCCTTTTTTTTTTTTTT (SEQ ID NO:42)

Both the first strand and second strand cDNA synthesis reactions were performed using the Superscript® plasmid system (Gibco BRL, Grand Island, N.Y.). After second strand synthesis, the double stranded cDNA products were ligated into the double stranded adapters of SEQ ID NOs:16 and 17.

After ligation, the cDNA was digested to completion with Not I, and size fractionated on a 0.8 percent agarose gel. The cDNA products larger than about 800 base pairs were selected and purified from the gel using the Qiagen® gel extraction kit (Qiagen, Chatsworth, Calif.). The purified cDNA products were directly ligated into Sal I and Not I digested pSport® vector (Gibco BRL, Grand Island, N.Y.).

The ligated cDNA products were then introduced into electrocompetent E. coli cells called ElectroMax® DH10B (Gibco BRL, Grand Island, N.Y.). The library was then titered.

About twelve million primary clones were obtained, and expanded into about 250 ml of LB containing about 100 ug/ml ampicillin. After overnight incubation at 37 C, the plasmids were recovered using the Qiagen® maxi-prep kit (Qiagen, Chatsworth, Calif.).

About 20 ng of the plasmid library were used to transform the ElectroMax® DH10B electrocompetent E. coli cells using standard electroporation techniques. About two million transformants were divided into 40 pools (containing approximately 50,000 plasmids/pool). Each pool was then expanded into about 3 ml of LB medium containing about 100 ug/ml ampicillin. After overnight incubation at 37 C, the plasmids were recovered using the Qiagen® mini-prep kit. The DNA from each pool were then stored at about minus 20 C for future use.

The 3' RACE reaction was performed using about 1.5 ng of pool #4 of the YmHK2 library as a template, and using the Advantage® cDNA PCR kit (Clontech, Palo Alto, Calif.) with the following oligonucleotides:

CCAGCTGCTCTGTGGCAGCCCAG (SEQ ID NO:20)

CCCAGTCACGACGTTGTAAAACGACGGCC (SEQ ID NO:21)

The reaction was conducted in a standard thermocycler (Perkin-Elmer 9600) for thirty five cycles under the following conditions: 94 C for 1 minute; 94 C for 5 seconds, and 72 C for 5 minutes. This was followed by a final extension at 72 C for 10 minutes. About one microliter of the reaction products was diluted to 50 ul using TE buffer (10 mM TRIS pH 8.0 and 1 mM EDTA).

To enrich the RACE reaction for the gene of interest, a nested PCR reaction was conducted using about five microliters of the TE solution (containing the RACE reaction products as described in the preceding paragraph) together with the following oligonucleotides:

AACATGCAGCGGCTCGGGGG (SEQ ID NO:22)

GGTGACACTATAGAAGAGCTATGACGTCGC (SEQ ID NO:23)

The nested PCR reaction was incubated in a thermocycler (Perkin-Elmer 9600) using the following protocol: 94 C for one minute; five cycles of 94 C for 5 seconds followed by 72 C for 5 minutes; five cycles of 94 C for five seconds, followed by 70 C for 5 minutes; and 20-25 cycles of 94 C for 5 seconds followed by 68 C for 5 minutes. After this PCR, the 3' RACE products and the nested PCR products were analyzed using standard agarose gel electrophoresis.

A PCR product of about 3.3 kb was identified from the nested PCR reaction. This fragment was purified using Qiagen® Gel Extraction Kit (Qiagen, Chatsworth, Calif.) and ligated into the vector pCRII-TOPO (Invitrogen, Carlsbad, Calif.) according to the procedures recommended by the manufacturer. After ligation, the products were transformed into One Shot® E. coli cells (Invitrogen, Carlsbad, Calif.) and plated on a LB (Luria broth) plate containing about 100 ug/ml ampicillin and about 1.6 mg X-gal. After overnight incubation at 37 C, 12 white colonies and one blue colony were selected, and screened using PCR-Ready Beads® (Amersham-Pharmacia Biotech, Pistcataway, N.J.) according to the manufacturer's recommended protocol using oligonucleotide SEQ ID NO:20 together with the following primer:

GTGCTGAGTGTCTTCCATCAGC (SEQ ID NO:24)

Two colonies were picked that had yielded PCR products of the expected size of about 192 base pairs. These colonies were inoculated into about 3 ml of LB medium containing about 100 ug/ml ampicillin, and were incubated at 37 C. The cultures were placed on a shaker for about 16 hours, and the plasmids were recovered using Qiagen® mini prep columns (Qiagen, Chatsworth, Calif.) according to the manufacturer's protocol. Plasmid DNA was then sequenced as described above.

A contiguous stretch of DNA of about 3366 nucleotides was assembled by combining the sequence of clone ymrs2-00009-c4 (containing 5' sequence) together with the nested PCR fragment of 3.3 kb containing 3' sequence. Within this contiguous sequence is an open reading frame of 349 amino acids. The nucleotide sequence of this novel mouse gene, referred to as DKR-3, is set forth in FIG. 1. The putative amino acid sequence, as translated from the DNA sequence, is set forth in FIG. 8

A BLAST search of the Genbank database using the amino acid sequence of DKR-3 revealed that this open reading frame has homology to a gene known as human rig-like 7-1 mRNA (Genbank accession number AF034208; see also Ligon et al., *J NeuroVirology*, 4:217-226 [1998]). DKR-3 also has homology to the gene for chicken lens fiber protein clfest4 (Genbank accession number D26311); the overall identity to this protein is about 50 percent with the highest homology in the middle of the protein.

Example 2

Cloning of the Human DKR-3 Gene

Mouse DKR-3 DNA can be used to search a public EST database for human homologs, resulting in the identification of the following Genbank accession numbers:
AA628979
AA349552
AA633061
AA351624
W61032
T30923
AA683017
AA324686
T08793
T31076
R14945
AA226979
W45085
AA424460
R58671
R57834
AF034208

These EST sequences were analyzed and assembled to create a putative sequence for human DKR-3. Based on this putative sequence, two oligonucleotides were designed for use in PCR in an attempt to clone the human DKR-3 gene. The sequence of these oligonucleotides is:

GAGATGCAGCGGCTTGGGGCCACCC (SEQ ID NO:25)

GCCTGGTCAGCCCACGCCTAAAG (SEQ ID NO:26)

PCR was performed using the Advantage® cDNA PCR kit (Clontech, Palo Alto, Calif.) together with human fetal brain Quick-Clone® cDNA (Clontech). PCR was conducted in a thermocycler (Perkin-Elmer 9600) under the following cycle conditions: 94 C for 2 minute; 94 C for 30 seconds, and 72 C for 2 minutes. Thirty-five cycles were conducted after which samples were treated at 72 C for 10 minutes. A single fragment of about 1150 base pairs was visible when the PCR products were visualized on a 1 percent agarose gel. This fragment was purified using the Qiagen® Gel Extraction Kit (Qiagen, Chatsworth, Calif.) and ligated into the vector pCRII-TOPO (Invitrogen, Carlsbad, Calif.). After ligation, the products were transformed into One Shoot *E. coli*® (Invitrogen, Carlsbad, Calif.) and plated on a LB plate containing about 100 ug/ml ampicillin and about 1.6 mg X-gal. After overnight incubation at 37 C, 2 white colonies were picked and inoculated into about 3 ml of LB medium containing about 100 ug/ml ampicillin. The cultures were kept on a shaker at about 37 C for about 16 hours. The plasmids were isolated using Qiagen® mini-prep columns (Qiagen, Chatsworth, Calif.) according to the manufacturer's recommended protocol, and the inserts were then sequenced using methods described above.

The cloned fragment is 1141 bp in length and contains an open reading frame of 350 amino acids. The nucleotide sequence is set forth in FIG. 2, and the putative amino acid sequence, as translated from the DNA sequence, is set forth in FIG. 9. This amino acid sequence is about 80 percent identical to the mouse DKR-3 gene. In addition, human DKR-3 is identical to the human rig-like protein fragment described by Lignon et al., supra between amino acids 157 and 308 of DKR-3. Significantly, the rig-like protein has an amino terminal start corresponding to amino acid 156 of DKR-3. Rig-like does not appear to be a secreted protein, and the carboxy terminal region of rig-like protein has no homology to human DKR-3. Just as for mouse DKR-3, human DKR-3 is about 54 percent identical to the chicken lens fiber protein clfest. Human DKR-3 appears to be secreted, with a signal peptide cleavage site after either amino acid 20 or 21. Other potential cleavage sites (due to signal peptides or to other endogenous processing sites are after amino acid 16, 22, 32, and/or 41). There appear to be N-linked glycosylation sites at amino acids 96, 106, 121, and 204, which would render them preferable sites for generating substitution mutants. Human DKR-3 and mouse DKR-3 amino acid sequences differ at amino acid positions 6, 7, 11, 24, 27, 29, 30, 32, 33, 39, 81, 89, 93, 99, 101, 103, 109, 113, 115, 123, 126, 142, 156, 157, 162, 165, 173, 175, 191, 197, 198, 201, 203, 245, 247, 259, 283, 287, 292, 294, 295, 296, 298, 299, 304, 310, 311, 312, 314, 315, 329, 330, 334, 335, 336, 339, 340, 341, 342, 343, 345, and 347 (all with respect to the human DKR-3 sequence), which renders these positions preferable for generating human DKR-3 substitution or deletion variants. Based on computer analysis of the amino acid sequence of DKR-3, significant regions of the molecule include the span from about amino acids 21-145 (a potential alpha-helical region and region of potential N-linked glycosylation) such as for example amino acids 21-145, 40-145, 40-150, 45-145, and 45-150, the span from about amino acids 145-350, such as, for example 145-290, 145-300, and 145-350, and the span from about amino acids 300-350 (a second potential alpha-helical region), such as for example amino acids 310-350. Such regions would be suitable fragments of full length DKR-3.

Northern blot analysis was conducted to assess the tissue specific expression of human DKR-3. A probe for use in Northern blot analysis was prepared by PCR of human fetal brain Quick-Clone® cDNA (Clontech, Palo Alto, Calif.) using the following oligonucleotides:

CCTGCTGCTGGCGGCGGCGGTCCCCACGGC (SEQ ID NO:27)

GCCTGGTCAGCCCACGCCTAAAG (SEQ ID NO:28)

The PCR reaction was conducted in a thermocycler (Perkin-Elmer 9600). PCR conditions were: 94 C for 2 minute; 94 C for 30 seconds, and 72 C for 2 and ½ minutes. Thirty-five cycles were conducted followed by a final extension treatment at 72 C for 10 minutes. PCR products were run on a one percent agarose gel, and a band of about 1100 bp was gel purified using the Qiagen gel extraction kit (Qiagen®, Chatsworth, Calif.), cloned into the vector CRII-TOPO (Invitrogen, Carlsbad, Calif.) and sequenced to confirm that the band contained the human DKR-3 open reading frame minus the amino terminal 10 amino acids.

About twenty-five nanograms of this probe was denatured by heating to about 100 C for about 5 minutes, followed by placing on ice, and then radioactively labeled with alpha-32P-dCTP using the Rediprime® labeling kit (Amersham, Arlington Heights, Ill.) and following the manufacturer's instructions. A human multiple tissue Northern blot was purchased (Clontech, Palo Alto, Calif.) and was first prehybridized in about 5 ml of Clontech Express® hybridization buffer at about 68 C for 30-60 minutes. After prehybridization, the labeled probe was added to the solution and allowed to hybridize for about 60 minutes. After hybridization, the blot was first washed with 2×SSC plus 0.05 percent SDS at room temperature for about 30 minutes, then washed with 0.1×SSC plus 0.1 percent SDS at about 65 C for about 30 minutes. The blot was dried briefly and then exposed to a Phosphorimager screen (Molecular Dynamics, Sunnyvale, Calif.). After overnight exposure, the image of the blot was analyzed on a Storm 820 machine (Molecular Dynamics, Sunnyvale, Calif.) with Imagequat software (Molecular Dynamics, Sunnyvale, Calif.).

The size of the human DKR-3 RNA transcript is about 2.6 kb. The results of the Northern blot analysis indicate that human DKR-3 is highly expressed in adult heart and brain, although weak expression in placenta, adult lung, skeletal muscle, kidney, and pancreas is also apparent. A second smaller transcript is apparent in adult pancreas, and could result from degradation of the full length transcript.

To evaluate the role of this gene in cancer, a variety of human cancer cell lines were analyzed for the presence or absence of DKR-3 RNA transcript.

The glioblastoma cell lines Hs 683; A 172; SNB-19; U-87MG; and U-373MG are all from ATCC, and cultured in the media recommended by ATCC.

Normal human mammary epithelial cells (NMECs) derived from reduction mammoplasties were purchased from Clonetics Corp. (San Diego, Calif.) and the Corriel Institute (Camden, N.J.). The immortalized breast epithelial cell line MCF-10 and the ER+ cell line MCF-7 can be obtained from the American Type Culture Collection. The ER+ BT20T cells were provided by Dr. K. Keyomarsi (N.Y. State Dept. of Health). Immortalized 184A1 and other breast cancer cells including T47-D, ZR75-1, and BT474, MDA-MB-157, MDA-MB-231, MDA-MB-361, MDA-MB-453, MD-MBA-468, HS578T and SKBr3 were all obtained from the American Type Culture Collection (10801 University Blvd., Manassas, Va.).

NMECs, 184A1 and MCF10 cells were cultured in a modified DME/F12 medium (Gibco/BRL, Grand Island, N.Y.) supplemented with 10 mM Hepes, 2 mM glutamine, 0.1 mM nonessential amino acids, 0.5 mM ethanolamine, 5 mg/ml transferrin, 1 mg/ml Bovine serum albumin, 5.0 ng/ml sodium selenite, 20 ng/ml triiodothyronine, 10 ng/ml EGF, 5 μg/ml insulin and 0.5 μg/ml hydrocortisone (DMEM/F12C) (Ethier et al, *Cancer Letters,* 74:189-195 [1993]). The ER+ and ER+ breast cancer cells were cultured in Alpha or Richter improved minimal essential medium (MEM) (Gibco/BRL) supplemented with 10 mM Hepes, 2 mM glutamine, 0.1 mM nonessential amino acids, 10 percent fetal bovine serum and 1 μg/ml insulin.

Normal human bronchial and cervical epithelial cells were purchased from Clonetics Corp. (San Diego, Calif.). Normal cervical epithelial cells were culture in KBM2 (Clonetics Corp. San Diego, Calif.) supplemented with 13 mg/ml bovine pituitary extract, 0.5 μg/ml hydrocortisone, 2 ng/ml EGF, 0.5 mg/ml epinephrine, 0.1 ng/ml retinoic acid, 5 μg/ml transferrin, 6.5 ng/ml triiodothyronine and 5 μg/ml insulin. Normal bronchial epithelial cells were cultured in BEBM (Clonetics Crop., San Diego, Calif.) supplemented with 0.5 mg/ml hydrocortisone, 0.5 ng/ml EGF, 0.5 μg/ml epinephrine, 10 μg/ml transferrin, 5 μg/ml insulin, 0.1 ng/ml retinoic acid and 5.5 ng/ml triiodthyronine.

The lung cancer cell lines H1299, H23, H358, H441, H460, H520, H522, H727, H146, H209, H446, H510A, H526, and H889 and the cervical cancer cells Caski, C-4-I, MS751, SiHa and C-33-A were all obtained from the American Type Culture Collection. The lung cancer cells were cultured in RPMI (MEM) (Gibco/BRL) supplemented with 10 mM Hepes, 2 mM glutamine, 0.1 mM nonessential amino acids and 10 percent fetal bovine serum (FBS). The cervical cancer cells were cultured in Earles MEM supplemented with 0.1 mM nonessential amino acids, 1 mM sodium pyruvate and 10 percent FBS. All cells were routinely screened for mycoplasma contamination and maintained at about 37° C. in an atmosphere of about 6.5 percent $CO_2$.

Total RNA was prepared by lysing cell monolayers in guanidinium isothiocyanate and centrifuging over a 5.7 M CsCl cushion as described previously (Gudas, *Proc. Natl. Acad. Sci. USA,* 85:4705-4709 [1988]). RNA (about 20 ug) was electrophoresed on denaturing formaldehyde gels, transferred to MagnaNT membranes (Micron Separations Inc., Westboro, Ma) and cross-linked with UV irradiation.

The blots were prehybridized, probed, and washed under the same conditions as those set forth above for the tissue blot. The blots were dried briefly and then exposed to a Phosphorimager screen (Molecular Dynamics, Sunnyvale, Calif.). After overnight exposure, the image of the blot was analyzed on a Storm 820 machine with Imagequat software (both from Molecular Dynamics).

The results are shown in FIGS. 15A-15D. As can be seen in FIG. 15A, expression of DKR-3 is decreased in most of the breast cancer cell lines as compared to the normal cell lines. FIG. 15B indicates that DKR-3 expression is decreased in the non-small cell lung cancer cell lines, and in most of the small cell lung cancer cell lines as well. FIG. 15C indicates that expression of DKR-3 is decreased in three glioblastoma cell lines (SNB-19, U-87MG, and U-373MG) that are capable of forming tumors in nude mice (the other two cell lines, Hs 683 and A 172 do not form tumors in nude mice). FIG. 15D indicates that expression of DKR-3 is reduced in cervical cancer cell lines as compared to normal and immortalized cells.

Example 3

Cloning of the Human DKR-1 Gene

Human and mouse DKR-3 cDNA and amino acid sequences were used to search Genbank using the BLAST program in an attempt to identify DKR-3 related genes. A number of EST (expressed sequence tags) were found and were analyzed to determine whether the sequences overlapped. Using the following human EST accessions, a novel gene, termed DKR-1, was predicted.

AA336797
R27865
W39690
AA043027
HUM517H04B
AA143670
W51876
N94525
AA641247
AA137219
AA115249
AA031969
AA136192
AA032060
AA035583
AA207078
AA371363
AA037322
AA088618
W46873
AA115337
AA693679
W30750
H83554

PCR was conducted in an attempt to clone the full length gene, and the following two oligonucleotides were used for PCR:

```
CCCGGACCCTGACTCTGCAGCCG        (SEQ ID NO:29)

GAGGAAAAATAGGCAGTGCAGCACC      (SEQ ID NO:30)
```

PCR was performed using the Advantage® cDNA PCR kit (Clontech, Palo Alto, Calif.) containing the oligonucleotides listed above and human placenta Quick-Clone® cDNA (Clontech, Palo Alto, Calif.). The reaction was conducted according to the manufacturer's recommendations. Thirty-five cycles of PCR were conducted in a thermocycler (Perkin-Elmer 9600) under the following conditions: 94 C for 2 minutes; 94 C for 30 seconds, and 72 C for 1½ minutes, followed by a final extension at 72 C for 10 minutes.

After cycling, the PCR products were analyzed on a one percent agarose gel. A single band of about 1200 base pairs in length was detected after agarose gel electrophoresis. This fragment was purified using the Qiagen® gel extraction kit (Qiagen, Chatsworth, Calif.) and ligated into the vector pCRII-TOPO (Invitrogen, Carlsbad, Calif.) using standard ligation procedures. After ligation, the products were transformed into One Shoot® competent E. coli cells according to the procedures recommended by manufacturer (Invitrogen, Carlsbad, Calif.). The transformed E. coli cells were plated on a LB plate containing about 100 ug/ml ampicillin and about 1.6 mg X-gal.

After overnight incubation at about 37 C, two white colonies were picked and inoculated into about 3 ml of TB containing 100 ug/ml ampicillin. The culture was incubated at about 37 C for about 16 hours, plasmids were then recovered using Qiagen® mini-prep columns (Qiagen, Chatsworth, Calif.) and sequenced. Both colonies contained the same insert.

The insert is 1193 base pairs, and is referred to as human DKR-1. The sequence of this gene is set forth in FIG. 3. This gene contains an open reading frame of 266 amino acids. The amino acid sequence is set forth in FIG. 10. A stop codon is present upstream of the first methionine, indicating the first methionine is likely to be the amino terminus of the protein. Human DKR-1 has a predicted signal peptide with a predicted signal peptide cleavage site between amino acids 19 and 20.

The gene has about 80 percent homology to the mouse gene dkk-1 (Glinka et al., supra), however the mouse dkk-1 gene is 272 amino acids in length while human DKR-1 is 266 amino acids in length. Human DKR-1 differs from mouse dkk-1 at amino acid positions 3, 4, 5, 7, 8, 10, 12, 13, 14, 15, 16, 17, 18, 19, 22, 23, 24, 29, 53, 55, 62, 66, 69, 77, 93, 98, 101, 105, 106, 123, 139, 140, 143, 144, 153, 155, 157, 158, 163, 164, 165, 169, 175, 178, 197, 224, and 244. In addition, the alignment of human DKR-1 and mouse dkk-1 shows one gap in human DKR-1 between amino acids 37 and 38, and two gaps between 103 and 104, 146 and 147, and 165 and 166. Glinka et al. state on page 362 of their article that "Coordinates of Xenopus dkk family members have been deposited in Genbank with the following accession numbers . . . hdkk-1 AA207078." However, forward three frame translations of AA207078 by the inventors herein showed no homology to the published mouse and Xenopus dkk-1 sequences, or to the human DKR-1 sequence, except in the 3' end of this accession, which exhibits a 95 percent identity to human DKR-1 from amino acids 81-179, indicating that AA207078 does not encode full length human dkk-1. Significantly, AA207078 is missing amino acids 1-90 and 180-350 of human DKR-1 which includes the signal peptide and the second cysteine right domain respectively.

Example 4

Cloning of the Mouse DKR-2 Gene

Genbank accession number AA265561 (a mouse sequence) has homology to both human DKR-1 and human DKR-3 at the amino acid level based primarily on its cysteine pattern.

To extend this EST sequence in both the 5' and 3' directions, the following oligonucleotides were designed:

```
GCCACAGTCCCCACCAAGGATCATC      (SEQ ID NO:31)

GATGATCCTTGGTGGGGACTGTGGC      (SEQ ID NO:32)

CTGCAAACCAGTGCTCCATCAGGG       (SEQ ID NO:33)

CCCTGATGGAGCACTGGTTTGCAG       (SEQ ID NO:34)
```

Separately, 5' RACE and 3' RACE reactions were performed according to the manufacturer's protocol using mouse heart Marathon-Ready® cDNA and the Advantage® cDNA PCR kit (both from Clontech, Palo Alto, Calif.) and using oligonucleotide SEQ ID NOs: 31 and 34. The RACE reactions were incubated in a thermocycler (Perkin-Elmer 9600) using the following cycling conditions: 94 C for one minute; five cycles of 94 C for 5 seconds followed by 72 C for 5 minutes; five cycles of 94 C for five seconds, followed by 70 C for 5 minutes; and 20-25 cycles of 94 C for 5 seconds followed by 68 C for 5 minutes.

To enrich each RACE reaction for the desired product, about one microliter of each of the RACE PCR products was added together, and the mixture was diluted to about 50 ul using TE buffer. About five microliters of this solution were used to conduct nested PCR reactions. The Advantage® cDNA PCR kit (Clontech, Palo Alto, Calif.) and oligonucleotide SEQ ID NOs: 32 and 33 were used for the 5' and 3' nesting reactions, respectively. The nested PCR reactions were incubated in a thermocycler (Perkin-Elmer 9600) using the following program for thirty five cycles: 94 C for 1 minute; 94 C for 5 seconds; and 72 C for 2 minutes. A final extension was then conducted at 72 C for 10 minutes. The PCR products were analyzed using a one percent agarose gel.

Several fragments ranging from about 500 bp to about 1500 base pairs were obtained from the 5' nested PCR reaction, and two fragments of about 1900 bp and 450 bp were obtained from the 3' nested PCR reaction. These PCR products were purified using the Qiagen® PCR purification kit (Qiagen, Chatsworth, Calif.) and were then ligated into the vector pCRII-TOPO (Invitrogen). The ligation products were transformed into OneShot® E. coli cells (Invitrogen, Carlsbad, Calif.), and the cells were then plated on to two X-gal containing plates (one for each reaction) as described above.

Eight white colonies from each plate were picked and PCR selected via RACE reactions using the Clontech primer AP2 and the oligonucleotide SEQ ID NO:32 (for the 5' RACE) or the oligonucleotide SEQ ID NO:33 (for the 3' RACE). Three colonies from each plate that contained the correct size fragments were cultured, and the plasmids were isolated and sequenced using procedures described above.

Three clones, 9813302, 9813304 and 9813305 contained sequence which extended the EST sequence in the 5' direction. One clone, 9813308, contained sequence which extended the EST sequence in the 3' direction. A continuous sequence of 2678 base pairs was thus assembled using the sequence of clones 9813308, 9813304, and the EST AA265561. This full length DNA has been termed DKR-2, and the sequence is set forth in FIG. 4. The corresponding amino acid sequence is set forth in FIG. 11.

Within the amino acid sequence is an open reading frame of 259 amino acids. This protein has approximately 38 percent identity with mouse dkk-1 at the amino acid level. Mouse DKR-2 has a predicted signal peptide with a signal peptide cleavage site between amino acids 33 and 34.

Example 5

Cloning of the Human DKR-2 Gene

The Genbank EST database was searched using the BLAST program with both DNA and amino acid sequences from human DKR-1 and human DKR-3, and one human EST, W55979, was identified that showed homology to both human DKR-1 and human DKR-3 at the amino acid level based on its cysteine pattern. W55979 is about 88 percent identical to mouse DKR-2 at the DNA level, and about 93 percent identical to mouse DKR-2 at the amino acid level.

A BLAST search of Genbank W55979 indicated that W55979 has homology to BAC clone number B284B3 (Genbank accession number AC003099). BAC clone B284B3 is 95129 base pairs in length. Three portions of W55979 are homologous to three different regions of BAC clone B284B3, indicating that human DKR-2 has at least three exons. A 3' sequence of 556 bp in length was assembled based on the sequences of both BAC clone B284B3 and W55979, and it was determined that this sequence is the 3' portion of the human ortholog of mouse DKR-2. Within this 3' sequence of human DKR-2 is an open reading frame of 174 amino acids, and a stop codon is present after amino acid 174. This 3' sequence of human DKR-2 is about 97 percent identical to mouse DKR-2.

To obtain the 5' end sequence of human DKR-2, a 5' RACE reaction was performed using Clontech human heart Marathon-Ready® cDNA and the Advantage® cDNA PCR kit, together with oligonucleotide SEQ ID NO:34. The RACE reaction was performed according to the manufacturer's protocol. The 5' RACE reaction products were then subjected to nesting PCR to enrich for the 5' sequence using the Advantage® cDNA PCR kit and oligonucleotide SEQ ID NO:32. The PCR conditions for both the 5' RACE reaction and the nested PCR reaction were the same as those described in Example 4.

The nested PCR products were purified using the Qiagen® (Qiagen, Chatsworth, Calif.) PCR purification kit, and were ligated into the vector Zero-Blunt® (Invitrogen, San Diego, Calif.) according to the procedures recommended by the manufacturer. The ligation products were transformed into OneShot® E. coli cells which were then plated on X-gal containing plates as described above.

After overnight culturing, three white colonies were picked and were inoculated into about 3 ml of TB containing about 100 ug/ml ampicillin. The cultures were allowed to grow for about 16 hours, after which the plasmids were isolated using Qiagen® mini-prep columns (Qiagen, Chatsworth, Calif.) according to the manufacturer's protocol. The sequence of each insert was then obtained.

One of the 5'-RACE clones, termed 9812826, extended the human DKR-2 sequence 5'-terminally. A contiguous sequence of 1531 bp in length was assembled using this clone 9812826 together with the human DKR-2 3' sequence. Within this contiguous sequence is an open reading frame of 259 amino acids. The human DKR-2 gene has a predicted signal peptide of about 33 amino acids, with a predicted cut site between amino acids 33 and 34, and is about 95 percent identical to mouse DKR-2 at the amino acid level. The amino acid positions that differ between human and mouse DKR-2 include (with respect to the numbering of the human sequence) 7, 12, 28, 48, 50, 58, 71, 102, 119, 170, 173, and 191, rendering these positions preferable for generating amino acid substitution or deletion variants.

An alternative spliced isoform of human DKR-2 was discovered when PCR was conducted using human heart Marathon-Ready® cDNA (Clontech, Palo Alto, Calif.) and the Advantage® cDNA PCR kit (Clontech, Palo Alto, Calif.) together with the following oligonucleotides:

```
GGGTTGAGGGAACACAATCTGCAAG      (SEQ ID NO:36)

GTCTGCAATTGATGATGTTCCTCAATGG   (SEQ ID NO:37)
```

PCR was conducted using parameters set forth in the manufacturer's protocol. PCR products were analyzed by agarose gel electrophoresis, and two PCR products were obtained. The bands corresponding to these products were gel purified as described above, amplified and purified as described above, and then sequenced. One product corresponded to full length DKR-2, however, the other band corresponded to an isoform of DKR-2. This isoform has an open reading frame of 207 amino acids, and appears to be missing an exon. This isoform is referred to as human DKR-2a. The DNA sequence of human DKR-2a is set forth in FIG. 6, and the amino acid sequence as translated from the DNA is set forth in FIG. 13.

Example 6

Cloning of the Human DKR-4 Gene

A human EST that showed significant homology to human DKR-1 and human DKR-3 on protein level was identified in Genbank. This sequence, Genbank accession number AA565546, has a cysteine pattern that is similar to that of human DKR-1 and human DKR-3.

A BLAST search of Genbank showed no human ESTs overlapping with AA565546. Therefore, to extend the EST sequence in the 5' direction, a 5' RACE reaction was performed using human heart Marathon-Ready® cDNA (Clontech, Palo Alto, Calif.) together with the Advantage® cDNA PCR kit (Clontech, Palo Alto, Calif.) and the following oligonucleotide:

```
CCAGGGCCACAGTCGCAACGCTGG        (SEQ ID NO:38)
```

The RACE reaction was performed according to the protocol provided with the Advantage® kit. After 5' RACE, the products were nested to enrich for the desired 5' sequence using the Advantage® cDNA PCR kit according to the manufacturer's recommendations, together with the following oligonucleotide:

```
CTCCCTCTTGTCCCTTCCTGCCTTG       (SEQ ID NO:39)
```

After the nested PCR reaction, the products were purified using the Qiagen® PCR purification kit (Qiagen, Chatsworth, Calif.), ligated into the vector pCRII-TOPO (Invitrogen, Carlsbad, Calif.), and transformed into OneShot® E. coli cells as described above. After transformation, the cells were plated on a LB plate containing about 100 ug/ml ampicillin and about 1.6 mg X-gal.

After overnight incubation at 37 C, four white colonies were picked from the plate and were inoculated in about 3 ml TB containing about 100 ug/ml ampicillin. The cultures were incubated at about 37 C for about 16 hours. The plasmids were then recovered using Qiagen® mini-prep columns (Qiagen, Chatsworth, Calif.) and sequenced.

Two clones, termed 9813563 and 9853564, were found to contain the 5' sequence of human DKR-4.

To obtain the 3' sequence of human DKR-4, a 3' RACE reaction was performed using human uterus Marathon-Ready® cDNA (Clontech, Palo Alto, Calif.) together with the Advantage® cDNA PCR kit (Clontech) and the following oligonucleotide:

```
CAAGGCAGGAAGGGACAAGAGGGAG       (SEQ ID NO:40)
```

The 3' RACE reaction was performed according to the manufacturer's recommendations. After the RACE reaction, the products were nested using the Advantage® cDNA PCR kit and the following oligonucleotide:

```
CCAGCGTTGCGACTGTGGCCCTGG        (SEQ ID NO:41)
```

The parameters for PCR were 94 C for 1 minute followed by thirty five cycles of 94 C for 5 seconds and then 72 C for 2 minutes, after which a final extension of 70 C for 10 minutes was conducted. After the nesting reaction, the products were analyzed on a 1 percent agarose gel. A single band of about 1200 bp in length was observed. This band was purified from the gel using methods described above, and was then cloned into the vector pCR2.1-TOPO (Invitrogen, Carlsbad, Calif.) and sequenced. Sequence of this band indicated that it contained the 3' sequence of human DKR-4, and this sequence was assembled together with the 5' sequence (from clones 9813563 and 9853564) to generated the full length sequence of human DKR-4. This sequence is set forth in FIGS. 7 (DNA sequence) and 14 (translated amino acid sequence). The polypeptide is 224 amino acids in length and is about 34 percent identical to human DKR-1 at the amino acid sequence level.

Example 7

Expression of Human DKR-1 in Bacteria

PCR amplification employing the primer pairs and template described below were used to generate a recombinant form of human DKR-1. One primer of each pair introduces a TAA stop codon and a unique BamHI site following the carboxy terminus of the gene. The other primer of each pair introduces a unique NdeI site, a N-terminal methionine, and optimized codons for the amino terminal portion of the gene. PCR and thermocycling was performed using standard recombinant DNA methodology. The PCR products were purified, restriction digested, and inserted into the unique NdeI and BamHI sites of vector pAMG21 (ATCC accession no. 98113) and transformed into the prototrophic E. coli host GM121 (deposited with the American Type Culture Collection on XX as accession number XX). Other commonly used E. coli expression vectors and host cells are also suitable for expression by one skilled in the art. After transformation, positive clones were selected and examined for expression of the recombinant gene product.

The construct pAMG21-human DKR-1-24-266 was engineered to be 244 amino acids in length and have the following N-terminal and C-terminal residues, respectively:

```
Met-His-Pro-Leu-Leu-Gly         (SEQ ID NO:43)

Thr-Cys-Gln-Arg-His             (SEQ ID NO:44)
```

The template used for PCR was human DKR-1 cDNA and the following oligonucleotides were the primer pair used for PCR and cloning this gene construct:

```
                                (SEQ ID NO:45)
GTTCTCCTCATATGCATCCATTATTAGGCGTAAGTGCCACCTTGAACTCG

GTTCTCAAT (SEQ ID NO:46)
TACGCACTGGATCCTTAGTGTCTCTGACAAGTGTGAAG
```

Transformed E. coli strain GM121 containing pAMG21-human DKR-1-24-266 were grown in 2× YT media containing 20 micrograms/ml kanamycin at 30 C until the culture reached an optical density of about 600 nm of about 0.5. Induction of DKR-1 protein expression was achieved by addition of Vibrio fischeri synthetic autoinducer to 100 ng/ml final and incubation of the culture at either 30° C. or 37° C. for about 9 hours further with shaking. In addition, as a uninduced control, for each culture no autoinducer was added to an aliquot of the culture, but the culture was also incubated for about 9 hours further at about 30 C with shaking along with the induced cultures. After about 9 hours, the optical density of cultures were measured at 600 nm, an aliquot of cultures were examined by oil emersion microscopy at 1600× magnification, and aliquots of cultures were pelleted by centrifugation. Bacterial pellets of cultures were processed for SDS-polyacrylamide gel electrophoresis on a 14 percent gelto examine levels of protein produced in crude lysates and for N-terminal sequencing confirmation of the recombinant gene product. The gel was stained with Coomassie blue.

The results are shown in the photo of FIG. 16. Lane 1 contains molecular weight markers; Lanes 2 and 5 contain crude lysates of uninduced control cells incubated at 30 C; Lanes 3 and 6 are crude lysates of induced cells cultured at 30 C; Lanes 4 and 7 are crude lysates of induced cells cultured at 37 C. The arrow on the left of Lane 1 indicates the expected location of human DKR-1-24-266. As can be seen, large amounts of recombinant protein were observed in crude lysates of induced cultures at both 30° C. and 37° C. (Lanes 3 and 6, and 4 and 7). Microscopic analysis of bacterial cells revealed most cells contained at least one inclusion body, suggesting that at least some of the protein may be produced in the insoluble fraction of *E. coli.*

Example 8

Expression of DKR-2 in Bacteria

PCR amplification employing the primer pairs and templates described below were used to generate various forms of DKR-2. One primer of each pair introduces a TAA stop codon and a unique BamHI site following the carboxy terminus of the gene. The other primer of each pair introduces a unique NdeI site, a N-terminal methionine, and optimized codons for the amino terminal portion of the gene. PCR and thermocycling was performed using standard recombinant DNA methodology. The PCR products were purified, restriction digested, and inserted into the unique NdeI and BamHI sites of vector pAMG21 (ATCC accession no. 98113) and transformed into either prototrophic *E. coli* host GM121 or GM94 (GM 94 was deposited with the ATCC on XX as accession number XX). Other commonly used *E. coli* expression vectors and host cells are also suitable for expression. After transformation, positive clones were selected and examined for expression of the recombinant gene product.

The construct pAMG21-human DKR-2-26-259 was engineered to be 235 amino acids in length and have the following N-terminal and the following C-terminal amino acids, respectively:

```
Met-Ser-Gln-Ile-Gly-Ser       (SEQ ID NO:47)

Val-Cys-Gln-Lys-Ile.          (SEQ ID NO:48)
```

The template used for PCR was human DKR-2 cDNA and the following oligonucleotides were the primer pair used for PCR and cloning this gene construct.

```
                                          (SEQ ID NO:49)
GTTCTCCTCATATGTCTCAAATTGGTAGTTCTCGTGCCAAACTCAACTCC

ATCAAG (SEQ ID NO:50)
TACGCACTGGATCCTTAAATTTTCTGACACACATGGAGT
```

The construct pAMG21 mouse DKR-2-26-259 was engineered to be 235 amino acids in length and have the following N-terminal and C-terminal residues, respectively:

```
Met-Ser-Gln-Leu-Gly-Ser       (SEQ ID NO:51)

Val-Cys-Gln-Lys-Ile           (SEQ ID NO:52)
```

The template used for PCR was mouse DKR-2 cDNA, and the following oligonucleotides were the primer pair used for PCR and cloning this gene construct.

```
                                          (SEQ ID NO:53)
GTTCTCCTCATATGTCTCAATTAGGTAGCTCTCGTGCTAAACTCAACTCC
ATCAAGTCC (SEQ ID NO:54)
TACGCACTGGATCCTTAGATCTTCTGGCATACATGGAGT
```

Transformed *E. coli* GM121 or GM94 containing either pAMG21-human DKR-2-26-259 or pAMG21-mouse DKR-2-26-259 plasmid were grown in 2×YT media containing 20 μg/ml kanamycin at 30° C. until the culture reached an optical density at 600 nm of about 0.5. Induction of DKR-2 protein expression was achieved by addition of *Vibrio fischeri* synthetic autoinducer to 100 ng/ml final and incubation of the culture at either 30 C or 37 C for about 5 or 9 hours further with shaking. In addition, as a uninduced control, for each culture no autoinducer was added to an aliquot of the culture, but the culture was also incubated for about 5 or 9 hours further at 30 C with shaking along with the induced cultures. After either 5 or 9 hours incubation, the optical density of cultures were measured at about 600 nm, an aliquot of cultures were examined by oil emersion microscopy at 1600× magnification, and aliquots of cultures were pelleted by centrifugation. Bacterial pellets of cultures were processed for SDS-polyacrylamide gel electrophoresis on a 14 percent gel to examine levels of protein produced in crude lysates and for N-terminal sequencing confirmation of the recombinant gene product. The gel was stained with Coomassie blue.

Figure 17:
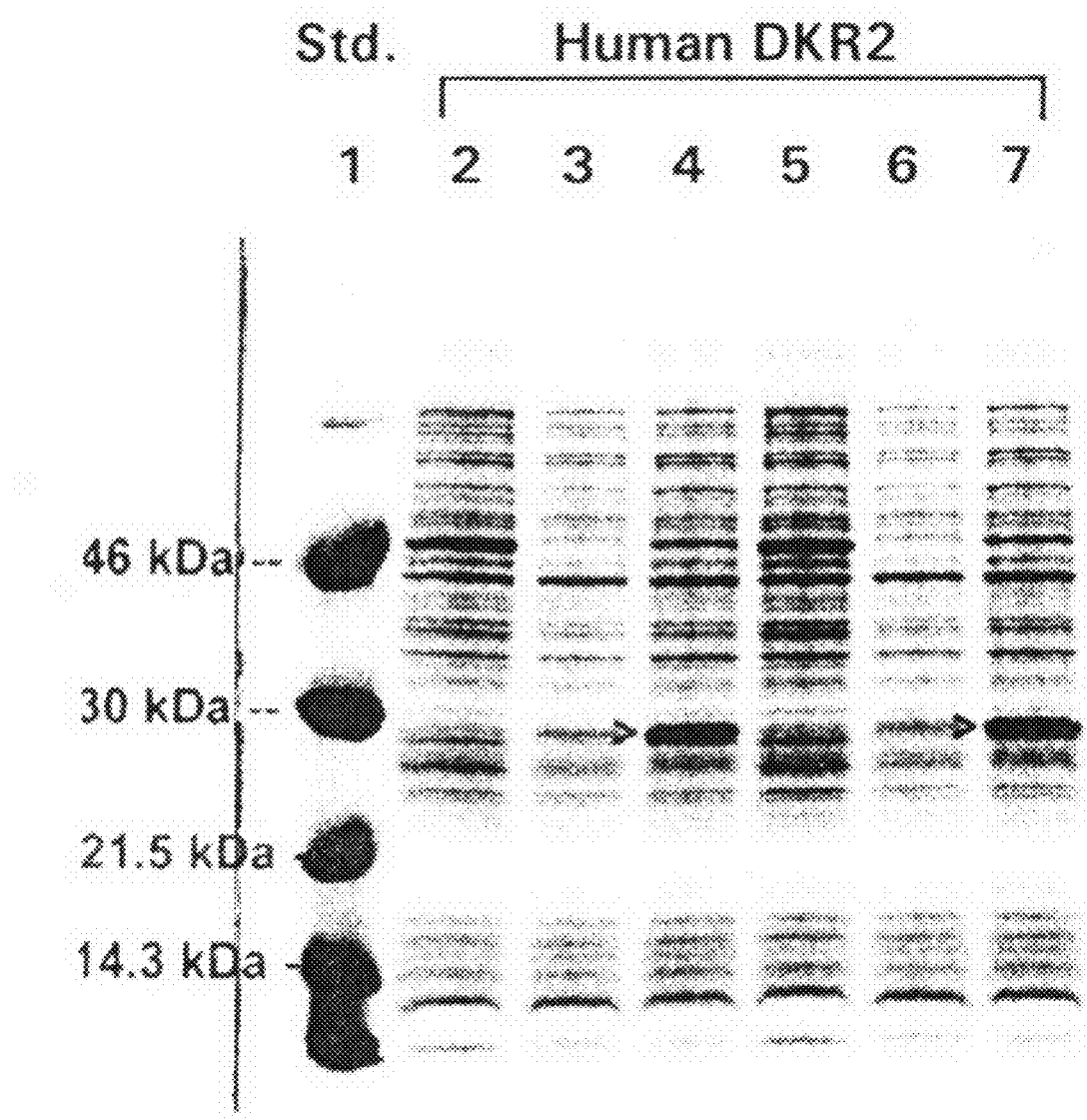
FIG. 17 is a photograph of SDS gel electrophoresis. The contents of the lanes are set forth in the Examples herein.

The results are shown in FIG. 16, Lanes 8-10 (human DKR-2 polypeptide) and in FIG. 17 (mouse DKR-2 polypeptide). In FIG. 16, Lane 8 contains crude lysate of uninduced control cells; Lane 9 contains crude lysate of induced cells cultured at 30 C, and Lane 10 contains crude lysate of induced cells cultured at 37 C. The arrow to the left of Lane 10 indicates the expected location of human DKR-2-26-259. As can be seen, significant amounts of polypeptide were generated in the induced cultures whether grown at 30 C or 37 C, while the uninduced cells did not produce a large amount of polypeptide. FIG. 17 shows the results of polypeptide production of mouse DKR-2-26-259. Lane 1 is molecular weight markers. Lanes 2-4 are one clone of *E. coli* cells transfected with the DKR-2 plasmid, while Lanes 5-7 are a second clone transfected with the same plasmid. Lanes 2 and 5 are crude lysates of uninduced control cells; Lanes 3 and 6 are crude lysates of induced cells cultured at 30 C; and Lanes 4 and 7 are crude lysates of cells cultured at 37 C. The arrows to the left of Lanes 4 and 7 indicate the expected location of the DKR-2 polypeptide. As can be seen, large amounts of recombinant protein were observed in crude lysates of induced cultures at 37 C but not at 30 C. Microscopic analysis of bacterial cells revealed most cells contained at least one inclusion body, suggesting that at least some of the protein may be produced in the insoluble fraction of E. coli.

Example 9

Expression of DKR-3 in Bacteria

PCR amplification employing the primer pairs and templates described below were used to generate various forms of DKR-3. One primer of each pair introduces a TAA stop codon and a unique SacII site following the carboxy terminus of the gene. The other primer of each pair introduces a unique NdeI site, a N-terminal methionine, and optimized codons for the amino terminal portion of the gene. PCR and thermocycling was performed using standard recombinant DNA methodology. The PCR products were purified, restriction digested, and inserted into the unique NdeI and SacII sites of vector pAMG21 (ATCC accession no. 98113) and transformed into the prototrophic E. coli host GM121. Other commonly used E. coli expression vectors and host cells are also suitable for expression by one skilled in the art. After transformation, positive clones were selected, plasmid DNA was isolated and the sequence of the DKR-3 gene insert was confirmed.

The construct pAMG21-human DKR-3-23-350 was engineered to be 329 amino acids in length and have the following N-terminal and C-terminal residues, respectively:

```
Met-Pro-Ala-Pro-Thr-Ala    (SEQ ID NO:55)
Gly-Gly-Glu-Glu-Ile.       (SEQ ID NO:56)
```

The template used for PCR was human DKR-3 cDNA and the following oligonucleotides were the primer pair used for PCR and cloning this gene construct.

```
                                          (SEQ ID NO:57)
GTTCTCCTCATATGCCTGCTCCAACTGCAACTTCGGCTCCAGTCAAGCCC
GGCC (SEQ ID NO:58)
TACGCACTCCGCGGTTAAATCTCTTCCCCTCCCAGCA
```

The construct pAMG21-human DKR-3-33-350 was engineered to be 319 amino acids in length and have the following N-terminal and C-terminal residues, respectively:

```
Met-Lys-Pro-Gly-Pro-Ala    (SEQ ID NO:59)
Gly-Gly-Glu-Glu-Ile        (SEQ ID NO:60)
```

The template used for PCR was human DKR-3 cDNA and the following oligonucleotides were the primer pair used for PCR and cloning this gene construct:

```
                                          (SEQ ID NO:61)
GTTCTCCTCATATGAAACCAGGTCCAGCCTTAAGCTACCCGCAGGAGGAG
GCCA (SEQ ID NO:62)
TACGCACTCCGCGGTTAAATCTCTTCCCCTCCCAGCA
```

The construct pAMG21-human DKR-3-42-350 was engineered to be 310 amino acids in length and have the following N-terminal and C-terminal residues, respectively:

```
Met-Gln-Glu-Glu-Ala-Thr    (SEQ ID NO:63)
Gly-Gly-Glu-Glu-Ile        (SEQ ID NO:64)
```

The template used for PCR was human DKR-3 cDNA and the following oligonucleotides were the primer pair used for PCR and cloning this gene construct:

```
                                          (SEQ ID NO:65)
GTTCTCCTCATATGCAAGAAGAAGCTACTCTGAATGAGATGTTCCGCGAG
GTT (SEQ ID NO:66)
TACGCACTCCGCGGTTAAATCTCTTCCCCTCCCAGCA
```

The construct pAMG21-mouse DKR-3-33-349 was engineered to be 318 amino acids in length and have the following N-terminal and C-terminal residues, respectively:

```
Met-Glu-Pro-Gly-Pro-Ala    (SEQ ID NO:67)
Gly-Glu-Glu-Glu-Ile        (SEQ ID NO:68)
```

The template used for PCR was mouse DKR-3 cDNA and the following oligonucleotides were the primer pair used for PCR and cloning this gene construct:

```
                                          (SEQ ID NO:69)
GTTCTCCTCATATGGAACCAGGTCCAGCTTTAAACTACCCTCAGGAGGAA
GCTA (SEQ ID NO:70)
TACGCACTCCGCGGTTAAATCTCCTCCTCTCCGCCTA
```

Figure 18:
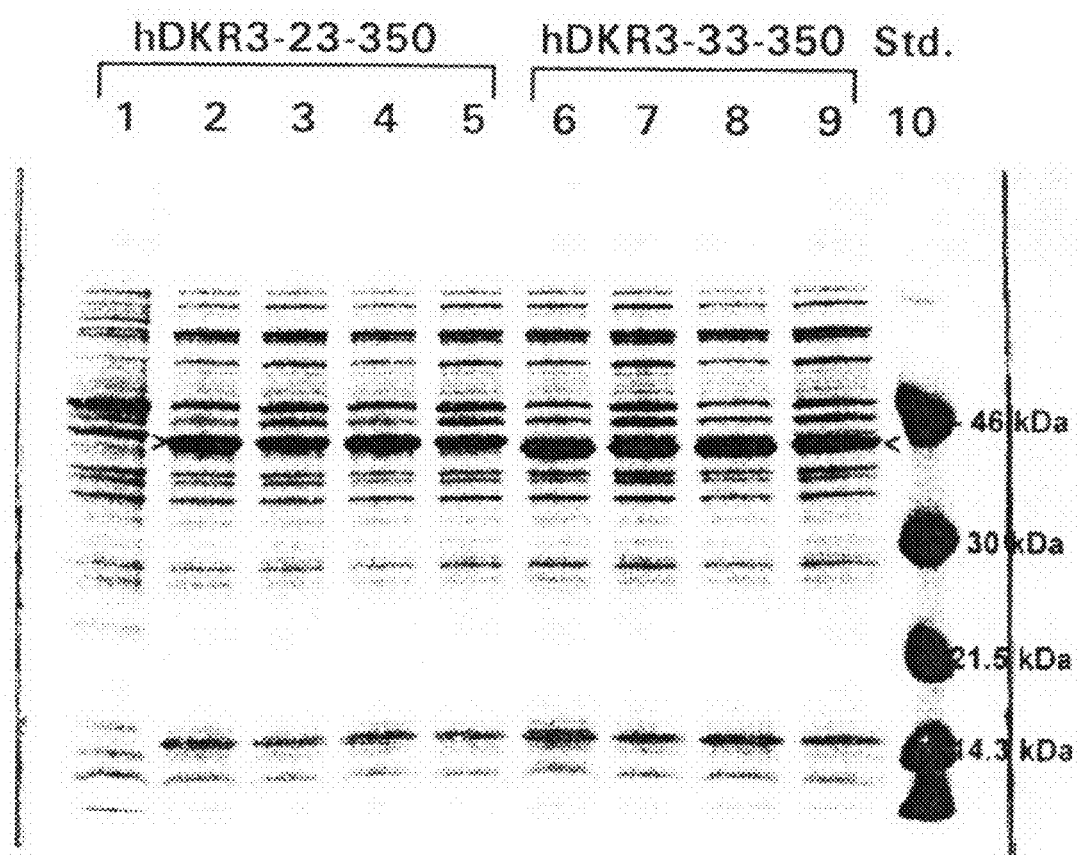
FIG. 18 is a photograph of SDS gel electrophoresis. The contents of the lanes are set forth in the Examples herein.
Figure 19:
FIG. 19 is a photograph of SDS gel electrophoresis. The contents of the lanes are set forth in the Examples herein.

Transformed E. coli GM121 containing the various pAMG21 DKR-3 plasmids described above were grown in 2×YT media containing 20 micrograms/ml kanamycin at 30° C. until the culture reached an optical density at 600 nm of about 0.5. Induction of DKR-3 polypeptide expression was achieved by addition of Vibrio fischeri synthetic autoinducer to 100 ng/ml final concentration and incubation of the culture at either 30 or 37 C for about 6 hours further with shaking. In addition, as a uninduced control, for each culture no autoinducer was added to an aliquot of the culture, but the culture was also incubated for about 6 hours further at 30 C with shaking along with the induced cultures. After about 6 hours, the optical density of cultures were measured at about 600 nm, an aliquot of cultures were examined by oil emersion microscopy at 1600× magnification, and aliquots of cultures were pelleted by centrifugation. Bacterial pellets of cultures were processed for SDS-polyacrylamide gel electrophoresis to examine levels of protein produced in crude lysates, or bacterial pellets were processed to determine whether the recombinant protein was in the soluble or insoluble fraction of E. coli and for N-terminal sequencing confirmation of the recombinant gene product. The results are shown as photos of the SDS gels in FIGS. 18 and 19. In FIG. 18, Lane 10 is molecular weight markers, and Lanes 1-9 are crude lystes of bacterial cells. Lane 1 is crude lysate of uninduced control cells; Lanes 2, 4, 6, and 8 are crude lysates of induced cells cultured at 30 C; Lanes 3, 5, 7, and 9 are induced cells cultured at 37 C. Lanes 1-5 contain lysates of cells transfected with the pAMG21-human DKR-3-23-350 construct; and Lanes 6-9 contain lysates of cells transfected with the pAMG21-human DKR-3-33-350 construct. The arrows to the left of Lane 2 and the right of Lane 9 indicate the expected location of the DKR-3 polypeptides. FIG. 19 contains molecular weight markers in Lane 10; Lanes 1-5 are crude lysates of cultured cells transfected with the pAMG21-human DKR-3-42-350 construct; Lanes 6-9 are crude lysates of cells transfected with the pAMG21-mouse DKR-3-33-349 construct. Lanes 1 and 6 are uninduced controls; Lanes 2, 4, 7, and 8 are crude lysates of induced cells cultured at 30 C (two different clones of each construct); Lanes 3, 5, and 9 are crude lysates of induced cells cultured at 37 C (two separate clones of the human DKR-3-42-350 construct in Lanes 3 and 5). The arrow to the right of Lane 9 indicates the expected location of the mouse DKR-3 polypeptides; the arrow to the left of Lane 4 indicates the expected location of human DKR-3 polypeptide. As can be seen, all DKR-3 constructs produced large amounts of recombinant protein in E. coli. No inclusion bodies could be detected by oil emersion microscopy, and the recombinant polypeptides were mostly found in the soluble fraction of the cells.

Example 10

Expression of DKR-4 in Bacteria

PCR amplification employing the primer pairs and template described below were used to generate a recombinant form of human DKR-4. One primer of each pair introduces a TAA stop codon and a unique BamHI site following the carboxy terminus of the gene. The other primer of each pair introduces a unique NdeI site, a N-terminal methionine, and optimized codons for the amino terminal portion of the gene. PCR and thermocycling was performed using standard recombinant DNA methodology. The PCR products were purified, restriction digested, and inserted into the unique NdeI and BamHI sites of the vector pAMG21 (ATCC accession no. 98113) and transformed into the prototrophic E. coli host GM94. Other commonly used E. coli expression vectors and host cells are also suitable for expression. After transformation, positive clones were selected and will be examined for expression of the recombinant gene product.

The construct pAMG21-human DKR-4-19-224 was engineered to be 207 amino acids in length and have the following N-terminal and C-terminal residues, respectively:

```
Met-Leu-Val-Leu-Asp-Phe        (SEQ ID NO:71)

Lys-Ile-Glu-Lys-Leu            (SEQ ID NO:72)
```

The template used for PCR was human DKR-4 cDNA and the following oligonucleotides were the primer pair used for PCR and cloning this gene construct:

```
                                              (SEQ ID NO:73)
GTTCTCCTCATATGTTAGTTTTGGATTTCAACAACATCAGGAGCTCT (SEQ ID NO:74)
TACGCACTGGATCCTTACAGTTTTTCTATTTTTTGGCATACTCTTAATC
```

It is anticipated that DKR-4 polypeptide could be prepared using the PCR product as described above for the other DKR polypeptides.

Example 11

Production and Purification of DKR-3 Polypeptide in Mammalian Cells

Human DKR-3 cDNA was cloned onto the mammalian expression vector pcDNA3.1 (−)/mycHis (Invitrogen, Carlsbad, Calif.) and the vector construct was amplified using the Qiagen maxi-prep kit (Qiagen, Chatsworth, Calif.) standard ligation techniques.

Human embryonic kidney 293T cells (American Type Culture Collection) were cultured in 10 cm dishes, and grown to about 80 percent confluence. The cells were then transfected with the vector construct using the DMRIE-C® liposome formulation (Gibco BRL, Grand Island, N.Y.) as follows. About 240 microliters of DMRIE-C® were added to 8 ml of Optimem medium. About 40 ul (equivalent to about 56 micrograms) of purified vector construct was then added to another 8 ml of Optimem. After mixing and incubation at room temperature for about 15 minutes, 2 ml of this solution was added to each of 8 plates. After about 5 hours, the medium was aspirated and 10 ml of DME medium containing about 10 percent fetal calf serum was added. The cells were incubated 16-18 hours after which the medium was removed and about 10 ml of SF Optimem medium per well without phenol red were added. After about 24 hours, this medium, the "conditioned medium" was harvested, passed over a 0.22 micron filter and stored at 4° C. The cells were then incubated in another 10 ml of SF Optimem per plate. After 24 hours, this medium was collected, filtered and also stored at 4° C.

Figure 20:
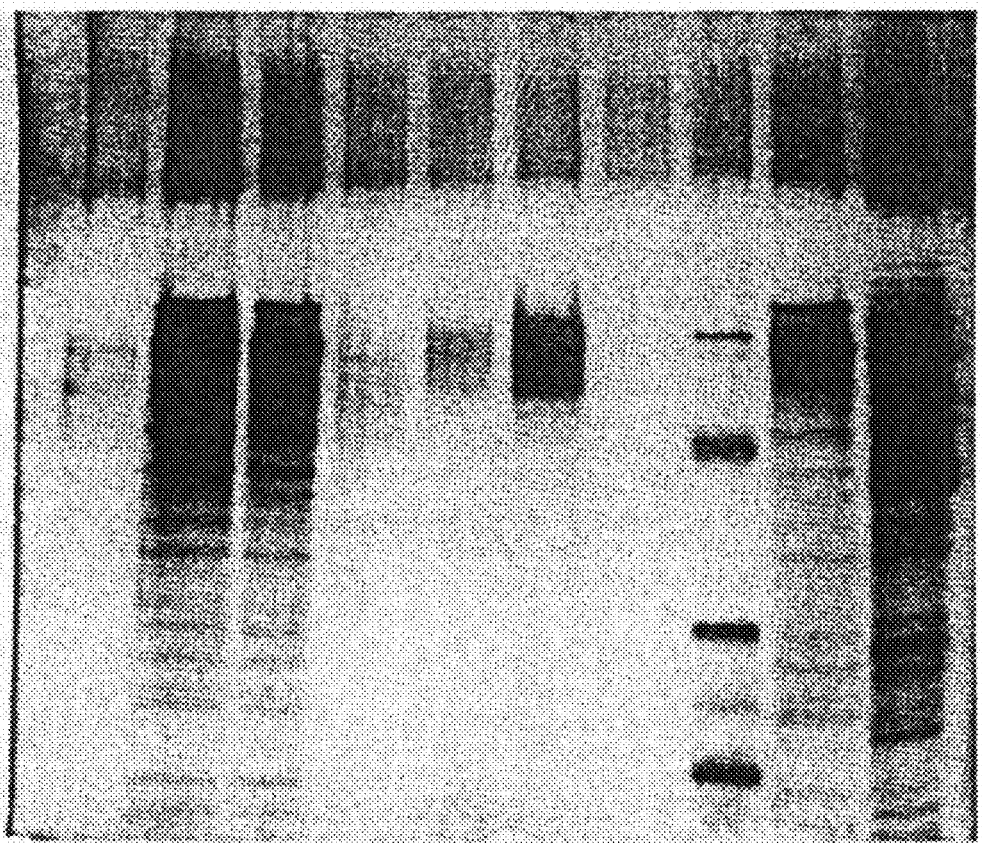
FIG. 20 is a photograph of SDS gel electrophoresis. The contents of the lanes are set forth in the Examples herein.

The conditioned media was added to a buffer containing 50 mM NaPO$_4$, pH8, and 250 mM sodium chloride, and passed over a column of nickel-Sephadex (Qiagen, Chatsworth, Calif.). Non-specifically bound proteins were eluted using the same buffer containing 10 mM imidazole, followed by the same buffer containing 20 mM imidazole. DKR-3 was then eluted using 125 mM-250 mM imidazole. Fractions from the column were subjected to 12 percent SDS gel electrophores and silver stained. The results are shown in FIG. 20. Lane 2 contains material that was loaded on to the gel. Lane 3 contains the flow through fraction after loading the column with conditioned medium, Lanes 4, 5, 6, and 7 contain column fractions after treatment with 10, 20, 125, and 250 mM imidazole. Molecular weight standards are shown in Lane 8. As can be seen a single band of protein of the correct molecular weight is seen in Lanes 5 and 6, indicating that this procedure resulted in generation of purified DKR-3 protein (attached to myc and His tags). Smearing of the protein band may be due to glycosylation. Separately, a Western blot was run to confirm that the purified protein did indeed have a His tag (indicating that the fusion protein DKR-3 mycHis had been produced). The Western blot was prepared using standard procedures and was proved with a polyclonal anti-His-HRP antibody (Invitrogen, Carlsbad, Calif.). A photo of the Western blot is shown in FIG. 21; the Lanes correspond to that for the gel (described immediately above). As can be seen, there is antibody binding in Lanes 2, 5, and 6, indicating that DKR-3 mycHis was loaded on to the column and was eluted in the 20 and 125 mM imidazole washes.

Example 12

Anchorage Independent Growth Assay

A distinguishing feature of many cancer cell lines is their ability to grow in an anchorage independent manner. Whereas normal cells will only grow and divide until they come in contact with their neighbors, cancer cells continue to grow and divide after contact, thereby forming tumors. Thus, one assay for cancer cell growth inhibitor compounds measures the ability of cancer cells to grow and divide in the presence of the compound. There are many ways known to the skilled artisan in which this assay can be conducted, however two preferred methods are set forth below.

A. Stably Transfected Cell Assay

In this procedure, any human cancer cell line that does not express the DKR gene to be tested (either human DKR-1, 2, 3, 4, or a fragment or variant thereof) is transfected with the DKR gene under evaluation, where the DKR gene is inserted into a vector such as pcDNA3.1 (Invitrogen, Carlsbad, Calif.) or other suitable mammalian expression vector. Transfection can be conducted as described herein. The transfected cancer cells are cultured to generate a stably transfected cell line. Once a stably transfected cell line has been established, the cells are added to Noble or equivalent agar (about 0.35 percent) prepared in standard mammalian cell culture medium such as RPMI. The cell/agar solution is poured on to petri plates containing solidified agar ban (about 0.5 percent agar). Colony formation is evaluated daily to determine the rate of growth of the cells, and culture medium is added to each plate as needed. Separately, the same cells are transfected with vector only (containing no DKR gene). These "control" cells are then treated in an identical manner to the DKR gene containing cells and can be used as a standard of comparison for the DKR gene containing cells.

Examples of suitable cancer cell lines for conducting this assay include, without limitation, human breast cancer cell line MCF7 and the glioblastoma cell line U-87MG.

B. Protein Assay

An alternate or additional assay to measure the growth of cancer cell lines treated with a DKR polypeptide is as follows. Any human cancer cell line not expressing the DKR polypeptide under evaluation can be cultured and prepared with an agar solution as described above. The cells can then be plated as described, and a solution of DKR polypeptide (either full length, or a fragment or variant thereof) in culture medium can be added to the agar either daily, every other day, or once per week for three weeks. Typically, a concentration of about 10 nM will be added, although a series of dilutions ranging from 1 nM to 1 mM can be used. Control plates will receive a solution of culture medium only. The plates can be monitored daily for up to about three weeks to evaluate cell colony formation. After three weeks, control and experimental plates can be compared for the number and size of cell colonies. It is anticipated that those plates receiving DKR polypeptide that is biologically active will have fewer cell colonies, and the colonies will be smaller, as compared to control plates.

Example 13

In Vivo Tumor Assay

The ability of each DKR polypeptide to inhibit tumor growth in vivo can be evaluated as follows. Tumor cells not expressing the DKR gene under evaluation can be transfected using procedures described herein with a DKR nucleic acid construct encoding a full length DKR gene, or a fragment or variant thereof. The transfected cells can be maintained in culture (as described herein) until ready for use.

Male or female athymic nude mice (Charles River Labs, Boston, Mass.) are kept in a sterile environment. The mice are then injected with about $2 \times 10^6$ cells (either DKR transfected cells or control "vector only" transfected cells) in a total volume of about 0.1 ml can be injected subcutaneously. The mice can then be examined daily for appearance of (a) tumor(s) and for the size of the tumor. Preferably, the mice will be examined for up to about six months so as to provide time for tumor growth (and regression where DKR polypeptides are effective at decreasing tumor growth). The tumor(s), where present, can then be removed, weighed and examined for (1) the presence of DKR polypeptide, and (2) morphology. Tumors from mice containing DKR construct transfected cells can be compared to tumors from mice containing cells transfected with vector only. It is anticipated that DKR polypeptides, due to their similarity with dkk-1, a potent wnt8 antagonist, will be able to decrease the size of the tumor as compared with controls.

We claim:

1. An isolated polypeptide comprising the amino acid sequence of SEQ ID NO:13.

2. The isolated polypeptide of claim 1, wherein the polypeptide is linked to a polymer.

3. The isolated polypeptide of claim 2, wherein the polymer is selected from the group consisting of a polyethylene glycol polymer, dextran, cellulose and polyvinyl alcohol.

* * * * *

SEQUENCE LISTING

```
<160> NUMBER OF SEQ ID NOS: 78

<210> SEQ ID NO 1
<211> LENGTH: 1050
<212> TYPE: DNA
<213> ORGANISM: Mouse

<400> SEQUENCE: 1
atgcagcggc tcgggggtat tttgctgtgt acactgctgg cggcggcggt ccccactgct      60
cctgctcctt ccccgacggt cacttggact ccggcggagc cgggcccagc tctcaactac     120
cctcaggagg aagctacgct caatgagatg tttcgagagg tggaggagct gatggaagac     180
actcagcaca aactgcgcag tgccgtggag gagatggagg cggaagaagc agctgctaaa     240
acgtcctctg aggtgaacct ggcaagctta cctcccaact atcacaatga gaccagcacg     300
```

```
gagaccaggg tgggaaataa cacagtccat gtgcaccagg aagttcacaa gataaccaac    360
aaccagagtg gacaggtggt cttttctgag acagtcatta catctgtagg ggatgaagaa    420
ggcaagagga gccatgaatg tatcattgat gaagactgtg ggcccaccag gtactgccag    480
ttctccagct tcaagtacac ctgccagcca tgccgggacc agcagatgct atgcacccga    540
gacagtgagt gctgtggaga ccagctgtgt gcctggggtc actgcaccca aaaggccacc    600
aaaggtggca atgggaccat ctgtgacaac agagggatt gccagcctgg cctgtgttgt    660
gccttccaaa gaggcctgct gttccccgtg tgcacacccc tgcccgtgga gggagagctc    720
tgccatgacc ccaccagcca gctgctggat ctcatcacct gggaactgga gcctgaagga    780
gctttggacc gatgcccctg cgccagtggc ctcctatgcc agccacacag ccacagtctg    840
gtgtacatgt gcaagccagc cttcgtgggc agccatgacc acagtgagga gagccagctg    900
cccagggagg ccccggatga gtacgaagat gttggcttca taggggaagt gcgccaggag    960
ctggaagacc tggagcggag cctagcccag gagatggcat ttgaggggcc tgcccctgtg   1020
gagtcactag gcggagagga ggagatttag                                    1050

<210> SEQ ID NO 2
<211> LENGTH: 1053
<212> TYPE: DNA
<213> ORGANISM: Human

<400> SEQUENCE: 2
atgcagcggc ttggggccac cctgctgtgc ctgctgctgg cggcggcggt ccccacggcc     60
cccgcgcccg ctccgacggc gacctcggct ccagtcaagc ccggcccggc tctcagctac    120
ccgcaggagg aggccaccct caatgagatg ttccgcgagg ttgaggaact gatggaggac    180
acgcagcaca aattgcgcag cgcggtggaa gagatggagg cagaagaagc tgctgctaaa    240
gcatcatcag aagtgaacct ggcaaactta cctcccagct atcacaatga ccaacaca     300 gacacgaagg ttggaaataa taccatccat gtgcaccgag aaattcacaa gataaccaac    360
aaccagactg gacaaatggt cttttcagag acagttatca catctgtggg agacgaagaa    420
ggcagaagga gccacgagtg catcatcgac gaggactgtg ggcccagcat gtactgccag    480
tttgccagct tccagtacac ctgccagcca tgccgggcc agaggatgct ctgcacccgg    540
gacagtgagt gctgtggaga ccagctgtgt gtctggggtc actgcaccaa aatggccacc    600 agggggcagca atgggaccat ctgtgacaac agagggact gccagccggg ctgtgctgt    660 gccttccaga gaggcctgct gttccctgtg tgcacacccc tgcccgtgga gggcgagctt    720
tgccatgacc ccgccagccg gcttctggac ctcatcacct gggagctaga gcctgatgga    780
gccttggacc gatgcccttg tgccagtggc ctcctctgcc agccccacag ccacagcctg    840
gtgtatgtgt gcaagccgac cttcgtgggg agccgtgacc aagatgggga gatcctgctg    900
cccagagagg tccccgatga gtatgaagtt ggcagcttca tggaggaggt gcgccaggag    960
ctggaggacc tggagaggag cctgactgaa gagatggcgc tgggggagcc tgcggctgcc   1020
gccgctgcac tgctgggagg ggaagagatt tag                                1053

<210> SEQ ID NO 3
<211> LENGTH: 801
<212> TYPE: DNA
<213> ORGANISM: Human

<400> SEQUENCE: 3
```

```
atgatggctc tgggcgcagc gggagctacc cgggtctttg tcgcgatggt agcggcggct    60
ctcggcggcc accctctgct gggagtgagc gccaccttga actcggttct caattccaac   120
gctatcaaga acctgccccc accgctgggc ggcgctgcgg ggcacccagg ctctgcagtc   180
agcgccgcgc cgggaatcct gtacccgggc gggaataagt accagaccat tgacaactac   240
cagccgtacc cgtgcgcaga ggacgaggag tgcggcactg atgagtactg cgctagtccc   300
acccgcggag gggacgcggg cgtgcaaatc tgtctcgcct gcaggaagcg ccgaaaacgc   360
tgcatgcgtc acgctatgtg ctgccccggg aattactgca aaaatggaat atgtgtgtct   420
tctgatcaaa atcatttccg aggagaaatt gaggaaacca tcactgaaag ctttggtaat   480
gatcatagca ccttggatgg gtattccaga agaaccacct tgtcttcaaa aatgtatcac   540
accaaaggac aagaaggttc tgtttgtctc cggtcatcag actgtgcctc aggattgtgt   600
tgtgctagac acttctggtc caagatctgt aaacctgtcc tgaaagaagg tcaagtgtgt   660
accaagcata ggagaaaagg ctctcatgga ctagaaatat tccagcgttg ttactgtgga   720
gaaggtctgt cttgccggat acagaaagat caccatcaag ccagtaattc ttctaggctt   780
cacacttgtc agagacacta a                                             801

<210> SEQ ID NO 4
<211> LENGTH: 780
<212> TYPE: DNA
<213> ORGANISM: Mouse

<400> SEQUENCE: 4
atggccgcgc tgatgcgggt caaggattca tcccgctgcc ttctcctact ggccgcggtg    60
ctgatggtgg agagctcaca gctaggcagc tcgcgggcca aactcaactc catcaagtcc   120
tctctaggag gggagactcc tgctcagtca gccaaccgat ctgcaggcat gaaccaagga   180
ctggctttcg gcggcagtaa gaagggcaaa agcctgggc aggcctaccc ttgcagcagt   240
gataaggaat gtgaagttgg aagatactgc cacagtcccc accaaggatc atcagcctgc   300
atgctctgta ggaggaaaaa gaaacgatgc cacagagatg ggatgtgttg ccctggtacc   360
cgctgcaata atggaatctg catcccagtc actgagagca tcctcacccc acatatccca   420
gctctggatg gcacccggca tagagatcgc aaccatggtc actattccaa ccatgacctg   480
ggatggcaga atctaggaag gccacactcc aagatgcctc atataaaagg acatgaagga   540
gacccatgcc tacggtcatc agactgcatt gatgggtttt gttgtgctcg ccacttctgg   600
accaaaatct gcaaaccagt gctccatcag ggggaagtct gtaccaaaca acgcaagaag   660
ggttcgcacg gctggagat tttccagagg tgtgactgtg caagggcct gtcctgcaaa   720 gtgtggaaag atgccaccta ctcttccaaa gccagactcc atgtatgcca agagatctga   780

<210> SEQ ID NO 5
<211> LENGTH: 780
<212> TYPE: DNA
<213> ORGANISM: Human

<400> SEQUENCE: 5
atggccgcgt tgatgcggag caaggattcg tcctgctgcc tgctcctact ggccgcggtg    60
ctgatggtgg agagctcaca gatcggcagt tcgcgggcca aactcaactc catcaagtcc   120
tctctgggcg gggagacgcc tggtcaggcc gccaatcgat ctgcgggcat gtaccaagga   180
ctggcattcg gcggcagtaa gaagggcaaa aacctgggc aggcctaccc ttgtagcagt   240
gataaggagt gtgaagttgg gaggtattgc cacagtcccc accaaggatc atcggcctgc   300
```

```
atggtgtgtc ggagaaaaaa gaagcgctgc caccgagatg gcatgtgctg ccccagtacc    360
cgctgcaata atggcatctg tatcccagtt actgaaagca tcttaacccc tcacatcccg    420
gctctggatg gtactcggca cagagatcga aaccacggtc attactcaaa ccatgacttg    480
ggatggcaga atctaggaag accacacact aagatgtcac atataaaagg catgaagga     540 gaccctgcc tacgatcatc agactgcatt aagggtttt gctgtgctcg tcatttctgg      600
accaaaatct gcaaccagt gctccatcag ggggaagtct gtaccaaaca acgcaagaag     660
ggttctcatg ggctggaaat tttccagcgt tgcgactgtg cgaagggcct gtcttgcaaa    720
gtatggaaag atgccaccta ctcctccaaa gccagactcc atgtgtgtca gaaatttga    780
```

<210> SEQ ID NO 6
<211> LENGTH: 624
<212> TYPE: DNA
<213> ORGANISM: Human

<400> SEQUENCE: 6

```
atggccgcgt tgatgcggag caaggattcg tcctgctgcc tgctcctact ggccgcggtg     60
ctgatggtgg agagctcaca gatcggcagt tcgcgggcca aactcaactc catcaagtcc    120
tctctgggcg gggagacgcc tggtcaggcc gccaatcgat ctgcgggcat gtaccaagga    180
ctggcattcg gcggcagtaa aagggcaaa aacctggggc aggcctaccc ttgtagcagt     240
gataaggagt gtgaagttgg gaggtattgc cacagtcccc accaaggatc atcggcctgc    300
atggtgtgtc ggagaaaaaa gaagcgctgc caccgagatg gcatgtgctg ccccagtacc    360
cgctgcaata atgggcatga aggagacccc tgcctacgat catcagactg cattgaaggg    420
ttttgctgtg ctcgtcattt ctggaccaaa atctgcaaac cagtgctcca tcaggggaa    480 gtctgtacca acaacgcaa gaagggttct catgggctgg aaatttttcca gcgttgcgac    540 tgtgcgaagg gcctgtcttg caaagtatgg aaagatgcca ctactcctc caaagccaga    600 ctccatgtgt gtcagaaaat ttga                                           624
```

<210> SEQ ID NO 7
<211> LENGTH: 675
<212> TYPE: DNA
<213> ORGANISM: Human

<400> SEQUENCE: 7

```
atggtggcgg ccgtcctgct ggggctgagc tggctctgct ctcccctggg agctctggtc     60
ctggacttca caacatcag gagctctgct gacctgcatg gggcccggaa gggctcacag    120
tgcctgtctg acacggactg caataccaga aagttctgcc tccagccccg cgatgagaag    180
ccgttctgtg ctacatgtcg tgggttgcgg aggaggtgcc agcgagatgc catgtgctgc    240
cctgggacac tctgtgtgaa cgatgttttgt actacgatgg aagatgcaac cccaatatta    300
gaaaggcagc ttgatgagca agatggcaca catgcagaag aacaactggg caccccagtc    360
caggaaaacc aacccaaaag gaagccaagt attaagaaat cacaaggcag aagggacaa    420 gagggagaaa gttgtctgag aacttttgac tgtggccctg actttgctg tgctcgtcat    480 ttttggacga aaatttgtaa gccagtcctt ttggagggac aggtctgctc cagaagaggg    540
cataaagaca ctgctcaagc tccagaaatc ttccagcgtt gcgactgtgg ccctggacta    600
ctgtgtcgaa gccaattgac cagcaatcgg cagcatgctc gattaagagt atgccaaaaa    660
atagaaaagc tataa                                                      675
```

<210> SEQ ID NO 8
<211> LENGTH: 349
<212> TYPE: PRT
<213> ORGANISM: Mouse

<400> SEQUENCE: 8

Met Gln Arg Leu Gly Gly Ile Leu Leu Cys Thr Leu Leu Ala Ala Ala
1               5                   10                  15

Val Pro Thr Ala Pro Ala Pro Ser Pro Thr Val Thr Trp Thr Pro Ala
            20                  25                  30

Glu Pro Gly Pro Ala Leu Asn Tyr Pro Gln Glu Glu Ala Thr Leu Asn
        35                  40                  45

Glu Met Phe Arg Glu Val Glu Glu Leu Met Glu Asp Thr Gln His Lys
    50                  55                  60

Leu Arg Ser Ala Val Glu Glu Met Glu Ala Glu Ala Ala Ala Lys
65                  70                  75                  80

Thr Ser Ser Glu Val Asn Leu Ala Ser Leu Pro Pro Asn Tyr His Asn
                85                  90                  95

Glu Thr Ser Thr Glu Thr Arg Val Gly Asn Asn Thr Val His Val His
            100                 105                 110

Gln Glu Val His Lys Ile Thr Asn Asn Gln Ser Gly Gln Val Val Phe
        115                 120                 125

Ser Glu Thr Val Ile Thr Ser Val Gly Asp Glu Glu Gly Lys Arg Ser
    130                 135                 140

His Glu Cys Ile Ile Asp Glu Asp Cys Gly Pro Thr Arg Tyr Cys Gln
145                 150                 155                 160

Phe Ser Ser Phe Lys Tyr Thr Cys Gln Pro Cys Arg Asp Gln Gln Met
                165                 170                 175

Leu Cys Thr Arg Asp Ser Glu Cys Cys Gly Asp Gln Leu Cys Ala Trp
            180                 185                 190

Gly His Cys Thr Gln Lys Ala Thr Lys Gly Gly Asn Gly Thr Ile Cys
        195                 200                 205

Asp Asn Gln Arg Asp Cys Gln Pro Gly Leu Cys Cys Ala Phe Gln Arg
    210                 215                 220

Gly Leu Leu Phe Pro Val Cys Thr Pro Leu Pro Val Glu Gly Glu Leu
225                 230                 235                 240

Cys His Asp Pro Thr Ser Gln Leu Leu Asp Leu Ile Thr Trp Glu Leu
                245                 250                 255

Glu Pro Glu Gly Ala Leu Asp Arg Cys Pro Cys Ala Ser Gly Leu Leu
            260                 265                 270

Cys Gln Pro His Ser His Ser Leu Val Tyr Met Cys Lys Pro Ala Phe
        275                 280                 285

Val Gly Ser His Asp His Ser Glu Glu Ser Gln Leu Pro Arg Glu Ala
    290                 295                 300

Pro Asp Glu Tyr Glu Asp Val Gly Phe Ile Gly Glu Val Arg Gln Glu
305                 310                 315                 320

Leu Glu Asp Leu Glu Arg Ser Leu Ala Gln Glu Met Ala Phe Glu Gly
                325                 330                 335

Pro Ala Pro Val Glu Ser Leu Gly Gly Glu Glu Glu Ile
            340                 345

<210> SEQ ID NO 9
<211> LENGTH: 350
<212> TYPE: PRT
<213> ORGANISM: Human

<400> SEQUENCE: 9

```
Met Gln Arg Leu Gly Ala Thr Leu Leu Cys Leu Leu Leu Ala Ala Ala
  1               5                  10                  15

Val Pro Thr Ala Pro Ala Pro Thr Ala Thr Ser Ala Pro Val
             20                  25                  30

Lys Pro Gly Pro Ala Leu Ser Tyr Pro Gln Glu Glu Ala Thr Leu Asn
             35                  40                  45

Glu Met Phe Arg Glu Val Glu Glu Leu Met Glu Asp Thr Gln His Lys
         50                  55                  60

Leu Arg Ser Ala Val Glu Glu Met Glu Ala Glu Ala Ala Ala Ala Lys
 65                  70                  75                  80

Ala Ser Ser Glu Val Asn Leu Ala Asn Leu Pro Pro Ser Tyr His Asn
                 85                  90                  95

Glu Thr Asn Thr Asp Thr Lys Val Gly Asn Asn Thr Ile His Val His
            100                 105                 110

Arg Glu Ile His Lys Ile Thr Asn Asn Gln Thr Gly Gln Met Val Phe
            115                 120                 125

Ser Glu Thr Val Ile Thr Ser Val Gly Asp Glu Glu Gly Arg Arg Ser
        130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
        195                 200                 205

Asp Asn Gln Arg Asp Cys Gln Pro Gly Leu Cys Cys Ala Phe Gln Arg
    210                 215                 220

Gly Leu Leu Phe Pro Val Cys Thr Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
            260                 265                 270

Cys Gln Pro His Ser His Ser Leu Val Tyr Val Cys Lys Pro Thr Phe
        275                 280                 285

Val Gly Ser Arg Asp Gln Asp Gly Glu Ile Leu Leu Pro Arg Glu Val
    290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Glu Met Ala Leu Gly Glu
                325                 330                 335

Pro Ala Ala Ala Ala Ala Leu Leu Gly Gly Glu Glu Ile
            340                 345                 350
```

<210> SEQ ID NO 10
<211> LENGTH: 266
<212> TYPE: PRT
<213> ORGANISM: Human

<400> SEQUENCE: 10

```
Met Met Ala Leu Gly Ala Ala Gly Ala Thr Arg Val Phe Val Ala Met
  1               5                  10                  15
```

```
Val Ala Ala Ala Leu Gly Gly His Pro Leu Leu Gly Val Ser Ala Thr
             20                  25                  30

Leu Asn Ser Val Leu Asn Ser Asn Ala Ile Lys Asn Leu Pro Pro Pro
         35                  40                  45

Leu Gly Gly Ala Ala Gly His Pro Gly Ser Ala Val Ser Ala Ala Pro
     50                  55                  60

Gly Ile Leu Tyr Pro Gly Gly Asn Lys Tyr Gln Thr Ile Asp Asn Tyr
 65                  70                  75                  80

Gln Pro Tyr Pro Cys Ala Glu Asp Glu Glu Cys Gly Thr Asp Glu Tyr
                 85                  90                  95

Cys Ala Ser Pro Thr Arg Gly Gly Asp Ala Gly Val Gln Ile Cys Leu
                 100                 105                 110

Ala Cys Arg Lys Arg Lys Arg Cys Met Arg His Ala Met Cys Cys
             115                 120                 125

Pro Gly Asn Tyr Cys Lys Asn Gly Ile Cys Val Ser Ser Asp Gln Asn
         130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                 165                 170                 175

Lys Met Tyr His Thr Lys Gly Gln Glu Gly Ser Val Cys Leu Arg Ser
             180                 185                 190

Ser Asp Cys Ala Ser Gly Leu Cys Cys Ala Arg His Phe Trp Ser Lys
         195                 200                 205

Ile Cys Lys Pro Val Leu Lys Glu Gly Gln Val Cys Thr Lys His Arg
     210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                 245                 250                 255

Ser Ser Arg Leu His Thr Cys Gln Arg His
             260                 265

<210> SEQ ID NO 11
<211> LENGTH: 259
<212> TYPE: PRT
<213> ORGANISM: Mouse

<400> SEQUENCE: 11

Met Ala Ala Leu Met Arg Val Lys Asp Ser Ser Arg Cys Leu Leu Leu
 1               5                  10                  15

Leu Ala Ala Val Leu Met Val Glu Ser Ser Gln Leu Gly Ser Ser Arg
             20                  25                  30

Ala Lys Leu Asn Ser Ile Lys Ser Ser Leu Gly Gly Glu Thr Pro Ala
         35                  40                  45

Gln Ser Ala Asn Arg Ser Ala Gly Met Asn Gln Gly Leu Ala Phe Gly
     50                  55                  60

Gly Ser Lys Lys Gly Lys Ser Leu Gly Gln Ala Tyr Pro Cys Ser Ser
 65                  70                  75                  80

Asp Lys Glu Cys Glu Val Gly Arg Tyr Cys His Ser Pro His Gln Gly
                 85                  90                  95

Ser Ser Ala Cys Met Leu Cys Arg Arg Lys Lys Arg Cys His Arg
                 100                 105                 110

Asp Gly Met Cys Cys Pro Gly Thr Arg Cys Asn Asn Gly Ile Cys Ile
```

-continued

```
            115                 120                 125
Pro Val Thr Glu Ser Ile Leu Thr Pro His Ile Pro Ala Leu Asp Gly
        130                 135                 140

Thr Arg His Arg Asp Arg Asn His Gly His Tyr Ser Asn His Asp Leu
145                 150                 155                 160

Gly Trp Gln Asn Leu Gly Arg Pro His Ser Lys Met Pro His Ile Lys
                165                 170                 175

Gly His Glu Gly Asp Pro Cys Leu Arg Ser Ser Asp Cys Ile Asp Gly
                180                 185                 190

Phe Cys Cys Ala Arg His Phe Trp Thr Lys Ile Cys Lys Pro Val Leu
                195                 200                 205

His Gln Gly Glu Val Cys Thr Lys Gln Arg Lys Lys Gly Ser His Gly
        210                 215                 220

Leu Glu Ile Phe Gln Arg Cys Asp Cys Ala Lys Gly Leu Ser Cys Lys
225                 230                 235                 240

Val Trp Lys Asp Ala Thr Tyr Ser Ser Lys Ala Arg Leu His Val Cys
                245                 250                 255

Gln Lys Ile

<210> SEQ ID NO 12
<211> LENGTH: 259
<212> TYPE: PRT
<213> ORGANISM: Human

<400> SEQUENCE: 12

Met Ala Ala Leu Met Arg Ser Lys Asp Ser Ser Cys Cys Leu Leu Leu
  1               5                  10                  15

Leu Ala Ala Val Leu Met Val Glu Ser Ser Gln Ile Gly Ser Ser Arg
                 20                  25                  30

Ala Lys Leu Asn Ser Ile Lys Ser Ser Leu Gly Gly Glu Thr Pro Gly
            35                  40                  45

Gln Ala Ala Asn Arg Ser Ala Gly Met Tyr Gln Gly Leu Ala Phe Gly
        50                  55                  60

Gly Ser Lys Lys Gly Lys Asn Leu Gly Gln Ala Tyr Pro Cys Ser Ser
 65                  70                  75                  80

Asp Lys Glu Cys Glu Val Gly Arg Tyr Cys His Ser Pro His Gln Gly
                 85                  90                  95

Ser Ser Ala Cys Met Val Cys Arg Arg Lys Lys Lys Arg Cys His Arg
            100                 105                 110

Asp Gly Met Cys Cys Pro Ser Thr Arg Cys Asn Asn Gly Ile Cys Ile
        115                 120                 125

Pro Val Thr Glu Ser Ile Leu Thr Pro His Ile Pro Ala Leu Asp Gly
        130                 135                 140

Thr Arg His Arg Asp Arg Asn His Gly His Tyr Ser Asn His Asp Leu
145                 150                 155                 160

Gly Trp Gln Asn Leu Gly Arg Pro His Thr Lys Met Ser His Ile Lys
                165                 170                 175

Gly His Glu Gly Asp Pro Cys Leu Arg Ser Ser Asp Cys Ile Glu Gly
                180                 185                 190

Phe Cys Cys Ala Arg His Phe Trp Thr Lys Ile Cys Lys Pro Val Leu
                195                 200                 205

His Gln Gly Glu Val Cys Thr Lys Gln Arg Lys Lys Gly Ser His Gly
        210                 215                 220

Leu Glu Ile Phe Gln Arg Cys Asp Cys Ala Lys Gly Leu Ser Cys Lys
```

225                 230                 235                 240
Val Trp Lys Asp Ala Thr Tyr Ser Ser Lys Ala Arg Leu His Val Cys
                245                 250                 255

Gln Lys Ile

<210> SEQ ID NO 13
<211> LENGTH: 207
<212> TYPE: PRT
<213> ORGANISM: Human

<400> SEQUENCE: 13

Met Ala Ala Leu Met Arg Ser Lys Asp Ser Cys Cys Leu Leu Leu
  1               5                  10                  15

Leu Ala Ala Val Leu Met Val Glu Ser Ser Gln Ile Gly Ser Ser Arg
                20                  25                  30

Ala Lys Leu Asn Ser Ile Lys Ser Ser Leu Gly Gly Glu Thr Pro Gly
                35                  40                  45

Gln Ala Ala Asn Arg Ser Ala Gly Met Tyr Gln Gly Leu Ala Phe Gly
            50                  55                  60

Gly Ser Lys Lys Gly Lys Asn Leu Gly Gln Ala Tyr Pro Cys Ser Ser
 65                 70                  75                      80

Asp Lys Glu Cys Glu Val Gly Arg Tyr Cys His Ser Pro His Gln Gly
                85                  90                  95

Ser Ser Ala Cys Met Val Cys Arg Arg Lys Lys Lys Arg Cys His Arg
                100                 105                 110

Asp Gly Met Cys Cys Pro Ser Thr Arg Cys Asn Asn Gly His Glu Gly
                115                 120                 125

Asp Pro Cys Leu Arg Ser Asp Cys Ile Glu Gly Phe Cys Ala
            130                 135                 140

Arg His Phe Trp Thr Lys Ile Cys Lys Pro Val Leu His Gln Gly Glu
145                 150                 155                 160

Val Cys Thr Lys Gln Arg Lys Lys Gly Ser His Gly Leu Glu Ile Phe
                165                 170                 175

Gln Arg Cys Asp Cys Ala Lys Gly Leu Ser Cys Lys Val Trp Lys Asp
                180                 185                 190

Ala Thr Tyr Ser Ser Lys Ala Arg Leu His Val Cys Gln Lys Ile
                195                 200                 205

<210> SEQ ID NO 14
<211> LENGTH: 224
<212> TYPE: PRT
<213> ORGANISM: Human

<400> SEQUENCE: 14

Met Val Ala Ala Val Leu Leu Gly Leu Ser Trp Leu Cys Ser Pro Leu
  1               5                  10                  15

Gly Ala Leu Val Leu Asp Phe Asn Asn Ile Arg Ser Ser Ala Asp Leu
                20                  25                  30

His Gly Ala Arg Lys Gly Ser Gln Cys Leu Ser Asp Thr Asp Cys Asn
                35                  40                  45

Thr Arg Lys Phe Cys Leu Gln Pro Arg Asp Glu Lys Pro Phe Cys Ala
            50                  55                  60

Thr Cys Arg Gly Leu Arg Arg Arg Cys Gln Arg Asp Ala Met Cys Cys
 65                 70                  75                      80

Pro Gly Thr Leu Cys Val Asn Asp Val Cys Thr Thr Met Glu Asp Ala
                85                  90                  95

```
Thr Pro Ile Leu Glu Arg Gln Leu Asp Glu Gln Asp Gly Thr His Ala
            100                 105                 110

Glu Gly Thr Thr Gly His Pro Val Gln Glu Asn Gln Pro Lys Arg Lys
        115                 120                 125

Pro Ser Ile Lys Lys Ser Gln Gly Arg Lys Gly Gln Glu Gly Glu Ser
    130                 135                 140

Cys Leu Arg Thr Phe Asp Cys Gly Pro Gly Leu Cys Cys Ala Arg His
145                 150                 155                 160

Phe Trp Thr Lys Ile Cys Lys Pro Val Leu Leu Glu Gly Gln Val Cys
                165                 170                 175

Ser Arg Arg Gly His Lys Asp Thr Ala Gln Ala Pro Glu Ile Phe Gln
            180                 185                 190

Arg Cys Asp Cys Gly Pro Gly Leu Leu Cys Arg Ser Gln Leu Thr Ser
        195                 200                 205

Asn Arg Gln His Ala Arg Leu Arg Val Cys Gln Lys Ile Glu Lys Leu
    210                 215                 220

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 15
ggaaggaaaa aagcggccgc aacannnnnn nnn                            33

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide adapter

<400> SEQUENCE: 16
tcgacccacg cgtccg                                               16

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence:
      Oligonucleotide adapter

<400> SEQUENCE: 17
gggtgcgcag gc                                                   12

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 18
actagctcca gtgatctc                                             18

<210> SEQ ID NO 19
```

```
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 19
cgtcattgtt ctcgttcc                                               18

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 20
ccagctgctc tgtggcagcc cag                                         23

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 21
cccagtcacg acgttgtaaa acgacggcc                                   29

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 22
aacatgcagc ggctcggggg                                             20

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 23
ggtgacacta tagaagagct atgacgtcgc                                  30

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 24
gtgctgagtg tcttccatca gc                                          22

<210> SEQ ID NO 25
<211> LENGTH: 25
```

```
<212> TYPE: DNA
<213> ORGANISM: Artificial Sequence
<220> FEATURE:
<223> OTHER INFORMATION: Description of Artificial Sequence:
      Oligonucleotide probes

<400> SEQUENCE: 25
gagatgcagc ggcttggggc caccc                                          25

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide probes

<400> SEQUENCE: 26
gcctggtcag cccacgccta aag                                            23

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide probes

<400> SEQUENCE: 27
cctgctgctg gcggcggcgg tccccacggc                                     30

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide probes

<400> SEQUENCE: 28
gcctggtcag cccacgccta aag                                            23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide probes

<400> SEQUENCE: 29
cccggaccct gactctgcag ccg                                            23

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide probes

<400> SEQUENCE: 30
gaggaaaaat aggcagtgca gcacc                                          25

<210> SEQ ID NO 31
<211> LENGTH: 25
<212> TYPE: DNA
```

```
<213> ORGANISM: Artificial Sequence
<220> FEATURE:
<223> OTHER INFORMATION: Description of Artificial Sequence:
      Oligonucleotide primers

<400> SEQUENCE: 31
gccacagtcc ccaccaagga tcatc                                          25

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide primers

<400> SEQUENCE: 32
gatgatcctt ggtggggact gtggc                                          25

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primers

<400> SEQUENCE: 33
ctgcaaacca gtgctccatc aggg                                           24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primers

<400> SEQUENCE: 34
ccctgatgga gcactggttt gcag                                           24

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 35
gctataccaa gcatacaatc                                                20

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 36
gggttgaggg aacacaatct gcaag                                          25

<210> SEQ ID NO 37
<211> LENGTH: 28
<212> TYPE: DNA
<213> ORGANISM: Artificial Sequence
```

```
<220> FEATURE:
<223> OTHER INFORMATION: Description of Artificial Sequence:
      Oligonucleotide probe

<400> SEQUENCE: 37
gtctgcaatt gatgatgttc ctcaatgg                                    28

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 38
ccagggccac agtcgcaacg ctgg                                        24

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 39
ctccctcttg tcccttcctg ccttg                                       25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 40
caaggcagga agggacaaga gggag                                       25

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 41
ccagcgttgc gactgtggcc ctgg                                        24

<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide primer/adapter

<400> SEQUENCE: 42
gactagttct agatcgcgag cggccgccct tttttttttt tttt                  44

<210> SEQ ID NO 43
<211> LENGTH: 6
<212> TYPE: PRT
<213> ORGANISM: Human
```

```
<400> SEQUENCE: 43

Met His Pro Leu Leu Gly
  1               5

<210> SEQ ID NO 44
<211> LENGTH: 5
<212> TYPE: PRT
<213> ORGANISM: Human

<400> SEQUENCE: 44

Thr Cys Gln Arg His
  1               5

<210> SEQ ID NO 45
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 45
gttctcctca tatgcatcca ttattaggcg taagtgccac cttgaactcg gttctcaat        59

<210> SEQ ID NO 46
<211> LENGTH: 38
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 46
tacgcactgg atccttagtg tctctgacaa gtgtgaag                               38

<210> SEQ ID NO 47
<211> LENGTH: 6
<212> TYPE: PRT
<213> ORGANISM: Human

<400> SEQUENCE: 47

Met Ser Gln Ile Gly Ser
  1               5

<210> SEQ ID NO 48
<211> LENGTH: 5
<212> TYPE: PRT
<213> ORGANISM: Human

<400> SEQUENCE: 48

Val Cys Gln Lys Ile
  1               5

<210> SEQ ID NO 49
<211> LENGTH: 56
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 49
gttctcctca tatgtctcaa attggtagtt ctcgtgccaa actcaactcc atcaag           56

<210> SEQ ID NO 50
```

```
<211> LENGTH: 39
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 50
tacgcactgg atccttaaat tttctgacac acatggagt                            39

<210> SEQ ID NO 51
<211> LENGTH: 6
<212> TYPE: PRT
<213> ORGANISM: Mouse

<400> SEQUENCE: 51

Met Ser Gln Leu Gly Ser
 1               5

<210> SEQ ID NO 52
<211> LENGTH: 5
<212> TYPE: PRT
<213> ORGANISM: Mouse

<400> SEQUENCE: 52

Val Cys Gln Lys Ile
 1               5

<210> SEQ ID NO 53
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 53
gttctcctca tatgtctcaa ttaggtagct ctcgtgctaa actcaactcc atcaagtcc      59

<210> SEQ ID NO 54
<211> LENGTH: 39
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 54
tacgcactgg atccttagat cttctggcat acatggagt                            39

<210> SEQ ID NO 55
<211> LENGTH: 6
<212> TYPE: PRT
<213> ORGANISM: Human

<400> SEQUENCE: 55

Met Pro Ala Pro Thr Ala
 1               5

<210> SEQ ID NO 56
<211> LENGTH: 5
<212> TYPE: PRT
<213> ORGANISM: Human

<400> SEQUENCE: 56

Gly Gly Glu Glu Ile
```

-continued

<210> SEQ ID NO 57
<211> LENGTH: 54
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 57
gttctcctca tatgcctgct ccaactgcaa cttcggctcc agtcaagccc ggcc         54

<210> SEQ ID NO 58
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 58
tacgcactcc gcggttaaat ctcttcccct cccagca                            37

<210> SEQ ID NO 59
<211> LENGTH: 6
<212> TYPE: PRT
<213> ORGANISM: Human

<400> SEQUENCE: 59

Met Lys Pro Gly Pro Ala
 1               5

<210> SEQ ID NO 60
<211> LENGTH: 5
<212> TYPE: PRT
<213> ORGANISM: Human

<400> SEQUENCE: 60

Gly Gly Glu Glu Ile
 1               5

<210> SEQ ID NO 61
<211> LENGTH: 54
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 61
gttctcctca tatgaaacca ggtccagcct taagctaccc gcaggaggag gcca         54

<210> SEQ ID NO 62
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 62
tacgcactcc gcggttaaat ctcttcccct cccagca                            37

<210> SEQ ID NO 63
<211> LENGTH: 6

```
<212> TYPE: PRT
<213> ORGANISM: Human

<400> SEQUENCE: 63

Met Gln Glu Glu Ala Thr
1               5

<210> SEQ ID NO 64
<211> LENGTH: 5
<212> TYPE: PRT
<213> ORGANISM: Human

<400> SEQUENCE: 64

Gly Gly Glu Glu Ile
1               5

<210> SEQ ID NO 65
<211> LENGTH: 53
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 65
gttctcctca tatgcaagaa gaagctactc tgaatgagat gttccgcgag gtt          53

<210> SEQ ID NO 66
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 66
tacgcactcc gcggttaaat ctcttcccct cccagca                             37

<210> SEQ ID NO 67
<211> LENGTH: 6
<212> TYPE: PRT
<213> ORGANISM: Mouse

<400> SEQUENCE: 67

Met Glu Pro Gly Pro Ala
1               5

<210> SEQ ID NO 68
<211> LENGTH: 5
<212> TYPE: PRT
<213> ORGANISM: Mouse

<400> SEQUENCE: 68

Gly Glu Glu Glu Ile
1               5

<210> SEQ ID NO 69
<211> LENGTH: 54
<212> TYPE: DNA
<213> ORGANISM: Artificial Sequence
<220> FEATURE:
<223> OTHER INFORMATION: Description of Artificial Sequence:
      Oligonucleotide probe

<400> SEQUENCE: 69
gttctcctca tatggaacca ggtccagctt taaactaccc tcaggaggaa gcta          54
```

<210> SEQ ID NO 70
<211> LENGTH: 37
<212> TYPE: DNA
<213> ORGANISM: Artificial Sequence
<220> FEATURE:
<223> OTHER INFORMATION: Description of Artificial Sequence: Oligonucleotide probe

<400> SEQUENCE: 70
tacgcactcc gcggttaaat ctcctcctct ccgccta    37

<210> SEQ ID NO 71
<211> LENGTH: 6
<212> TYPE: PRT
<213> ORGANISM: Human

<400> SEQUENCE: 71

Met Leu Val Leu Asp Phe
 1               5

<210> SEQ ID NO 72
<211> LENGTH: 5
<212> TYPE: PRT
<213> ORGANISM: Human

<400> SEQUENCE: 72

Lys Ile Glu Lys Leu
 1               5

<210> SEQ ID NO 73
<211> LENGTH: 47
<212> TYPE: DNA
<213> ORGANISM: Artificial Sequence
<220> FEATURE:
<223> OTHER INFORMATION: Description of Artificial Sequence: Oligonucleotide probe

<400> SEQUENCE: 73
gttctcctca tatgttagtt ttggatttca acaacatcag gagctct    47

<210> SEQ ID NO 74
<211> LENGTH: 49
<212> TYPE: DNA
<213> ORGANISM: Artificial Sequence
<220> FEATURE:
<223> OTHER INFORMATION: Description of Artificial Sequence: Oligonucleotide probe

<400> SEQUENCE: 74
tacgcactgg atccttacag tttttctatt ttttggcata tcttaatc    49

<210> SEQ ID NO 75
<211> LENGTH: 798
<212> TYPE: DNA
<213> ORGANISM: Human

<400> SEQUENCE: 75
atgatggctc tgggtgctgc tggtgctacc cgtgtttttcg ttgctatggt tgctgctgct    60
ctgggtggtc acccgctgct gggtgtttcc gctaccctga actccgttct gaactccaac    120
gctatcaaaa acctgccgcc gccgctgggt ggtgctgctg gtcacccggg ttccgctgtt    180
tccgctgctc cgggtatcct gtacccgggt ggtaacaaat accagaccat cgacaactac    240
cagccgtacc cgtgcgctga agacgaagaa tgcggtaccg acgaatactg cgcttccccg    300

```
acccgtggtg gtgacgctgg tgttcagatc tgcctggctt gccgtaaacg tcgtaaacgt    360
tgcatgcgtc acgctatgtg ctgcccgggt aactactgca aaaacggtat ctgcgtttcc    420
tccgaccaga accacttccg tggtgaaatc gaagaaacca tcaccgaatc cttcggtaac    480
gaccactcca ccctggacgg ttactcccgt cgtaccaccc tgtcctccaa aatgtaccac    540
accaaaggtc aggaaggttc cgtttgcctg cgttcctccg actgcgcttc cggtctgtgc    600
tgcgctcgtc acttctggtc aaaatctgc aaaccggttc tgaaagaagg tcaggtttgc    660
accaaacacc gtcgtaaagg ttcccacggt ctggaaatct tccagcgttg ctactgcggt    720
gaaggtctgt cctgccgtat ccagaaagac caccaccagg cttccaactc ctcccgtctg    780
cacacctgcc agcgtcac                                                  798

<210> SEQ ID NO 76
<211> LENGTH: 777
<212> TYPE: DNA
<213> ORGANISM: Human

<400> SEQUENCE: 76
atggctgctc tgatgcgttc caaagactcc tcctgctgcc tgctgctgct ggctgctgtt     60
ctgatggttg aatcctccca gatcggttcc tcccgtgcta aactgaactc catcaaatcc    120
tccctgggtg gtgaaacccc gggtcaggct gctaaccgtt ccgctggtat gtaccagggt    180
ctggctttcg gtggttccaa aaaggtaaa aacctgggtc aggcttaccc gtgctcctcc    240
gacaaagaat gcgaagttgg tcgttactgc cactccccgc caccagggttc ctccgcttgc    300 atggtttgcc gtcgtaaaaa aaaacgttgc caccgtgacg gtatgtgctg cccgtccacc    360
cgttgcaaca acggtatctg catcccggtt accgaatcca tcctgacccc gcacatcccg    420
gctctggacg gtacccgtca ccgtgaccgt aaccacggtc actactccaa ccacgacctg    480
ggttggcaga acctgggtcg tccgcacacc aaaatgtccc acatcaaagg tcacgaaggt    540
gacccgtgcc tgcgttcctc cgactgcatc gaaggtttct gctgcgctcg tcacttctgg    600
accaaaatct gcaaaccggt tctgcaccag ggtgaagttt gcaccaaaca gcgtaaaaaa    660
ggttcccacg gtctggaaat cttccagcgt tgcgactgcg ctaaaggtct gtcctgcaaa    720
gtttggaaag acgctaccta ctcctccaaa gctcgtctgc acgtttgcca gaaaatc      777

<210> SEQ ID NO 77
<211> LENGTH: 1050
<212> TYPE: DNA
<213> ORGANISM: Human

<400> SEQUENCE: 77
atgcagcgtc tgggtgctac cctgctgtgc ctgctgctgg ctgctgctgt tccgaccgct     60
ccggctccgg ctccgaccgc tacctccgct ccggttaaac cgggtccggc tctgtcctac    120
ccgcaggaag aagctacccct gaacgaaatg ttccgtgaag ttgaagaact gatggaagac    180
acccagcaca aactgcgttc cgctgttgaa gaaatggaag ctgaagaagc tgctgctaaa    240
gcttcctccg aagttaacct ggctaacctg ccgccgtcct accacaacga accaacacc    300 gacaccaaag ttggtaacaa caccatccac gttcaccgtg aaatccacaa aatcaccaac    360
aaccagaccg gtcagatggt tttctccgaa accgttatca cctccgttgg tgacgaagaa    420
ggtcgtcgtt cccacgaatg catcatcgac gaagactgcg tccgtccat gtactgccag    480 ttcgcttcct tccagtacac ctgccagccg tgccgtggtc agcgtatgct gtgcacccgt    540
```

-continued

```
gactccgaat gctgcggtga ccagctgtgc gtttggggtc actgcaccaa aatggctacc    600
cgtggttcca acggtaccat ctgcgacaac cagcgtgact gccagccggg tctgtgctgc    660
gctttccagc gtggtctgct gttcccggtt tgcaccccgc tgccggttga aggtgaactg    720
tgccacgacc cggcttcccg tctgctggac ctgatcacct gggaactgga accggacggt    780
gctctggacc gttgcccgtg cgcttccggt ctgctgtgcc agccgcactc ccactccctg    840
gtttacgttt gcaaaccgac cttcgttggt tcccgtgacc aggacggtga aatcctgctg    900
ccgcgtgaag ttccggacga atacgaagtt ggttccttca tggaagaagt tcgtcaggaa    960
ctggaagacc tggaacgttc cctgaccgaa gaaatggctc tgggtgaacc ggctgctgct   1020
gctgctgctc tgctgggtgg tgaagaaatc                                    1050

<210> SEQ ID NO 78
<211> LENGTH: 672
<212> TYPE: DNA
<213> ORGANISM: Human

<400> SEQUENCE: 78
atggttgctg ctgttctgct gggtctgtcc tggctgtgct ccccgctggg tgctctggtt     60
ctggacttca caacatccg ttcctccgct gacctgcacg gtgctcgtaa aggttcccag    120
tgcctgtccg acaccgactg caacacccgt aaattctgcc tgcagccgcg tgacgaaaaa    180
ccgttctgcg ctacctgccg tggtctgcgt cgtcgttgcc agcgtgacgc tatgtgctgc    240
ccgggtaccc tgtgcgttaa cgacgtttgc accaccatgg aagacgctac cccgatcctg    300
gaacgtcagc tggacgaaca ggacggtacc cacgctgaag gtaccaccgg tcacccggtt    360
caggaaaacc agccgaaacg taaaccgtcc atcaaaaaat cccagggtcg taaaggtcag    420
gaaggtgaat cctgcctgcg taccttcgac tgcggtccgg gtctgtgctg cgctcgtcac    480
ttctggacca aaatctgcaa accggttctg ctggaaggtc aggtttgctc ccgtcgtggt    540
cacaaagaca ccgctcaggc tccggaaatc ttccagcgtt gcgactgcgg tccgggtctg    600
ctgtgccgtt cccagctgac ctccaaccgt cagcacgctc gtctgcgtgt ttgccagaaa    660
atcgaaaaac tg                                                        672
```